US007355033B2

(12) United States Patent
Shi et al.

(10) Patent No.: US 7,355,033 B2
(45) Date of Patent: Apr. 8, 2008

(54) SCREENING FOR WEST NILE VIRUS ANTIVIRAL THERAPY

(75) Inventors: Pei-Yong Shi, Albany, NY (US); Michael Lo, Albany, NY (US); Mark Tilgner, Albany, NY (US)

(73) Assignee: Health Research, Inc., Rensselaer, NY (US)

( * ) Notice: Subject to any disclaimer, the term of this patent is extended or adjusted under 35 U.S.C. 154(b) by 419 days.

(21) Appl. No.: 10/706,892

(22) Filed: Nov. 13, 2003

(65) Prior Publication Data

US 2005/0058987 A1  Mar. 17, 2005

Related U.S. Application Data

(60) Provisional application No. 60/427,117, filed on Nov. 18, 2002.

(51) Int. Cl.
  C12N 15/40 (2006.01)
  C12N 5/10 (2006.01)
  C12Q 1/18 (2006.01)
(52) U.S. Cl. .............................. 536/23.72; 435/235.1; 435/325; 435/32
(58) Field of Classification Search .................... 435/5, 435/6, 7.1, 347, 373, 235.1, 345, 320.1
  See application file for complete search history.

(56) References Cited

OTHER PUBLICATIONS

Barrett, "Current status of Flavivirus vaccines," Ann. N.Y. Acad. Sci., 951:262-71 (2001).*
Chambers et al., "Yellow Fever/Japanese Encephalitis Chimeric Viruses: Construction and Biological Properties," Journal of Virology, vol. 73, No. 4, pp. 3095-3103 (1999).*
Lai et al., "Evaluation of molecular strategies to develop a live dengue vaccine," Clin. Diag. Virol. 10: 173-79 (1998).*
Friebe et al., "Sequences in the 5' Nontranslated Region of Hepatitis C Virus Required for RNA Replication," Journal of Virology, vol. 75, No. 24 pp. 12047-12057 (2001).*
Pang et al., "Developmebnt of Dengue virus type 2 replicons capable of prolonged expression in host cells," BMC Microbiology, 1:18 (2001).*
Varnavski et al., "Noncytopathic Flavivirus Replicon RNA-based System for Expression and Delivery of Heterologous Genes," Virology 255, pp. 366-375 (1999).*
Zhu et al., "Three-Color Flow Cytometry Analysis of Tricistrionic Expression of eBFP, eGFP, and eYFP Using EMCV-IRES Linkages," Cytometry 37: 51-59 (1999).*
Mishin et al., "A minimal approach in design of flavivirus infectious DNA," Virus Research 81 (2001).*
Puri et al., "Construction of a full length Infectious clone for Dengue-1 Virus Western Pacific, 74 strain," Virus Genes 20:1, pp. 57-63 (2000).*
Xiang et al., "Full-length GB Virus C (Hepatits G virus) RNA transcripts are infectious in primary CD4-positive T cells," Journal of Virology, vol. 74, No. 19 (2000).*
Lanciotti et al (Science 286:2333-2337, 1999).*
Lanciotti et al (Virology 298, 96-105, 2002).*
Ackermann M, Padmanabhan R. (2001) De novo synthesis of RNA by the dengue virus RNA-dependent RNA polymerase exhibits temperature dependence at the initiation but not elongation phase. J Biol Chem Oct. 26, 2001;276(43):39926-37.
Arias CF, Preugschat F, Strauss JH. (1993) Dengue 2 virus NS2B and NS3 form a stable complex that can cleave NS3 within the helicase domain. Virology Apr. 1993;193(2):888-99.
Beasley, D.W.C. et al, (2001) International Conference on the West Nile Virus, New York Academy of Science Poster Section 1:5.
Blackwell J.L., and Brinton M.A. (1995) BHK cell proteins that bind to the 3' stem-loop structure of the West Nile virus genome RNA. J Virol Sep. 1995;69(9):5650-8.
Blackwell JL, Brinton MA. (1997) Translation elongation factor-1 alpha interacts with the 3' stem-loop region of West Nile virus genomic RNA. J Virol 71(9):6433-44.
Brinton MA, Dispoto JH, (1988) Sequence and secondary structure analysis of the 5'-terminal region of flavivirus genome RNA. Virology Feb. 1988;162(2):290-9.
Campbell MS, Pletnev AG: Infectious cDNA clones of Langat tickborne flavivirus that differ from their parent in peripheral neurovirulence. Virology (2000) 268(1):225-237.
Cardosa, M.J., (1998) Dengue vaccine design: issues and challenges. Br Med Bull 1998;54(2):395-405.
Chambers T.J., Hahn CS, Galler R, Rice CM (1990) Flavivirus genome organization, expression, and replication. Annu Rev Microbiol 44:649-88.
Chambers TJ, Grakoui A, Rice CM. (1991) Processing of the yellow fever virus nonstructural polyprotein: a catalytically active NS3 proteinase domain and NS2B are required for cleavages at dibasic sites. J Virol Nov. 1991;65(11):6042-50.

(Continued)

Primary Examiner—Mary E. Mosher
(74) Attorney, Agent, or Firm—Thomas J. Kowalski; Ljiljana Minwalla; Frommer Lawrence and Haug

(57) ABSTRACT

The instant invention provides stable and novel lineage I WNV reverse genetics systems, and methods for making the reverse genetics systems, specifically, a fully-infectious lineage I WNV cDNA or replicon system engineered with one or more nucleotide sequences each encoding a reporter gene to be used in high throughput cell-based screening assays for the identification of novel antiflaviviral chemotherapeutics and/or vaccines effective to treat and/or immunize against infections by WNV and other emerging flaviviruses, such as, for example, JEV, SLEV, AV, KV, JV, CV, YV, TBEV, DENV-1, DENV-2, DENV-3, DENV-4, YFV and MVEV. The present invention further provides methods of high throughput screening of antiflaviviral compounds or improved derivatives thereof using novel lineage I WNV reverse genetics systems and/or cell lines stably containing the reverse genetics systems. Also, the invention provides novel pharmaceutical compositions comprising an attenuated lineage I WNV that is less virulent but similarly immunogenic as the parent WNV and is capable of providing a protective immune response in a host.

19 Claims, 27 Drawing Sheets

OTHER PUBLICATIONS

Chambers TJ, Nestorowicz A, Amberg, SM, Rice CM. (1993) Mutagenesis of the yellow fever virus NS2B protein: effects on proteolytic processing, NS2B-NS3 complex formation, and viral replication. J Virol Nov. 1993;67(11):6797-807.

Diamond MS, Edgil D, Roberts TG, Lu B, Harris E. (2000) Infection of human cells by dengue virus is modulated by different cell types and viral strains. J Virol Sep. 2000;74(17):7814-23.

De Clercq, E. 1993. Antiviral agents: characteristic activity spectrum depending on the molecular target with which they interact. Advance Virus Res. 42:1-55.

Ebel, G.D., Dupuis, A.P., II, Ngo, K.A., Nicholas, D.C., Kaauffman, E.B., Johnes, S.A., Yound, D., Maffei, J., Shi, P.Y., Bernard, K.A., and Kramer L.D. (2001). Partial genetic characterization of West Nile virus strains, New York State, 2000. Emerg. Infect. Dis. 7:650-653.

Falgout B, Miller RH, Lai CJ. (1993) Deletion analysis of dengue virus type 4 nonstructural protein NS2B: identification of a domain required for NS2B-NS3 protease activity. J Virol Apr. 1993;67(4):2034-42.

Gray, N.K. and M. Wicker, (1998) Control of translation in animals, Annu. Rev. Cell Dev. Biol. 14: 399-458.

Guyatt KJ, Westaway EG, Khromykh AA. (2001) Expression and purification of enzymatically active recombinant RNA-dependent RNA polymerase (NS5) of the flavivirus Kunjin. J Virol Methods Mar. 2001;92(1):37-44.

Hicks, B.W. *Green Fluorescent Protein: Applications and Protocols*, vol. 83 of Methods in Cell Biology (2002).

Heinz FX, Allison SL (2000) Structures and mechanisms in flavivirus fusion. Adv Virus Res 2000;55:231-69.

Hellen CU, Witherell GW, Schmid M, Shin SH, Pestova TV, Gil A, Wimmer E. (1993) A cytoplasmic 57-kDa protein that is required for translation of picornavirus RNA by internal ribosomal entry is identical to the nuclear pyrimidine tract-binding protein. Proc Natl Acad Sci 90(16):7642-6.

Hubalek, Z., and J. Halouzka. (1999) West Nile fever—a reemerging mosquito-borne viral disease in Europe. Emerg Infect Dis 5(5):643-50.

Hurrelbrink RJ, Nestorowicz A, McMinn PC: Characterization of Infectious Murray Valley encephalitis virus derived from a stably cloned genomelength cDNA. J Gen Viral (1999) 80(Pt 12):3115-3125.

Jackson RJ, Kaminski A. (1995) Internal initiation of translation in eukaryotes: the picornavirus paradigm and beyond. RNA Dec. 1995;1(10):985-1000.

Jang SK, Krausslich HG, Nicklin MJ, Duke GM, Palmenberg AC, Wimmer E. (1988) A segment of the 5' nontranslated region of encephalomyocarditis virus RNA directs internal entry of ribosomes during in vitro translation. J Virol Aug. 1988;62(8):2636-43.

Jordan I, Briese T. Fischer N, Lau JY, Lipkin WI: Ribavirin inhibits West Nile virus replication and cytopathic effect In neural cells. J Infect Dis (2000) 182(4):1214-1217.

Kapoor M, Zhang L, Mohan PM, Padmanabhan R: Synthesis and characterization of an Infectious dengue virus type-2 RNA genome (New Guinea C strain). Gene (1995) 162(2):175-180.

Kaminski A, Hunt SL, Patton JG, Jackson RJ. (1995) Direct evidence that polypyrimidine tract binding protein (PTB) is essential for internal initiation of translation of encephalomyocarditis virus RNA. RNA Nov. 1995;1(9):924-38.

Khromykh AA, Westaway EG: Completion of Kunjin virus RNA sequence and recovery of an Infectious RNA transcribed from stably cloned full-length cDNA. J Virol (1994) 68(7):4580-4588.

Khromykh AA. Westaway EG: Subgenomic replicons of the flavivirus Kunjin: Construction and applicatons. J Virol (1997) 71(2):1497-1505.

Koonin EV. (1993) Computer-assisted identification of a putative methyltransferase domain in NS5 protein of flaviviruses and lambda 2 protein of reovirus. J Gen Virol Apr. 1993;74 ( Pt 4):733-40.

Kummerer BM, Rice CM. (2002) Mutations in the yellow fever virus nonstructural protein NS2A selectively block production of infectious particles. J Virol May 2002;76(10):4773-84.

Lai CJ, Zhao BT, Hod H, Bray M: Infectious RNA transcribed from stably cloned full-length cDNA of dengue type 4 virus. Proc Natl Acad Sci USA (1991) 88(12):5139-5143.

Lanciotti RS, Roehrig JT, Deubel V, Smith J, Parker M, Steele K, Crise B, Volpe KE, Crabtree MB, Scherret JH, Hall RA, MacKenzie JS, Cropp CB, Panigrahy B, Ostlund E, Schmitt B, Malkinson M, Banet C, Weissman J, Komar N, Savage HM, Stone W, McNamara T, Gubler DJ. (1999) Origin of the West Nile virus responsible for an outbreak of encephalitis in the northeastern United States. Science 286(5448):2333-7.

Lanciotti RS, Ebel GD, Deubel V, Kerst AJ, Murri S, Meyer R, Bowen M, McKinney N, Morrill WE, Crabtree MB, Kramer LD, Roehrig JT. (2002) Complete genome sequences and phylogenetic analysis of West Nile virus strains isolated from the United States, Europe, and the Middle East. Virology 298(1):96-105.

Leda, R., *Methods in Molecular Biology*, Humana Press, v. 165 (2001).

Lindenbach, B.D. and C.M. Rice, *Fields Virology*, Fourth Edition, vol. 1 D.M. Knipe and P.M. Howley, ed, Lippincott Williams and Wilkins, Philadelphia, PA, (2001).

Lindenbach BD, Rice CM. (1997) trans-Complementation of yellow fever virus NS1 reveals a role in early RNA replication. J Virol Dec. 1997;71(12):9608-17.

Lindenbach BD, Rice CM. (1999) Genetic interaction of flavivirus nonstructural proteins NS1 and NS4A as a determinant of replicase function. J Virol Jun. 1999;73(6):4611-21.

Lo, J.K., Tilgner, M., and Shi, P.Y. 2003. A potential high-throughput assay for screening inhibitors of West Nile virus replication. J. Virol. 77, 12901-12906.

Mandl CW, Ecker M, Holzmann H, Kunz C, Heinz FX: Infectious cDNA clones of tick-borne encephalitis virus European subtype prototypic strain Neudoerfl and high virulence strain Hypr. J Gen Virol (1997) 78(Pt 5):1049-1057.

McSharry JJ. (1994) Uses of flow cytometry in virology. Clin Microbiol Rev Oct. 1994;7(4):576-604.

McSharry JJ. (2000) Analysis of virus-infected cells by flow cytometry. Methods Jul. 2000;21(3):249-57.

Meerovitch K, Svitkin YV, Lee HS, Lejbkowicz F, Kenan DJ, Chan EK, Agol VI, Keene JD, Sonenberg N. (1993) La autoantigen enhances and corrects aberrant translation of poliovirus RNA in reticulocyte lysate J Virol Jul. 1993;67(7):3798-807.

Monath, T. 2001. Prospects for development of a vaccine against the West Nile virus. Ann. N. Y. Acad. Sci. 951:1-12.

Morrey JD, Smee DF, Sidwell RW, Tsang C: Identification of active antiviral compounds against a New York Isolate of West Nile virus. Antiviral Res (2002) 55(1):107-116.

Muylaert IR, Chambers TJ, Galler R, Rice CM. (1996) Mutagenesis of the N-linked glycosylation sites of the yellow fever virus NS1 protein: effects on virus replication and mouse neurovirulence. Virology Aug. 1, 1996;222(1):159-68.

Muylaert IR, Galler R, Rice CM. (1997) Genetic analysis of the yellow fever virus NS1 protein: identification of a temperature-sensitive mutation which blocks RNA accumulation. J Virol Jan. 1997;71(1):291-8.

Parham, P. *Immunology* New York, Garland Press (2000).

Pelletier J, Kaplan G, Racaniello VR, Sonenberg N. (1998) Cap-independent translation of poliovirus mRNA is conferred by sequence elements within the 5' noncoding region Mol Cell Biol 8(3):1103-12.

Pelletier J, Kaplan G, Racaniello VR, Sonenberg N. (1998) Translational efficiency of poliovirus mRNA: mapping inhibitory cis-acting elements within the 5' noncoding region. J Virol 62(7):2219-27.

Pestova TV, Shatsky IN, Fletcher SP, Jackson RJ, Hellen CU. (1998) A prokaryotic-like mode of cytoplasmic eukaryotic ribosome binding to the initiation codon during internal translation initiation of hepatits C and classical swine fever virus RNAs. Genes Dev 12(1):67-83.

Polo S, Ketner G, Levis R, Falgout 8: Infectious RNA transcripts from full-length dengue virus type 2 cDNA clones made in yeast. J Virol (1997) 71(7):5366-5374.

Proutski V, Gould EA, Holmes EC. (1997) Secondary structure of the 3' untranslated region of flaviviruses: similarities and differences. Nucleic Acids Res Mar. 15, 1997;25(6):1194-1202.

Rauscher S, Flamm C, Mandl CW, Heinz FX, Stadler PF. (1997) Secondary structure of the 3'-noncoding region of flavivirus genomes: comparative analysis of base pairing probabilities. RNA 3(7):779-91.

Rey FA, Heinz FX, Mandl C, Kunz C, Harrison SC (1995) The envelope glycoprotein from tick-bone encephalitis virus at 2 A resolution. Nature May 25, 1995;375(6529):291-8.

Rice CM, Lendxes EM. Eddy SR, Shin SJ, Sheets RL, Strauss JH: Nucleotide sequence of yellow fever virus: Implications for flavivirus gene expression and evolution. Science (1985) 229(4715):726-733.

Shi, P. Y. 2002. Strategies for the identification of inhibitors of West Nile virus and other flaviviruses. Curr. Opin. Investig. Drugs. 3:1567-73.

Shi, P. Y., E. B. Kauffman, P. Ren, A. Felton, J. H. Tai, A. P. Dupuis, 2nd, S. A. Jones, K. A. Ngo, D. C. Nicholas, J. Maffei, G. D. Ebel, K. A. Bernard, and L. D. Kramer. 2001. High-throughput direction of West Nile virus RNA. J. Clin. Microbiol. 39:1264-71.

Shi, P. Y., M. Tilgner, and M. K. Lo. 2002. Construction and characterization of subgenomic replicons of New York strain of West Nile virus. Virology 296:219-233.

Shi, P. Y., M. Tilgner, M. K. Lo, K. A. Kent, and K. A. Bernard. 2002. Infectious cDNA clone of the epidemic west nile virus from New York City. J. Virol. 76:5847-56.

Sumiyoshi H, Hoke CH, Trent DW: Infectious Japanese encephalitis virus RNA can be synthesized from In vitro-ligated cDNA templates. J Virol (1992) 66(9):5425-5431.

Svitkin YV, Meerovitch K, Lee HS, Dholakia JN, Kenan DJ, Agol VI, Sonenberg N. (1994) Internal translation initiation on poliovirus RNA: further characterization of La function in poliovirus translation in vitro. J Virol Mar. 1994;68(3):1544-50.

Tan BH, Fu J, Sugrue RJ, Yap EH, Chan YC, Tan YH. (1996) Recombinant dengue type 1 virus NS5 protein expressed in *Escherichia coli* exhibits RNA-dependent RNA polymerase activity. Virology Feb. 15, 1996;216(2):317-25.

Wu S-F, Lee CJ, Liao C-L, Dwek R, Zitzmann N, Lin Y-L: Antiviral effects of an iminosugar derivative of flavivirus Infections. J Virol (2002) 76(8):3596-3604.

Yamshchikov VF, Wangler G, Perelygin AA, Brinton MA, Compans RW: An infectious clone of the West Nile flavivirus. Virology (2001) 281(2):294-304.

\* cited by examiner

FIG. 1

Summary of sequence differences between the infectious
cDNA clone and parental WNV strain 3356

| Nucleotide no.[a] | Strain 3356 genome | cDNA clone | Amino acid change | Location |
|---|---|---|---|---|
| 1285 | T | C | Silent | E |
| 3840 | T | C | Silent | NS2A |
| 7015 | C | T | Silent | NS4B |
| 7826 | T | C | V → A | NS5 |
| 8067 | G | A | Silent | NS5 |
| 8859[b] | C | A | Silent | NS5 |
| 8862[b] | A | G | Silent | NS5 |
| 8880[c] | A | G | Silent | NS5 |
| 9123 | C | T | Silent | NS5 |
| 10613 | C | T | Silent | 3'UTR |
| 10783 | C | T | Silent | 3'UTR |

[a] Nucleotide position and sequence are based on WNV strain 3356 (GenBank accession no. AF404756).

[b] Mutations were designed to generate an endonuclease StyI site as a marker for recombinant virus.

[c] This mutation was designed to knock out the endonuclease EcoRI site as a marker for recombinant virus.

FIG. 2

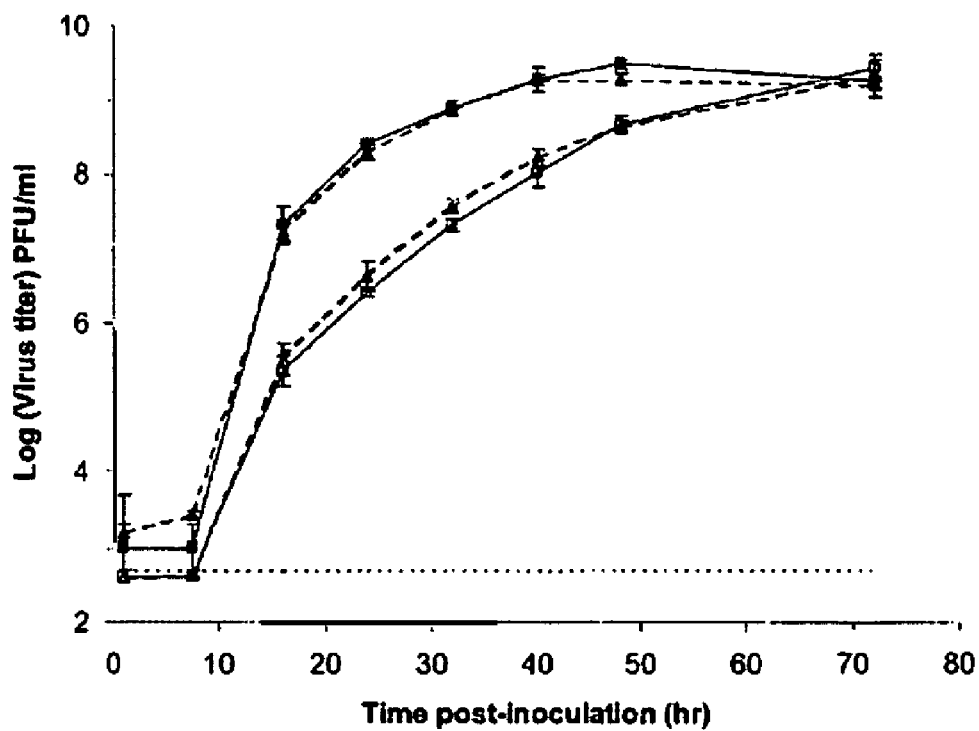
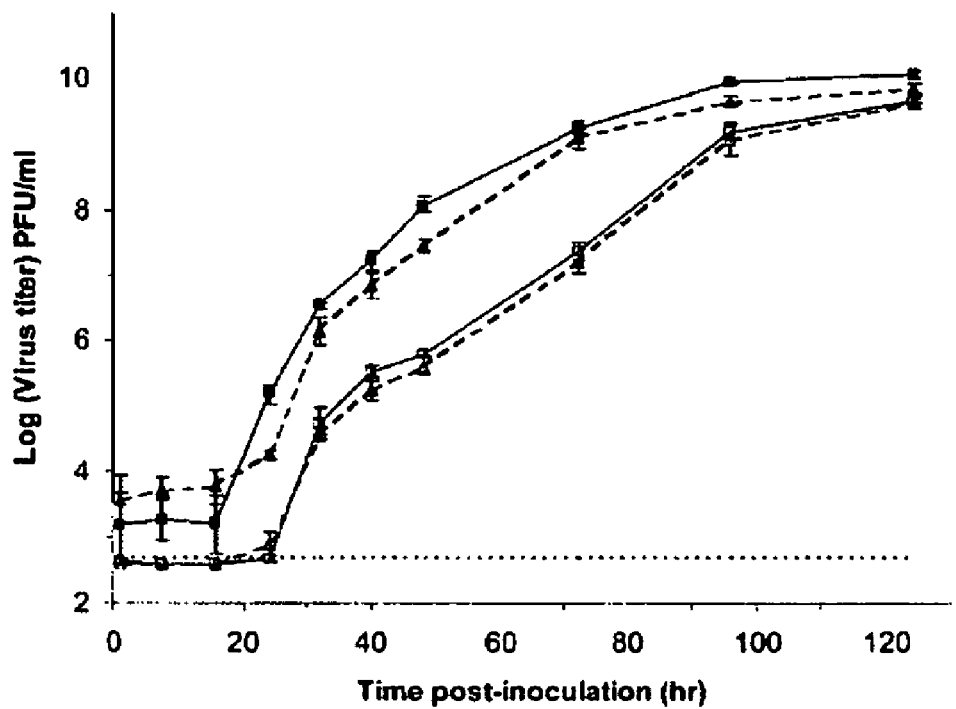
FIG. 7

A

```
            ┌Transcript start
            │  ┌WNV 5' end    WNV 3' end┐
5'---[T7 Promoter]--TAG AGTAG------------GATCT CTAG AT---3'
3'---            --ATC TCATC------------CTAGA GATC TA---5'
                                                    Xbal
                        ↓ Xba I
                        ↓ Mung bean nuclease
                        ↓ Transcription
                        ↓ DNase 5'G AGUAG------------GAUCU 3'
                    WNV sequence
```

B

Lanes: 1 Genome, 2 Replicon, 3 +GFPRep, 4 −GFPRep, 5 NeoRep

FIG. 9

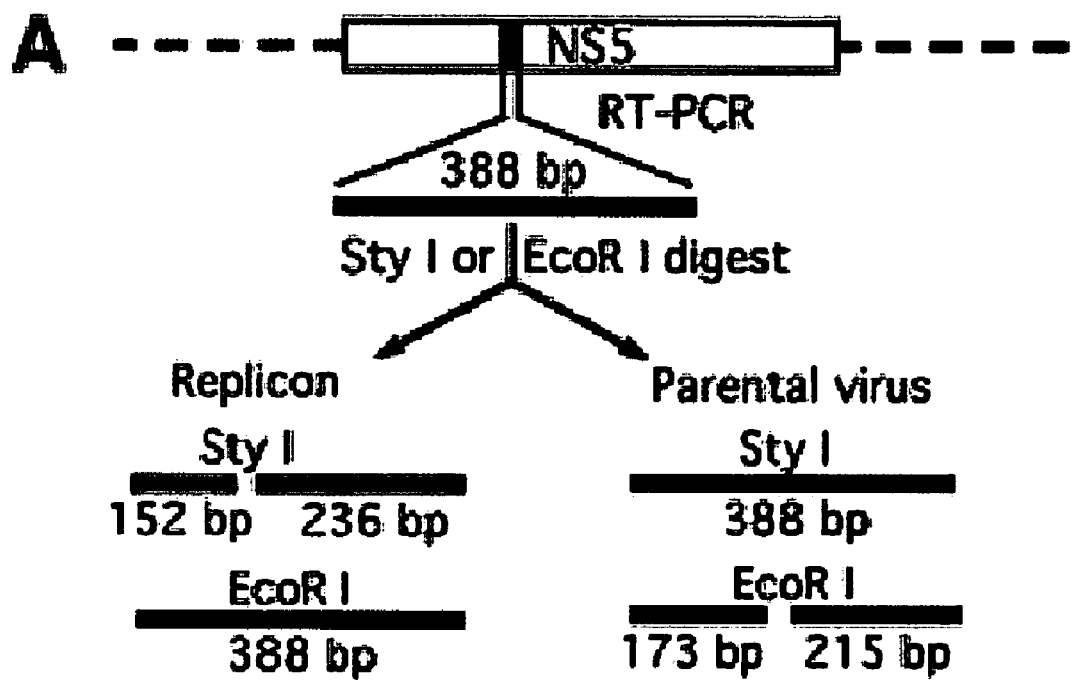
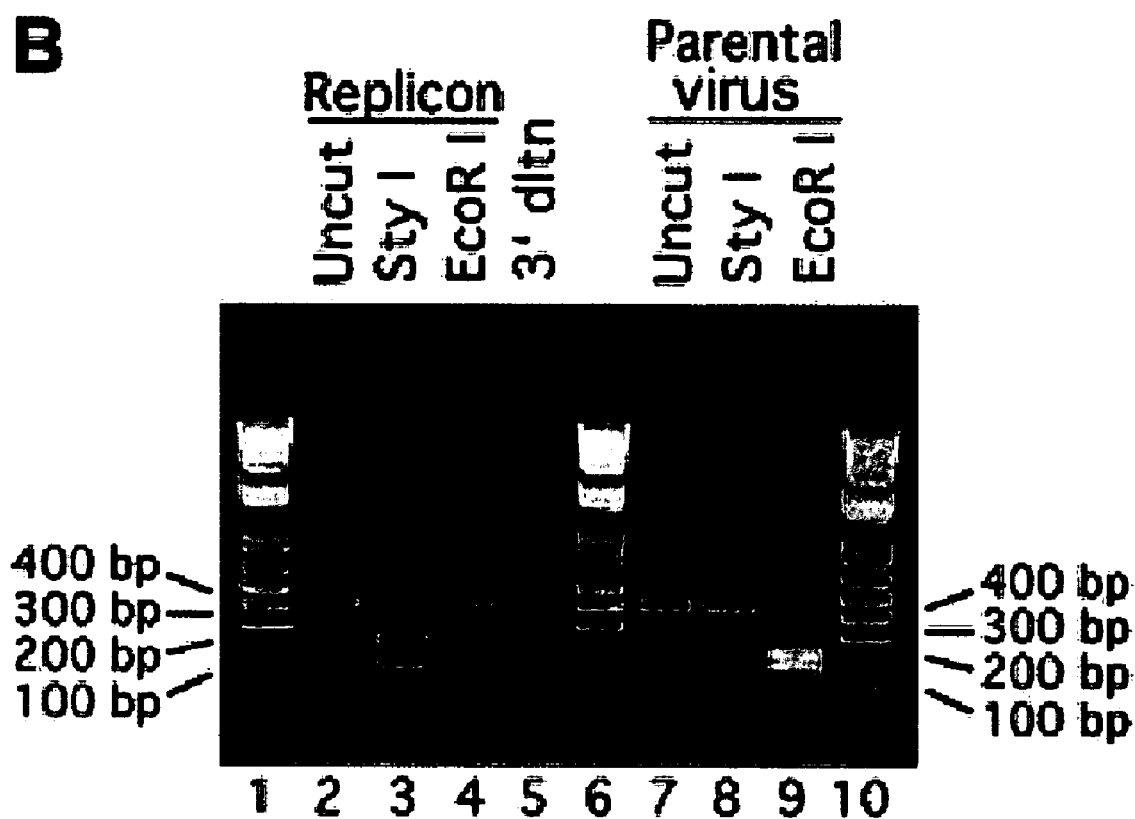
FIG. 12

A NeoRep transfected cells
Phase contrast 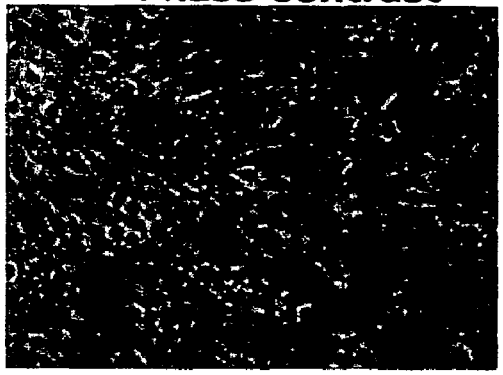 FITC 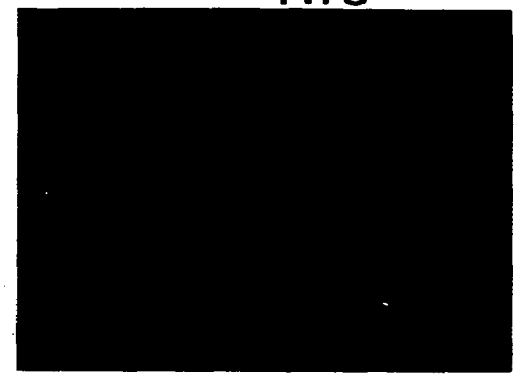
B Neo selected NeoRep cells (15 days)
Phase contrast  FITC 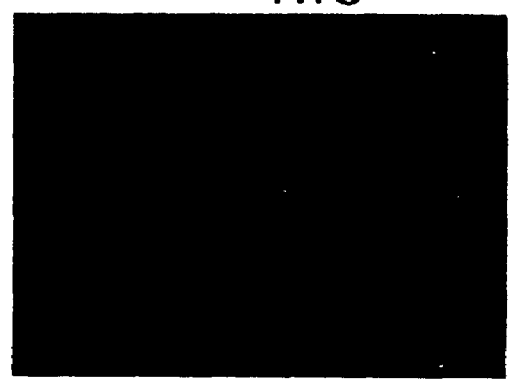
Neo selected NeoRep cells (40 days)
DIC 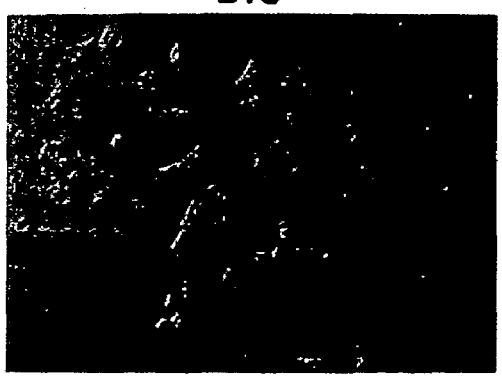 FITC 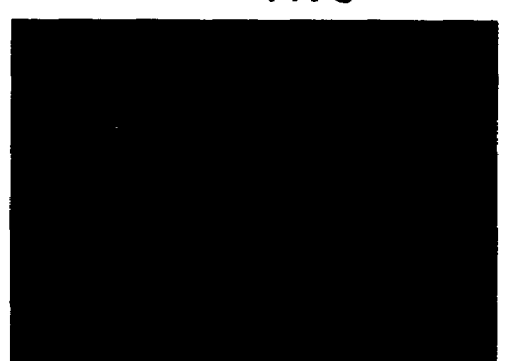
FIG. 15

Complete Nucleotide Sequence of Lineage I WNV Strain 3356 GenBank accession N. AF404756
*(Nucleotide positions indicated in bold underline are different than corresponding positions of FIG. 2)*

FIG. 20 a

```
   1    agtagttcgc ctgtgtgagc tgacaaactt agtagtgttt gtgaggatta acaacaatta
  61    acacagtgcg agctgtttct tagcacgaag atctcgatgt ctaagaaacc aggagggccc
 121    ggcaagagcc gggctgtcaa tatgctaaaa cgcggaatgc cccgcgtgtt gtccttgatt
 181    ggactgaaga gggctatgtt gagcctgatc gacggcaagg gccaatacg atttgtgttg
 241    gctctcttgg cgttcttcag gttcacagca attgctccga cccgagcagt gctggatcga
 301    tggagaggtg tgaacaaaca aacagcgatg aaacccttc tgagttttaa gaaggaacta
 361    gggaccttga ccagtgctat caatcggcgg agctcaaaac aaaagaaaag aggaggaaag
 421    accggaattg cagtcatgat tggcctgatc gccagcgtag gagcagttac cctctctaac
 481    ttccaaggga aggtgatgat gacggtaaat gctactgacg tcacagatgt catcacgatt
 541    ccaacagctg ctggaaagaa cctatgcatt gtcagagcaa tggatgtggg atacatgtgc
 601    gatgatacta tcacttatga atgcccagtg ctgtcggctg taatgatcc agaagacatc
 661    gactgttggt gcacaaagtc agcagtctac gtcaggtatg aagatgcac caagacacgc
 721    cactcaagac gcagtcggag gtcactgaca gtgcagacac acggagaaag cactctagcg
 781    aacaagaagg gggcttggat ggacagcacc aaggccacaa ggtatttggt aaaaacagaa
 841    tcatggatct tgaggaaccc tggatatgcc ctggtggcag ccgtcattgg ttggatgctt
 901    gggagcaaca ccatgcagag agttgtgttt gtcgtgctat tgcttttggt ggccccagct
 961    tacagcttca actgccttgg aatgagcaac agagacttct tggaaggagt gtctggagca
1021    acatgggtgg atttggttct cgaaggcgac agctgcgtga ctatcatgtc taaggacaag
1081    cctaccatcg atgtgaagat gatgaatatg gaggcggcca acctggcaga ggtccgcagt
1141    tattgctatt tggctaccgt cagcgatctc tccaccaaag ctgcgtgccc gaccatggga
1201    gaagctcaca atgacaaacg tgctgaccca gcttttgtgt gcagacaagg agtggtggac
1261    agggctggg gcaacggctg cgga_t_tattt ggcaaaggaa gcattgacac atgcgccaaa
1321    tttgcctgct ctaccaaggc aataggaaga accatcttga aagagaatat caagtacgaa
1381    gtggccattt tgtccatgg accaactact gtggagtcgc acggaaacta ctccacacag
1441    gttggagcca ctcaggcagg gagattcagc atcactcctg cggcgccttc atacacacta
1501    aagcttggag aatatggaga ggtgacagtg gactgtgaac cacggtcagg gattgacacc
1561    aatgcatact acgtgatgac tgttggaaca aagacgttct tggtccatcg tgagtggttc
1621    atggacctca acctcccttg gagcagtgct ggaagtactg tgtgaggaa cagagagacg
1681    ttaatggagt tgaggaacc acacgccacg aagcagtctg tgatagcatt gggctcacaa
1741    gagggagctc tgcatcaagc tttggctgga gccattcctg tggaattttc aagcaacact
1801    gtcaagttga cgtcgggtca tttgaagtgt agagtgaaga tggaaaaatt gcagttgaag
1861    ggaacaacct atggcgtctg ttcaaaggct ttcaagtttc tgggactcc cgcagacaca
1921    ggtcacggca ctgtggtgtt ggaattgcag tacactggca cggatggacc ttgtaaagtt
1981    cctatctcgt cagtggcttc attgaacgac ctaacgccag tgggcagatt ggtcactgtc
2041    aaccctttg tttcagtggc cacggccaac gctaaggtcc tgattgaatt ggaaccaccc
2101    tttggagact catacatagt ggtgggcaga ggagaacaac agatcaatca ccattggcac
2161    aagtctggaa gcagcattgg caaagccttt acaaccaccc tcaaaggagc gcagagacta
2221    gccgctctag agacacagc ttgggacttt ggatcagttg gagggtgtt cacctcagtt
2281    gggaaggctg tccatcaagt gttcggagga gcattccgct tactgttcgg aggcatgtcc
2341    tggataacgc aaggattgct gggggctctc ctgttgtgga tgggcatcaa tgctcgtgat
2401    aggtccatag ctctcacgtt tctcgcagtt ggaggagttc tgctcttcct ctccgtgaac
2461    gtgcacgctg acactgggtg tgccatagac atcagccggc aagagctgag atgtggaagt
2521    ggagtgttca tacacaatga tgtggaggct ggatggacc gatacaagta ttaccctgaa
2581    acgccacaag gcctagccaa gatcattcag aaagctcata aggaagagt gtgcggtcta
2641    cgatcagttt ccagactgga gcatcaaatg tgggaagcag tgaaggacga gctgaacact
2701    cttttgaagg agaatggtgt ggaccttagt gtcgtggttg agaaacagga gggaatgtac
2761    aagtcagcac ctaaacgcct caccgccacc acggaaaaat tggaaattgg ctggaaggcc
2821    tggggaaaga gtatttatt tgcaccagaa ctcgccaaca cacctttgt ggttgatggt
2881    ccggagacca aggaatgtcc gactcagaat cgcgcttgga atagcttaga agtggaggat
2941    tttggatttg gtctcaccag cactcggatg ttcctgaagg tcagagagag caacacaact
3001    gaatgtgact cgaagatcat ggaacggct gtcaagaaca cttggcgat ccacagtgac
3061    ctgtcctatt ggattgaaag caggctcaat gatacgtgga agcttgaaag ggcagttctg
3121    ggtgaagtca atcatgtac gtggcctgag acgcatacct tgtggggcga tggaatccct
3181    gagagtgact tgataatacc agtcacactg gcgggaccac gaagcaatca caatcgggaga
```

Complete Nucleotide Sequence of Lineage I WNV Strain 3356 GenBank accession No. AF404756
*(Nucleotide positions indicated in bold underline are different than corresponding positions of FIG. 2)*

FIG. 20 b

```
3241  cctgggtaca agacacaaaa ccagggccca tgggacgaag gccgggtaga gattgacttc
3301  gattactgcc caggaactac ggtcaccctg agtgagagct gcggacaccg tggacctgcc
3361  actcgcacca ccacagagag cggaaagttg ataacagatt ggtgctgcag gagctgcacc
3421  ttaccaccac tgcgctacca aactgacagc ggctgttggt atggtatgga gatcagacca
3481  cagagacatg atgaaaagac cctcgtgcag tcacaagtga atgcttataa tgctgatatg
3541  attgacccctt tcagttggg ccttctggtc gtgttcttgg ccacccagga ggtccttcgc
3601  aagaggtgga cagccaagat cagcatgcca gctatactga ttgctctgct agtcctggtg
3661  tttgggggca ttacttacac tgatgtgtta cgctatgtca tcttggtggg ggcagctttc
3721  gcagaatcta attcgggagg agacgtggta cacttggcgc tcatggcgac cttcaagata
3781  caaccagtgt ttatggtggc atcgtttctc aaagcgagat ggaccaacca ggagaacatt
3841  ttgttgatgt tggcggctgt tttctttcaa atggcttatc acgatgcccg ccaaattctg
3901  ctctgggaga tccctgatgt gttgaattca ctggcggtag cttggatgat actgagagcc
3961  ataacattca caacgacatc aaacgtggtt gttccgctgc tagccctgct aacacccggg
4021  ctgagatgct tgaatctgga tgtgtacagg atactgctgt tgatggtcgg aataggcagc
4081  ttgatcaggg agaagaggag tgcagctgca aaaagaaag gagcaagtct gctatgcttg
4141  gctctagcct caacaggact tttcaacccc atgatccttg ctgctggact gattacatgt
4201  gatcccaacc gtaaacgcgg atgggccgca actgaagtga tgacagctgt cggcctgatg
4261  tttgccatcg tcggagggct ggcagagctt gacattgact ccatggccat tccaatgact
4321  atcgcggggc tcatgtttgc tgctttcgtg atttctggga atcaacaga tatgtggatt
4381  gagagaacgg cggacatttc ctgggaaagt gatgcagaaa ttacaggctc gagcgaaaga
4441  gttgatgtgc ggcttgatga tgatggaaac ttccagctca tgaatgatcc aggagcacct
4501  tggaagatat ggatgctcag aatggtctgt ctcgcgatta gtgcgtacac ccctgggca
4561  atcttgccct cagtagttgg attttggata actctccaat acacaaagag aggaggcgtg
4621  ttgtgggaca ctccctcacc aaaggagtac aaaaaggggg acacgaccac cggcgtctac
4681  aggatcatga ctcgtgggct gctcggcagt tatcaagcag gagcgggcgt gatggttgaa
4741  ggtgttttcc acaccctttg gcatacaaca aaaggagccg ctttgatgag cggagagggc
4801  cgcctggacc catactgggg cagtgtcaag gaggatcgac tttgttacgg aggaccctgg
4861  aaattgcagc acaagtggaa cgggcaggat gaggtgcaga tgattgtggt ggaacctggc
4921  aagaacgtta agaacgtcca gacgaaacca ggggtgttca aaacacctga aggagaaatc
4981  ggggccgtga ctttggactt ccccactgga acatcaggct caccaatagt ggacaaaaac
5041  ggtgatgtga ttgggctta tggcaatgga gtcataatgc caacggctc atacataagc
5101  gcgatagtgc agggtgaaag gatggatgag ccaatcccag ccggattcga acctgagatg
5161  ctgaggaaaa aacagatcac tgtactggat ctccatcccg gcgccggtaa aacaaggagg
5221  attctgccac agatcatcaa agaggccata aacagaagac tgagaacagc cgtgctagca
5281  ccaaccaggg ttgtggctgc tgagatggct gaagcactga gaggactgcc catccggtac
5341  cagacatccg cagtgcccag agaacataat ggaaatgaga ttgttgatgt catgtgtcat
5401  gctaccctca cccacaggct gatgtctcct cacagggtgc cgaactacaa cctgttcgtg
5461  atggatgagg ctcatttcac cgacccagct agcattgcag caagaggtta catttccaca
5521  aaggtcgagc taggggaggc ggcggcaata ttcatgacag ccaccccacc aggcacttca
5581  gatccattcc cagagtccaa ttcaccaatt tccgacttac agactgagat cccggatcga
5641  gcttggaact ctggatacga atggatcaca gaatacaccg ggaagacggt ttggtttgtg
5701  cctagtgtca agatggggaa tgagattgcc ctttgcctac aacgtgctgg aaagaaagta
5761  gtccaattga acagaaagtc gtacgagacg gagtacccaa aatgtaagaa cgatgattgg
5821  gactttgtta tcacaacaga catatctgaa atggggcta actttaaggc gagcagggtg
5881  attgacagcc ggaagagtgt gaaaccaacc atcataacag aaggagaagg gagagtgatc
5941  ctgggagaac catctgcagt gacagcagct agtgccgccc agagacgtgg acgtatcggt
6001  agaaatccgt cgcaagttgg tgatgagtac tgttatgggg ggcacacgaa tgaagacgac
6061  tcgaacttcg cccattggac tgaggcacga atcatgctgg acaacatcaa catgccaaac
6121  ggactgatcg ctcaattcta ccaaccagag cgtgagaagg tatataccat ggatggggaa
6181  taccggctca gaggagaaga gagaaaaaac tttctggaac tgttgaggac tgcagatctg
6241  ccagtttggc tggcttacaa ggttgcagcg gctggagtgt cataccacga ccggagtgg
6301  tgctttgatg gtcctaggac aaacacaatt ttagaagaca acaacgaagt ggaagtcatc
6361  acgaagcttg gtgaaaggaa gattctgagg ccgcgctgga ttgacgccag ggtgtactcg
```

Complete Nucleotide Sequence of Lineage I WNV Strain 3356 GenBank accession No. AF404756
*(Nucleotide positions indicated in bold underline are different than corresponding positions of FIG. 2)*

FIG. 20 c

```
6421  gatcaccagg cactaaaggc gttcaaggac ttcgcctcgg gaaaacgttc tcagataggg
6481  ctcattgagg ttctgggaaa gatgcctgag cacttcatgg ggaagacatg ggaagcactt
6541  gacaccatgt acgttgtggc cactgcagag aaggaggaa gagctcacag aatggccctg
6601  gaggaactgc cagatgctct tcagacaatt gccttgattg ccttattgag tgtgatgacc
6661  atgggagtat tcttcctcct catgcagcgg aagggcattg gaaagatagg tttgggaggc
6721  gctgtcttgg gagtcgcgac ctttttctgt tggatggctg aagttccagg aacgaagatc
6781  gccggaatgt tgctgctctc ccttctcttg atgattgtgc taattcctga gccagagaag
6841  caacgttcgc agacagacaa ccagctagcc gtgttcctga tttgtgtcat gacccttgtg
6901  agcgcagtgg cagccaacga gatgggttgg ctagataaga ccaagagtga cataagcagt
6961  ttgtttgggc aaagaattga ggtcaaggag aatttcagca tgggagagtt tcttctggac
7021  ttgaggccgg caacagcctg gtcactgtac gctgtgacaa cagcggtcct cactccactg
7081  ctaaagcatt tgatcacgtc agattacatc aacacctcat tgacctcaat aaacgttcag
7141  gcaagtgcac tattcacact cgcgcgaggc ttcccctcg tcgatgttgg agtgtcggct
7201  ctcctgctag cagccggatg ctggggacaa gtcaccctca ccgttacggt aacagcggca
7261  acactccttt tttgccacta tgcctacatg gttcccggtt ggcaagctga ggcaatgcgc
7321  tcagcccagc ggcggacagc ggccggaatc atgaagaacg ctgtagtgga tggcatcgtg
7381  gccacggacg tcccagaatt agagcgcacc acacccatca tgcagaagaa agttggacag
7441  atcatgctga tcttggtgtc tctagctgca gtagtagtga cccgtctgt gaagacagta
7501  cgagaagccg gaattttgat cacggccgca gcggtgacgc tttgggagaa tggagcaagc
7561  tctgtttgga acgcaacaac tgccatcgga ctctgccaca tcatgcgtgg gggttggttg
7621  tcatgtctat ccataacatg gacactcata agaacatgg aaaaaccagg actaaaaga
7681  ggtgggcaa aaggacgcac cttgggagag gtttggaaag aaagactcaa ccagatgaca
7741  aaagaagagt tcactaggta ccgcaaagag gccatcatcg aagtcgatcg ctcagcagca
7801  aaacacgcca ggaaagaagg caatgtcact ggagggcatc cagtctctag ggcacagca
7861  aaactgagat ggctggtcga acggaggttt ctcgaaccgg tcggaaaagt gattgacctt
7921  ggatgtggaa gaggcggttg gtgttactat atggcaaccc aaaaaagagt ccaagaagtc
7981  agagggtaca caaagggcgg tcccggacat gaagagcccc aactagtgca agttatgga
8041  tggaacattg tcaccatgaa gagtgggtg gatgtgttct acagaccttc tgagtgttgt
8101  gacaccctcc tttgtgacat cggagagtcc tcgtcaagtg ctgaggttga agagcatagg
8161  acgattcggg tccttgaaat ggttgaggac tggctgcacc gagggccaag ggaattttgc
8221  gtgaaggtgc tctgcccta catgccgaaa gtcatagaga gatggagct gctccaacgc
8281  cggtatgggg gggactggt cagaaaccca ctctcacgga attccacgca cgagatgtat
8341  tgggtgagtc gagcttcagg caatgtggta cattcagtga atatgaccag ccaggtgctc
8401  ctaggaagaa tggaaaaaag gacctggaag ggaccccaat acgaggaaga tgtaaacttg
8461  ggaagtggaa ccagggcggt gggaaaaccc ctgctcaact cagacaccag taaaatcaag
8521  aacaggattg aacgactcag gcgtgagtac agttcgacgt ggcaccacga tgagaaccac
8581  ccatatagaa cctggaacta tcacggcagt tatgatgtga gcccacagg ctccgccagt
8641  tcgctggtca atggagtggt caggctcctc tcaaaaccat gggacaccat cacgaatgtt
8701  accaccatgg ccatgactga cactactccc ttcgggcagc agcgagtgtt caaagagaag
8761  gtggacacga agctcctga accgccagaa ggagtgaagt acgtgctcaa-cgagaccacc
8821  aactggttgt gggcgttttt ggccagagaa aacgtccca gaatgtgctc tcgagaggaa
8881  ttcataagaa aggtcaacag caatgcagct tgggtgcca tgtttgaaga gcagaatcaa
8941  tggaggagcg ccagagaggc agttgaagat ccaaattt gggagatggt ggatgaggag
9001  cgcgaggcac atctgcgggg ggaatgtcac acttgcattt acaacatgat ggaaagaga
9061  gagaaaaac ccggagagtt cggaaaggcc aagggaagca gagccatttg gttcatgtgg
9121  ctcggagctc gctttctgga gttcgaggct ctgggtttc tcaatgaaga ccactggctt
9181  ggaagaaaga actcaggagg aggtgtcgag gcttgggcc tccaaaaact gggttacatc
9241  ctgcgtgaag ttggcacccg gcctggggc aagatctatg ctgatgacac agctggctgg
9301  gacacccgca tcacgagagc tgacttggaa aatgaagcta aggtgcttga gctgcttgat
9361  ggggaacatc ggcgtcttgc cagggccatc attgagctca cctatcgtca. caaagttgtg
9421  aaagtgatgc gcccggctgc tgatggaaga accgtcatgg atgttatctc cagagaagat
9481  cagaggggga gtggacaagt tgtcacctac gccctaaca cttcaccaa cctggccgtc
9541  cagctggtga ggatgatgga agggaagga gtgattggcc cagatgatgt ggagaaactc
9601  acaaagggga aggacccaa agtcaggacc tggctgtttg agaatgggga agaaagactc
```

Complete Nucleotide Sequence f Lineage I WNV Strain 3356 GenBank accession No. AF404756
*(Nucleotide positions indicated in bold underline are different than corresponding positions of FIG. 2)*

FIG. 20 d

```
 9661 agccgcatgg ctgtcagtgg agatgactgt gtggtaaagc ccctggacga tcgctttgcc
 9721 acctcgctcc acttcctcaa tgctatgtca aaggttcgca aagacatcca agagtggaaa
 9781 ccgtcaactg gatggtatga ttggcagcag gttccatttt gctcaaacca tttcactgaa
 9841 ttgatcatga aagatggaag aacactggtg gttccatgcc gaggacagga tgaattggta
 9901 ggcagagctc gcatatctcc agggccgga tggaacgtcc gcgacactgc ttgtctggct
 9961 aagtcttatg cccagatgtg gctgcttctg tacttccaca gaagagacct gcggctcatg
10021 gccaacgcca tttgctccgc tgtccctgtg aattgggtcc ctaccggaag aaccacgtgg
10081 tccatccatg caggaggaga gtggatgaca acagaggaca tgttggaggt ctggaaccgt
10141 gtttggatag aggagaatga atggatggaa gacaaaaccc cagtggagaa atggagtgac
10201 gtcccatatt caggaaaacg agaggacatc tggtgtggca gcctgattgg cacaagagcc
10261 cgagccacgt gggcagaaaa catccaggtg gctatcaacc aagtcagagc aatcatcgga
10321 gatgagaagt atgtggatta catgagttca ctaaagagat atgaagacac aactttggtt
10381 gaggacacag tactgtagat atttaatcaa ttgtaaatag acaatataag tatgcataaa
10441 agtgtagttt tatagtagta tttagtggtg ttagtgtaaa tagttaagaa aattttgagg
10501 agaaagtcag gccgggaagt tccgccacc ggaagttgag tagacggtgc tgcctgcgac
10561 tcaaccccag gaggactggg tgaacaaagc cgcgaagtga tccatgtaag ccctcagaac
10621 cgtctcggaa ggaggacccc acatgttgta acttcaaagc ccaatgtcag accacgctac
10681 ggcgtgctac tctgcggaga gtgcagtctg cgatagtgcc ccaggaggac tgggttaaca
10741 aaggcaaacc aacgccccac gcggccctag ccccggtaat ggcgttaacc agggcgaaag
10801 gactagaggt tagaggagac ccgcggttt aaagtgcacg gcccagcctg gctgaagctg
10861 taggtcaggg gaaggactag aggttagtgg agacccccgtg ccacaaaaca ccacaacaaa
10921 acagcatatt gacacctggg atagactagg agatcttctg ctctgcacaa ccagccacac
10981 ggcacagtgc gccgacaatg gtggctggtg gtgcgagaac acaggatct
//
```

Complete Nucleotide Sequence of Fully-Infectious Lineage I WNV cDNA Clone of Strain 3356
*(Nucleotide positions different from FIG. 20 are shown in bold underline)*

FIG. 21 a

```
   1    agtagttcgc ctgtgtgagc tgacaaactt agtagtgttt gtgaggatta acaacaatta
  61    acacagtgcg agctgtttct tagcacgaag atctcgatgt ctaagaaacc aggagggccc
 121    ggcaagagcc gggctgtcaa tatgctaaaa cgcggaatgc cccgcgtgtt gtccttgatt
 181    ggactgaaga gggctatgtt gagcctgatc gacggcaagg gccaatacg atttgtgttg
 241    gctctcttgg cgttcttcag gttcacagca attgctccga cccgagcagt gctggatcga
 301    tggagaggtg tgaacaaaca aacagcgatg aaacaccttc tgagttttaa gaaggaacta
 361    gggaccttga ccagtgctat caatcggcgg agctcaaaac aaaagaaaag aggaggaaag
 421    accggaattg cagtcatgat tggcctgatc gccagcgtag gagcagttac cctctctaac
 481    ttccaaggga aggtgatgat gacggtaaat gctactgacg tcacagatgt catcacgatt
 541    ccaacagctg ctggaagaa cctatgcatt gtcagagcaa tggatgtggg atacatgtgc
 601    gatgatacta tcacttatga atgcccagtg ctgtcggctg gtaatgatcc agaagacatc
 661    gactgttggt gcacaaagtc agcagtctac gtcaggtatg gaagatgcac caagacacgc
 721    cactcaagac gcagtcggag gtcactgaca gtgcagacac acggagaaag cactctagcg
 781    aacaagaagg gggcttggat ggacagcacc aaggccacaa ggtatttggt aaaaacagaa
 841    tcatggatct tgaggaaccc tggatatgcc ctggtggcag ccgtcattgg ttggatgctt
 901    gggagcaaca ccatgcagag agttgtgttt gtcgtgctat tgcttttggt ggccccagct
 961    tacagcttca actgccttgg aatgagcaac agagacttct tggaaggagt gtctggagca
1021    acatgggtgg atttggttct cgaaggcgac agctgcgtga ctatcatgtc taaggacaag
1081    cctaccatcg atgtgaagat gatgaatatg gaggcggcca acctggcaga ggtccgcagt
1141    tattgctatt tggctaccgt cagcgatctc tccaccaaag ctgcgtgccc gaccatggga
1201    gaagctcaca tgacaaacg tgctgaccca gcttttgtgt gcagacaagg agtggtggac
1261    aggggctggg gcaacggctg cggaCtattt ggcaaggaa gcattgacac atgcgccaaa
1321    tttgcctgct ctaccaaggc aataggaaga accatcttga aagagaatat caagtacgaa
1381    gtggccattt ttgtccatgg accaactact gtggagtcgc acggaaacta ctccacacag
1441    gttggagcca ctcaggcagg gagattcagc atcactcctg cggcgccttc atacacacta
1501    aagcttggag aatatggaga ggtgacagtg gactgtgaac cacggtcagg gattgacacc
1561    aatgcatact acgtgatgac tgttggaaca aagacgttct tggtccatcg tgagtggttc
1621    atggacctca acctcccttg gagcagtgct ggaagtactg tgtggaggaa cagagagacg
1681    ttaatggagt ttgaggaacc acacgccacg aagcagtctg tgatagcatt gggctcacaa
1741    gagggagctc tgcatcaagc tttggctgga gccattcctg tggaatttc aagcaacact
1801    gtcaagttga cgtcgggtca tttgaagtgt agagtgaaga tggaaaaatt gcagttgaag
1861    ggaacaacct atggcgtctg ttcaaaggct ttcaagtttc ttgggactcc cgcagacaca
1921    ggtcacggca ctgtggtgtt ggaattgcag tacactggca cggatggacc ttgtaaagtt
1981    cctatctcgt cagtggcttc attgaacgac ctaacgccag tgggcagatt ggtcactgtc
2041    aaccctttg tttcagtggc cacggccaac gctaaggtcc tgattgaatt ggaaccaccc
2101    tttggagact catacatagt ggtgggcaga ggagaacaac agatcaatca ccattggcac
2161    aagtctggaa gcagcattgg caaagccttt acaaccaccc tcaaaggagc gcagagacta
2221    gccgctctag gagacacagc ttgggacttt ggatcagttg gagggtgtt caccctcagtt
2281    gggaaggctg tccatcaagt gttcggagga gcattccgct tactgttcgg aggcatgtcc
2341    tggataacgc aaggattgct ggggctctc ctgttgtgga tgggcatcaa tgctcgtgat
2401    aggtccatag ctctcacgtt tctcgcagtt ggaggagttc tgctcttcct ctccgtgaac
2461    gtgcacgctg acactgggtg tgccatagac atcagccggc aagagctgag atgtggaagt
2521    ggagtgttca tacacaatga tgtggaggct ggatggacc gatacaagta ttaccctgaa
2581    acgccacaag gcctagccaa gatcattcag aaagctcata aggaaggagt gtgcggtcta
2641    cgatcagttt ccagactgga gcatcaaatg tgggaagcag tgaaggacga gctgaacact
2701    cttttgaagg agaatggtgt ggaccttagt gtcgtggttg agaaacagga gggaatgtac
2761    aagtcagcac ctaaacgcct caccgccacc acggaaaaat tggaaattgg ctggaaggcc
2821    tggggaaaga gtattttatt tgcaccagaa ctcgccaaca cacctttgt ggttgatggt
2881    ccggagacca aggaatgtcc gactcagaat cgcgcttgga atagcttaga agtggaggat
2941    tttggatttg gtctcaccag cactcggatg ttcctgaagg tcagagagag caacacaact
3001    gaatgtgact cgaagatcat tggaacggct gtcaagaaca acttggcgat ccacagtgac
3061    ctgtcctatt ggattgaaag caggctcaat gatacgtgga gcttgaaag ggcagttctg
3121    ggtgaagtca aatcatgtac gtggcctgag acgcatacct gtgggcga tggaatcctt
3181    gagagtgact tgataatacc agtcacactg gcgggaccac gaagcaatca caatcgggaga
```

Complete Nucleotide Sequence f Fully-Infectious Lineage I WNV cDNA Cl ne of Strain 3356
*(Nucleotide positions different from FIG. 20 are shown in bold underline)*

FIG. 21 b

```
3241   cctgggtaca agacacaaaa ccagggccca tgggacgaag gccgggtaga gattgacttc
3301   gattactgcc caggaactac ggtcaccctg agtgagagct gcggacaccg tggacctgcc
3361   actcgcacca ccacagagag cggaaagttg ataacagatt ggtgctgcag gagctgcacc
3421   ttaccaccac tgcgctacca aactgacagc ggctgttggt atggtatgga gatcagacca
3481   cagagacatg atgaaaagac cctcgtgcag tcacaagtga atgcttataa tgctgatatg
3541   attgacccdtt ttcagttggg ccttctggtc gtgttcttgg ccacccagga ggtccttcgc
3601   aagaggtgga cagccaagat cagcatgcca gctatactga ttgctctgct agtcctggtg
3661   tttgggggca ttacttacac tgatgtgtta cgctatgtca tcttggtggg ggcagctttc
3721   gcagaatcta attcgggagg agacgtggta cacttggcgc tcatggcgac cttcaagata
3781   caaccagtgt ttatggtggc atcgtttctc aaagcgagat ggaccaacca ggagaacatC
3841   ttgttgatgt tggcggctgt tttctttcaa atggcttatc acgatgcccg ccaaattctg
3901   ctctgggaga tccctgatgt gttgaattca ctggcggtag cttggatgat actgagagcc
3961   ataacattca caacgacatc aaacgtggtt gttccgctgc tagccctgct aacacccggg
4021   ctgagatgct tgaatctgga tgtgtacagg atactgctgt tgatggtcgg aataggcagc
4081   ttgatcaggg agaagaggag tgcagctgca aaaaagaaag gagcaagtct gctatgcttg
4141   gctctagcct caacaggact tttcaacccc atgatccttg ctgctggact gattacatgt
4201   gatcccaacc gtaaacgcgg atggcccgca actgaagtga tgacagctgt cggcctgatg
4261   tttgccatcg tcggagggct ggcagagctt gacattgact ccatggccat tccaatgact
4321   atcgcgggc tcatgtttgc tgctttcgtg atttctggga aatcaacaga tatgtggatt
4381   gagagaacgg cggacatttc ctgggaaagt gatgcagaaa ttacaggctc gagcgaaaga
4441   gttgatgtgc ggcttgatga tgatggaaac ttccagctca tgaatgatcc aggagcacct
4501   tggaagatat ggatgctcag aatggtctgt ctcgcgatta gtgcgtacac ccctgggca
4561   atcttgccct cagtagttgg attttggata actctccaat acacaaagag aggaggcgtg
4621   ttgtgggaca ctccctcacc aaaggagtac aaaaaggggg acacgaccac cggcgtctac
4681   aggatcatga ctcgtgggct gctcggcagt tatcaagcag gagcgggcgt gatggttgaa
4741   ggtgttttcc acacccttg gcatacaaca aaaggagccg ctttgatgag cggagagggc
4801   cgcctggacc catactgggg cagtgtcaag gaggatcgac tttgttacgg aggaccctgg
4861   aaattgcagc acaagtggaa cgggcaggat gaggtgcaga tgattgtggt ggaacctggc
4921   aagaacgtta agaacgtcca gacgaaacca ggggtgttca aaacacctga aggagaaatc
4981   ggggccgtga ctttggactt ccccactgga acatcaggct caccaatagt ggacaaaaac
5041   ggtgatgtga ttgggctttta tggcaatgga gtcataatgc caacggctc atacataagc
5101   gcgatagtgc agggtgaaag gatggatgag ccaatcccag ccggattcga acctgagatg
5161   ctgaggaaaa aacagatcac tgtactggat ctccatcccg gcgccggtaa aacaaggagg
5221   attctgccac agatcatcaa agaggccata aacagaagac tgagaacagc cgtgctagca
5281   ccaaccaggg ttgtggctgc tgagatggct gaagcactga gaggactgcc catccggtac
5341   cagacatccg cagtgcccag agaacataat ggaaatgaga ttgttgatgt catgtgtcat
5401   gctaccctca cccacaggct gatgtctcct cacagggtgc cgaactacaa cctgttcgtg
5461   atggatgagg ctcatttcac cgacccagct agcattgcag caagaggtta catttccaca
5521   aaggtcgagc taggggaggc ggcggcaata ttcatgacag ccaccccacc aggcacttca
5581   gatccattcc cagagtccaa ttcaccaatt tccgacttac agactgagat cccggatcga
5641   gcttggaact ctggatacga atggatcaca gaatacaccg gaagacggt ttggtttgtg
5701   cctagtgtca agatggggaa tgagattgcc ctttgcctac aacgtgctgg aaagaaagta
5761   gtccaattga acagaaagtc gtacgagacg gagtacccaa aatgtaagaa cgatgattgg
5821   gactttgtta tcacaacaga catatctgaa atgggggcta actttaaggc gagcagggtg
5881   attgacagcc ggaagagtgt gaaaccaacc atcataacag aaggagaagg agagtgatc
5941   ctgggagaac catctgcagt gacagcagct agtgccgccc agagacgtgg acgtatcggt
6001   agaaatccgt cgcaagttgg tgatgagtac tgttatgggg ggcacgaa tgaagacgac
6061   tcgaacttcg cccattggac tgaggcacga atcatgctgg acaacatcaa catgccaaac
6121   ggactgatcg ctcaattcta ccaaccagag cgtgagaagg tatataccat ggatgggaa
6181   taccggctca gaggagaaga gagaaaaaac tttctggaac tgttgaggac tgcagatctg
6241   ccagtttggc tggcttacaa ggttgcagcg gctggagtgt cataccacga ccggaggtgg
6301   tgctttgatg gtccaggac aaacacaatt ttagaagaca caacgaagt ggaagtcatc
6361   acgaagcttg gtgaaaggaa gattctgagg ccgcgctgga ttgacgccag ggtgtactcg
```

Complete Nucleotide Sequence f Fully-Infectious Lineage I WNV cDNA Cl ne of Strain 3356
*(Nucleotide positions different from FIG. 20 are shown in bold underline)*

FIG. 21 c

```
6421  gatcaccagg cactaaaggc gttcaaggac ttcgcctcgg gaaaacgttc tcagataggg
6481  ctcattgagg ttctgggaaa gatgcctgag cacttcatgg ggaagacatg ggaagcactt
6541  gacaccatgt acgttgtggc cactgcagag aaaggaggaa gagctcacag aatggccctg
6601  gaggaactgc cagatgctct tcagacaatt gccttgattg ccttattgag tgtgatgacc
6661  atgggagtat tcttcctcct catgcagcgg aagggcattg gaaagatagg tttgggaggc
6721  gctgtcttgg gagtcgcgac cttttctgt tggatggctg aagttccagg aacgaagatc
6781  gccggaatgt tgctgctctc ccttctcttg atgattgtgc taattcctga gccagagaag
6841  caacgttcgc agacagacaa ccagctagcc gtgttcctga tttgtgtcat gacccttgtg
6901  agcgcagtgg cagccaacga gatgggttgg ctagataaga ccaagagtga cataagcagt
6961  ttgtttggc aaagaattga ggtcaaggag aatttcagca tgggagagtt tcttTtggac
7021  ttgaggccgg caacagcctg gtcactgtac gctgtgacaa cagcggtcct cactccactg
7081  ctaaagcatt tgatcacgtc agattacatc aacacctcat tgacctcaat aaacgttcag
7141  gcaagtgcac tattcacact cgcgcgaggc ttcccctcg tcgatgttgg agtgtcggct
7201  ctcctgctag cagccggatg ctggggacaa gtcaccctca ccgttacggt aacagcggca
7261  acactccttt tttgccacta tgcctacatg gttcccggtt ggcaagctga ggcaatgcgc
7321  tcagcccagc ggcggacagc ggccggaatc atgaagaacg ctgtagtgga tggcatcgtg
7381  gccacggacg tcccagaatt agagcgcacc acacccatca tgcagaagaa agttggacag
7441  atcatgctga tcttggtgtc tctagctgca gtagtagtga acccgtctgt gaagacagta
7501  cgagaagccg aattttgat cacggccgca gcggtgacgc tttgggagaa tggagcaagc
7561  tctgtttgga acgcaacaac tgccatcgga ctctgccaca tcatgcgtgg gggttggttg
7621  tcatgtctat ccataacatg gacactcata aagaacatgg aaaaaccagg actaaaaga
7681  ggtggggcaa aaggacgcac cttgggagag gtttggaaag aaagactcaa ccagatgaca
7741  aaagaagagt tcactaggta ccgcaaagag gccatcatcg aagtcgatcg ctcagcagca
7801  aaacacgcca ggaaagaagg caatgCcact ggagggcatc cagtctctag ggcacagca
7861  aaactgagat ggctggtcga acggaggttt ctcgaaccgg tcggaaaagt gattgacctt
7921  ggatgtggaa gaggcggttg gtgttactat atggcaaccc aaaaaagagt ccaagaagtc
7981  agagggtaca caaagggcgg tcccggacat gaagagcccc aactagtgca aagttatgga
8041  tggaacattg tcaccatgaa gagtggAgtg gatgtgttct acagaccttc tgagtgttgt
8101  gacaccctcc tttgtgacat cggagagtcc tcgtcaagtg ctgaggttga agagcatagg
8161  acgattcggg tccttgaaat ggttgaggac tggctgcacc gagggccaag ggaattttgc
8221  gtgaaggtgc tctgcccta catgccgaaa gtcatagaga gatggagct gctccaacgc
8281  cggtatgggg ggggactggt cagaaaccca ctctcacgga attccacgca cgagatgtat
8341  tgggtgagtc gagcttcagg caatgtggta cattcagtga atatgaccag ccaggtgctc
8401  ctaggaagaa tggaaaaaag gacctggaag ggaccccaat acgaggaaga tgtaaacttg
8461  ggaagtggaa ccagggcggt gggaaaaccc ctgctcaact cagacaccag taaaatcaag
8521  aacaggattg aacgactcag gcgtgagtac agttcgacgt ggcaccacga tgagaaccac
8581  ccatatagaa cctggaacta tcacggcagt tatgatgtga gcccacagg ctccgccagt
8641  tcgctggtca atggagtggt caggctcctc tcaaaaccat gggacaccat cacgaatgtt
8701  accaccatgg ccatgactga cactactccc ttcgggcagc agcgagtgtt caaagagaag
8761  gtggacacga aagctcctga accgccagaa ggagtgaagt acgtgctcaa cgagaccacc
8821  aactggttgt gggcgttttt ggccagagaa aaacgtccAa gGatgtgctc tcgagaggaG
8881  ttcataagaa aggtcaacag caatgcagct ttgggtgcca tgtttgaaga gcagaatcaa
8941  tggaggagcg ccagagaggc agttgaagat ccaaaatttt gggagatggt ggatgaggag
9001  cgcgaggcac atctgcgggg ggaatgtcac acttgcattt acaacatgat gggaaagaga
9061  gagaaaaaac ccggagagtt cggaaaggcc aagggaagca gagccatttg gttcatgtgg
9121  Tgctttctgga gttcgagggct ctgggttttc tcaatgaaga ccactggctt
9181  ggaagaaaga actcaggagg aggtgtcgag ggcttgggcc tccaaaaact gggttacatc
9241  ctgcgtgaag ttggcacccg gcctggggc aagatctatg ctgatgacac agctggctgg
9301  gacacccgca tcacgagagc tgacttggaa aatgaagcta ggtgcttga gctgcttgat
9361  ggggaacatc ggcgtcttgc cagggccatc attgagctca cctatcgtca caaagttgtg
9421  aaagtgatgc gcccggctgc tgatggaaga accgtcatgg atgttatctc cagagaagat
9481  cagagggga gtggacaagt tgtcacctac gccctaaaca ctttcaccaa cctggccgtc
9541  cagctggtga ggatgatgga aggaaga gtgattggcc cagatgatgt ggagaaactc
9601  acaaaaggga aaggacccaa agtcaggacc tggctgtttg agaatgggga agaaagactc
```

Complete Nucleotide Sequence of Fully-Infectious Lineage I WNV cDNA Clone of Strain 3356
*(Nucleotide positions different from FIG. 20 are shown in bold underline)*

FIG. 21 d

```
 9661 agccgcatgg ctgtcagtgg agatgactgt gtggtaaagc ccctggacga tcgctttgcc
 9721 acctcgctcc acttcctcaa tgctatgtca aaggttcgca aagacatcca agagtggaaa
 9781 ccgtcaactg gatggtatga ttggcagcag gttccatttt gctcaaacca tttcactgaa
 9841 ttgatcatga aagatggaag aacactggtg gttccatgcc gaggacagga tgaattggta
 9901 ggcagagctc gcatatctcc aggggccgga tggaacgtcc gcgacactgc ttgtctggct
 9961 aagtcttatg cccagatgtg gctgcttctg tacttccaca gaagagacct gcggctcatg
10021 gccaacgcca tttgctccgc tgtccctgtg aattgggtcc ctaccggaag aaccacgtgg
10081 tccatccatg caggaggaga gtggatgaca acagaggaca tgttggaggt ctggaaccgt
10141 gtttggatag aggagaatga atggatggaa gacaaaaccc cagtggagaa atggagtgac
10201 gtcccatatt caggaaaacg agaggacatc tggtgtggca gcctgattgg cacaagagcc
10261 cgagccacgt gggcagaaaa catccaggtg gctatcaacc aagtcagagc aatcatcgga
10321 gatgagaagt atgtggatta catgagttca ctaaagagat atgaagacac aactttggtt
10381 gaggacacag tactgtagat atttaatcaa ttgtaaatag acaatataag tatgcataaa
10441 agtgtagttt tatagtagta tttagtggtg ttagtgtaaa tagttaagaa aattttgagg
10501 agaaagtcag gccgggaagt tcccgccacc ggaagttgag tagacggtgc tgcctgcgac
10561 tcaaccccag gaggactggg tgaacaaagc cgcgaagtga tccatgtaag ccTtcagaac
10621 cgtctcggaa ggaggacccc acatgttgta acttcaaagc ccaatgtcag accacgctac
10681 ggcgtgctac tctgcggaga gtgcagtctg cgatagtgcc ccaggaggac tgggttaaca
10741 aaggcaaacc aacgccccac gcggccctag ccccggtaat ggTgttaacc agggcgaaag
10801 gactagaggt tagaggagac cccgcggttt aaagtgcacg gcccagcctg gctgaagctg
10861 taggtcaggg gaaggactag aggttagtgg agaccccgtg ccacaaaaca ccacaacaaa
10921 acagcatatt gacacctggg atagactagg agatcttctg ctctgcacaa ccagccacac
10981 ggcacagtgc gccgacaatg gtggctggtg gtgcgagaac acaggatct
//
```

SCREENING FOR WEST NILE VIRUS ANTIVIRAL THERAPY

REFERENCE TO RELATED APPLICATIONS/INCORPORATION BY REFERENCE

A claim of priority is made to U.S. Provisional Application No. 60/427,117, filed Nov. 18, 2002. Each of the documents cited herein (herein cited documents), and each of the documents cited in each of the herein cited documents, together with any manufacturer's specifications, data sheets, descriptions, product literature, instructions and the like for any products mentioned herein or in herein cited documents or in documents cited in herein cited documents, is hereby incorporated herein by reference. None of the documents incorporated by reference into this text is admitted to be prior art with respect to the present invention, but, documents incorporated by reference into this text may be employed in the practice of the invention.

FIELD OF THE INVENTION

The instant invention relates generally to the field of antiviral chemotherapeutics and vaccines for the treatment and/or immunization against flaviviral infections. More in particular, this invention relates to compositions and methods for the identifying novel chemotherapeutics effective against flaviviral infections, such as, WNV, JEV, SLEV, AV, KV, JV, CV, YV, TBEV, DENV-1, DENV-2, DENV-3, DENV-4, YFV and MVEV, and other presently known or emerging flaviviruses. Still further, the present invention relates to screening assays, in particular, high throughput screening assays involving recombinant WNV full-length cDNA clones and WNV replicon systems engineered with reporter-encoding nucleotide sequences, for the screening and identification of novel anti-flavivirus inhibitors and/or chemotherapeutics. The present invention also relates to compositions and methods for the construction of novel attenuated WNV derivatives to be used as vaccines to immunize against infection by a flavivirus, such as WNV, JEV, SLEV, AV, KV, JV, CV, YV, TBEV, DENV-1, DENV-2, DENV-3, DENV-4, YFV and MVEV, and other presently known or emerging flaviviruses.

BACKGROUND OF THE INVENTION

The increasingly frequent outbreaks of infections by West Nile Virus (WNV) and other related flaviviruses in humans, as well as their recent categorization by the Centers for Disease Control and Prevention (CDC) as potential bioterrorism pathogens, have underscored the global public health need for effective antiviral chemotherapeutics and vaccines. Flavivirus infections are a global public health problem with about half of the flaviviruses causing human diseases (C. G. Hayes, in *The Arboviruses: Epidemiology and Ecology*, T. P. Monathy, ed., CRC, Boca Raton, Fla., vol. 5, chap. 49 (1989); M. J. Cardosa, *Br Med Bull,* 54, pp. 395-405 (1998); Z. Hubalek and J. Halouzka, *Emerg Infect Dis,* 5, pp. 643-50 (1999)). These viruses are normally maintained in a natural cycle between mosquito vectors and birds, whereas humans and equine are considered dead-end hosts. Birds, including the American crow, *Corvus brachyrhynchos,* can serve as non-human reservoirs for the virus. In the case of WNV, the viruses are transmitted to man by mosquitoes and in the Northeastern United States these mosquito vectors are primarily of the genera *Culex* and *Aedes,* in particular *C. pipiens* and *A. vexans.*

West Nile virus and other related flaviviruses are classified within the family Flaviviridae, genus *Flavivirus,* and belong to the Japanese Encephalitis antigenic complex of viruses. In addition to WNV, this flavivirus sero-complex includes Japanese encephalitis virus (JEV), St. Louis encephalitis (SLEV), Alfuy virus (AV), Koutango virus (KV), Kunjin virus (JV), Cacipacore virus (CV), Yaounde virus (YV), and Murray Valley encephalitis virus (MVEV). The Flaviviridae family also includes the Tick-borne encephalitis virus (TBEV), Dengue virus (including the four serotypes of: DENV-1, DENV-2, DENV-3, and DENV-4), and the family prototype, Yellow Fever virus (YFV).

Flaviviruses are the most significant group of arthropod-transmitted viruses in terms of global morbidity and mortality. A combined toll of hundreds of millions of infections around the world annually coupled with the lack of sustained mosquito control measures, has distributed flaviviruses throughout the tropics, subtropics, and temperate areas. As a result, over half the world's population is at risk for flaviviral infection. Further, modern jet travel and human migration have raised the potential for global spread of these pathogens.

WNV was originally isolated in 1937 from the blood of a febrile woman from Uganda's West Nile province and was subsequently found in many regions, including Africa, the Middle East, Europe, Russia, India and Indonesia. Most recently, WNV has appeared in North America, beginning with a 1999 outbreak in the New York City area.

Since 1996, WNV outbreaks have frequently occurred in humans and horses, including in Romania and Morocco in 1996; Tunisia in 1997; Italy in 1998; Israel, Russia and the U.S. in 1999; Israel, France and the U.S. in 2000; and Israel and the U.S. in 2001. Severe human disease associated with WNV infection has been reported worldwide, with 393 cases in 1996 in Romania; 942 cases in 1999 in Volgograd, Russia; and 2,417 and 45 cases in 1999 in Israel in 2000 and 2001, respectively. Since its appearance in northeastern U.S. in 1999, WNV has caused significant human, equine and avian disease, and has quickly spread from the Northeast to the eastern seaboard, to the Midwest, and most recently to the Deep South. There were 61 human cases (7 deaths) in New York City in 1999; 21 human cases (4 deaths) in New York, New Jersey and Connecticut in 2000; and 48 human cases (5 deaths) in New York, Florida, New Jersey, Connecticut, Maryland, Massachusetts, Georgia and Louisiana in 2001. As of Sep. 13, 2002, 1438 human cases (64 deaths) for year 2002 have been reported in over 30 states in the U.S. These data clearly indicate that human outbreaks of WNV pose a severe threat to public health.

Strains of WNV are categorized into two different phylogenetic lineages, namely, lineage I and II, which share 75% nucleotide sequence identity (Lanciotti, R et al, (2002) Virology 298:96-105). Lineage I strains have been isolated from human and equine epidemic outbreaks from around the world and constitute the main form of human pathogen. Sequence analysis indicates that the current epidemic strain in North America belongs to lineage I. Lineage II strains are rarely isolated from humans and are geographically restricted primarily to sub-Saharan Africa and Madagascar. The differences in disease patterns of lineage I and II strains are postulated to be the result of differences in vector competence (host compatibility), virulence, and transmission cycles of the strains, as well as, host immunity (Beasley, D. W. C. et al, (2001) International Conference on the West Nile Virus, New York Academy of Science Poster Section 1:5). Sequence analysis showed that the strain in North America is closely related to other human epidemic strains isolated from Israel, Romania, Russia, and France, all of which belong to lineage I (Lanciotti, R. et al. (1999) Science 286:2333-2337).

The flavivirus genome, including the genome of WNV, is a single positive-sense RNA of approximately 10,500 nucleotides containing short 5' and 3' untranslated regions (UTR), a single long open reading frame (ORF), a 5' cap region, and a non-polyadenylated 3' terminus. The entire genome is transcribed as a single polycistronic messenger RNA molecule, which is then translated as a polyprotein. Individual proteins are subsequently produced by proteolytic processing of the polyprotein, which is directed by viral and host cell proteases (Chambers, T. J. et al, (1990) Ann. Rev. Microbiol. 44: 649-688; Lindenbach, B. D. and C. M. Rice, (2001) In D. M. Knipe and P. M. Howley (ed), Fields virology, $4^{th}$ ed., vol. 1. Lippincott Williams & Wilkins, Philadelphia, Pa.).

During the replication cycle of flaviviruses, especially WNV, synthesis of positive and negative (hereafter referred to as plus (+) and minus (-), respectively) sense RNAs is asymmetric. In the case of WNV, plus-sense RNAs are produced in 10- to 100-fold excess over minus-sense RNA. Regulatory sequences in the 3' UTR are believed to function as a promoter for initiation of minus-strand RNA synthesis. Deletion of this region ablates viral infectivity (Brinton, M. A. et al, (1986) Virology 162: 290-299; Proutski, V., et al (1997) Nucleic Acids Res. 25: 1194-1202; Rauscher, S., et al (1997) RNA 3: 779-791).

With respect to the flavivirus genome, two distinct classes of genes are found which encode either structural or non-structural proteins. There are three structural proteins, which include capsid (C), membrane (M) or premembrane (prM), and envelope (E) glycoprotein. The E glycoprotein and M proteins are found on the surface of the virion where they are anchored in the membrane. Mature E glycoprotein is glycosylated, whereas M is not, although its precursor, prM, is a glycoprotein. In addition, there are seven non-structural proteins, which are denoted as NS1 (non-structural protein 1), NS2A, NS2B, NS3, NS4A, NS4B, and NS5. NS1 and NS2A correspond to a glycoprotein, NS2B corresponds to a protease cofactor, NS3, NS4A, and NS4B correspond to a protease and a helicase, and NS5 corresponds to a viral RNA-dependent RNA polymerase. In addition to these ten genes, regulatory elements in the 5' and 3' UTRs are also required for proper replication and packaging of the virions. The 5' and 3' UTRs, which are approximately 100 and 400-700 nucleotides in length, respectively, form highly conserved secondary and tertiary structures, conferring specificity in binding of host proteins such as the eukaryotic translation elongation factor, eF1-α (Blackwell, J. L., and M. A. Brinton, (1995) J. Virol. 69: 5650-5658; Blackwell, J. L., and M. A. Brinton, (1997) J. Virol. 71: 6433-6444).

The current global risk for flaviviral infections, the rapid and recent spread of WNV in the Western Hemisphere, and the recent CDC prioritization of WNV, together with DENV, JEV and YFV, as potential bioterrorism pathogens, highly stresses the need for anti-flaviviral treatments, such as vaccines and anti-flaviviral inhibitors. With the exception of a limited number of vaccines available for specific flavivirus infections, such as vaccines for YFV, TBEV, and JEV, effective vaccines and/or anti-flaviviral therapies for use in humans are not generally available for flavivirus infections, especially WNV and DENV. Thus, new effective vaccines and/or anti-flaviviral therapies for the immunization and/or treatment of flavivirus infections, especially WNV and DENV, in humans are urgently needed and would be an advance in the art.

Specifically, in the case of WNV, there are no vaccines or effective anti-WNV therapies, inhibitors, medications, or cures available for the immunization against or the treatment of WNV infections. To prevent WNV infection in humans, mosquito control and public awareness programs aimed at reducing exposure to mosquito bites are often deployed. The efficacy and the cost-effectiveness of these prevention measures are, however, compromised by the sporadic nature of human WNV epidemics. Further, mosquito control programs, such as, insecticide spraying, are difficult, potentially toxic to humans, and require repeated application. Further, insecticide spraying does not provide complete coverage of mosquito breeding areas or eradiction of mosquitoes.

Currently, the only way of treating WNV infection is to treat the symptoms of infection. Symptoms are highly variable and generally occur 5-15 days following the bite of an infected mosquito. Some infected persons may have no noticeable symptoms or may experience only mild illness, such as a slight fever, headache, rash, swollen nodes and conjunctivitis, before fully recovering. However, in other infected persons, particularly the elderly, WNV can cause serious disease that may include a rapid onset of severe headache, high fever, stiff neck, disorientation, and muscle weakness. At the most severe level, WNV infection can cause permanent neurological damage, such as with encephalitis or meningitis, and can be fatal. Treatment is supportive, often involving hospitalization, intravenous fluids, respiratory support, and prevention of secondary infections for patients with severe disease.

Similarly, in the case of DENV, there are no effective vaccines and/or antiviral therapies available. Over 2.5 billion people worldwide live in areas at risk of DENV infection, and 100 million people are affected annually. Classic dengue fever is characterized by acute onset of high fever, frontal headache, retro-orbital pain, nausea, vomiting, and often a maculopapular rash. In addition, many patients may notice a change in taste sensation. Symptoms tend to be milder in children than in adults, and the illness may be clinically indistinguishable from influenza, measles, or rubella. The disease manifestations can range in intensity from inapparent illness to the symptoms described. The acute phase of up to 1 week is followed by a 1- to 2-week period of convalescence which is characterized by weakness, malaise, and anorexia. In leiu of a vaccine and/or anti-DENV chemotherapeutics, the only available treatments emphasize relief of the disease symptoms and can include fluid replacement and acetaminophen administration. Development of a DENV vaccine has long been unsuccessful principally because of the need to simultaneously immunize and induce long-lasting protection against all four DENV serotypes (DENV-1, -2, -3, and -4). An incompletely immunized individual may be sensitized to dengue hemorrhagic fever or dengue shock syndrome.

As outlined above, effective chemotherapeutics to treat WNV and DENV and other emerging flaviviruses are urgently needed. Although a limited number of inhibitors of flaviviruses have been identified, many of these have severe side effects, are not specific to flaviviruses, and are not known to be clinically effective and/or useful. For example, recent evidence suggested the use of nucleoside analogs as potential inhibitors of flaviviruses. Specific examples include inhibitors of orotidine monophosphate decarboxylase, inosine monophosphate dehydrogenase, and CTP synthetase. Although it appeared that these inhibitors may have been effective in virus infected Vero cells, their effectiveness in humans or animals (i.e., in vivo) is not known. Additionally, as these nucleoside analogs are broad-spectrum inhibitors of purine and pyrimidine biosynthesis, the occurrence of side effects and lack of flaviviral specificity would further limit their usefulness in a clinical setting.

Another nucleoside analog, the drug Ribavirin, was found to have some activity against WNV in vitro when administered in combination with interferon alpha-2b. However, the drug combination has not been shown to be effective in humans. Similarly, inhibitors to other protein activities of the viral genome, such as the helicase and protease activities encoded by NS3, have been explored; however, their clinical significance is unknown since their anti-WNV activities have not been tested in vivo. Finally, inhibitors of viral glycoprotein processing have been studied, but the prevalence of side effects due to inhibition of N-linked glycosylation, as well as difficulty in achieving therapeutic serum concentration levels, limit the usefulness of this type of compound. Thus, although there are a small number of known inhibitors for flaviviruses, none have been shown to be effective in humans. Accordingly, novel anti-flavivirus chemotherapies and/or improvements in the effectiveness, specificity, and clinical utility of known flavivirus chemotherapies, would be an advance in the art.

As detailed above, the development of therapeutic drugs and/or vaccines to treat and/or immunize against WNV, DENV and other emerging flavivirus infections is urgently needed and of great importance to global public health. To achieve this goal, it is essential to develop high-throughput screening assays to facilitate the identification of novel chemotherapeutics effective against flaviviruses or vaccines capable of establishing a protective immune response to flaviviruses. Two general strategies to be adapted for the screening and identification of novel chemotherapeutic anti-flaviviral compounds and/or vaccines are based on biochemical and genetic approaches.

Assays for screening antiviral compounds that are based on biochemical approaches typically involve testing compounds for activities that limit or inhibit viral enzymes or proteins that are essential for viral propagation. For example, NS3, which has protease, helicase and NTPase activity, and NS5, which has an RNA-dependent RNA polymerase and methyltransferase activity, are key components of viral replication complex and thus, are ideal targets for antiviral screening. Further, three-dimensional structures of viral proteins, if available, can afford the possibility for rational design of drugs that will inhibit their activity, i.e., designing drugs based on the knowledge of the structure and shape of the active sites of the protein. For example, the crystal structures of the DENV NS3 protease domain and NS5 cap methyltransferase fragment have been solved and thus, the possibility of rationally designing small molecules to inhibit the active sites of NS3 and NS5 is feasible. Although biochemical approaches are capable of identifying potential viral inhibitors, they are limited in their overall efficiency since only a single enzyme or protein can be tested for any potential assay. Thus, individual assays would be required to screen for inhibitors of each given viral target protein.

In contrast, assays utilizing a genetic approach, which are usually cell-based, offer a number of advantages over biochemical approaches. One major advantage of a genetic approach based assay is that multiple viral protein targets can be analyzed simultaneously. A second major advantage is that, since genetic assays involve the use of living cells and the uptake of compounds therein, the screening assay is administered in a more authentic therapeutic environment. Accordingly, inhibitors identified through cell-based assays typically have a higher success rate in subsequent animal experiments.

Currently, there is only one type of cell-based assay available for screening for flaviviral inhibitors. The assay involves the infection of cultured cells with virus and the subsequent monitoring for potential inhibition in the presence of a potential inhibitor through observation or quantification of cytopathic effects (J. D. Morrey et al., Antiviral Res (2002) 55:107-116; I. Jordan, J. Infect. Dis. (2000) 182:1214-1217) or quantification of viral RNA by reverse transcriptase (RT)-PCR(S. F. Wu, J. Virol. (2002) 76:3596-3604). These assays are highly labor-intensive and impossible to use when screening compound libraries in large quantities. Thus, there is an urgent need in the art to develop reliable, high-throughput cell-based assays for the rapid screening and identification of potential inhibitors from compound libraries. Towards this endeavor, "reverse genetics systems", which are cDNA clones of RNA viruses, can be developed and used for genetic cell-based screening assays. For example, two kinds of reverse genetics systems, full-length infectious cDNA clones and replicons, have been developed for a number of flaviviruses (A. A. Khromykh, et al., J. Virol. (1997) 71:1497-1505; M. S. Campbell, et al., Virol. (2000) 269:225-237; R. J. Hurrelbrink, et al., J. Gen. Virol. (1999) 80:3115-3125; M. Kapoor, et al., Gene (1995) 162:175-180; A. A. Khromykh et al., J. Virol. (1994) 68:4580-4588; C. J. Lai et al., Proc. Natl. Acad. Sci. U.S.A. (1991) 88:5139-5143; C. W. Mandl et al., J. Gen. Virol. (1997) 78:1049-1057; C. M. Rice et al., Science (1985) 229:726-733; H. Sumiyoshi et al., J. Virol. (1992) 66:5425-5431; S. Polo et. al., J. Virol. (1997) 71:5366-5374), including lineage II WNV (V. F. Yamshchikov et al., Virology (2001) 281:294-304). Reporter genes can be engineered into the reverse genetics systems to allow for the monitoring of viral replication levels in the presence of potential inhibitors. However, there have been no reverse genetics systems developed for lineage I WNV strains, which comprise the main pathogen strains involved in human and equine outbreaks, such as the recent 1999 U.S. epidemic. For the purposes of drug screening it would be preferable to use human epidemic-causing lineage I strains for assay setup to ensure that the identified compounds have a direct relevance to human disease. Thus, there is an urgent need in the art for reverse genetics systems based on lineage I WNV for use in the identification of novel anti-WNV chemotherapeutics and vaccines.

Therefore, as detailed above, in addition to the need in the art for novel vaccines and/or anti-flaviviral therapies to immunize against and/or treat infections by WNV and other emerging flaviviruses and members of the flavivirus serocomplex, such as JEV, SLEV, AV, KV, JV, CV, YV, TBEV, DENV-1, DENV-2, DENV-3, DENV-4, YFV and MVEV. There is also an urgent need in the art for new methods of identifying potential chemotherapeutic therapies and vaccines, particularly high-throughput screening assays using genetic approaches to identify inhibitors and vaccines of lineage I WNV and other emerging flaviviruses and members of the flavivirus sero-complex, such as JEV, SLEV, AV, KV, JV, CV, YV, TBEV, DENV-1, DENV-2, DENV-3, DENV-4, YFV and MVEV.

OBJECTS AND SUMMARY OF THE INVENTION

Therefore, it can be an object of the present invention to provide novel antiflaviviral chemotherapeutic drugs and vaccines to be used to specifically treat or immunize against infections by a flavivirus, such as WNV, JEV, SLEV, AV, KV, JV, CV, YV, TBEV, DENV-1, DENV-2, DENV-3, DENV-4, YFV and MVEV and other currently known or emerging flaviviruses.

Another object of the present invention can be to provide a novel high-throughput screening assay utilizing a novel recombinant lineage I WNV cDNA clone, engineered with at least one reporter gene, to identify new chemotherapeutic therapies and vaccines to be used to treat and/or immunize against infections by a flavivirus, e.g., WNV, JEV, SLEV, AV, KV, JV, CV, YV, TBEV, DENV-1, DENV-2, DENV-3, DENV-4, YFV and MVEV and other known or emerging flaviviruses.

A further object of the present invention can be to provide a novel high-throughput screening assay utilizing a novel recombinant lineage I WNV replicon system, engineered with at least one reporter gene, to identify new chemotherapeutic therapies to be used to treat infections by a flavivirus, e.g., WNV, JEV, SLEV, AV, KV, JV, CV, Yv, TBEV, DENV-1, DENV-2, DENV-3, DENV-4, YFV and MVEV and other known or emerging flaviviruses.

Yet another object of the present invention can be to provide methods for making a cell line comprising a stably-replicating lineage I WNV replicon system engineered with at least one reporter gene to be used in a cell-based high-throughput screening assay to identify new chemotherapeutic therapies to be used to treat infections by a flavivirus, e.g., WNV, JEV, SLEV, AV, KV, JV, CV, YV, TBEV, DENV-1, DENV-2, DENV-3, DENV-4, YFV and MVEV and other known or emerging flaviviruses.

Still another object of the present invention can be to provide a method of deriving an attenuated lineage I WNV vaccine from a fully infectious lineage I WNV cDNA operably linked to at least one reporter gene, wherein the attenuated lineage I WNV is equally immunogenic but less virulent than the parental WNV and is capable of providing a protective immune response against a flavivirus, e.g., WNV, JEV, SLEV, AV, KV, JV, CV, YV, TBEV, DENV-1, DENV-2, DENV-3, DENV-4, YFV and MVEV and other known or emerging flaviviruses. The term "operably linked" means that the components described are in a relationship permitting them to function in their intended manner.

An even further object of the present invention can be to provide a pharmaceutical composition comprising an attenuated lineage I WNV that is equally immunogenic but less virulent than the parental WNV to provide a protective immune response against a flavivirus, e.g., WNV, JEV, SLEV, AV, KV, JV, CV, YV, TBEV, DENV-1, DENV-2, DENV-3, DENV-4, YFV and MVEV and other known or emerging flaviviruses.

A yet further object of the present invention can be to provide a novel fully-infectious lineage I WNV cDNA clone containing one or more genetic markers to enable one to distinguish between parental WNV and the fully-infectious lineage I WNV cDNA clone.

And, another object of the present invention can be to provide a novel reverse genetics system, comprising either a recombinant fully-infectious lineage I WNV cDNA clone or a lineage I WNV replicon system each engineered with at least one reporter gene, for the screening and identification of derivatives of previously-known antiflaviviral inhibitors having increased effectiveness against infections by a flavivirus, e.g., WNV, JEV, SLEV, AV, KV, JV, CV, Yv, TBEV, DENV-1, DENV-2, DENV-3, DENV-4, YFV and MVEV and other known or emerging flaviviruses.

The present invention is directed to novel genetically engineered WNV constructs, methods for rapidly identifying novel antiflaviviral chemotherapeutics and/or attenuated virus vaccines using genetically engineered WNV constructs, cell lines stably containing the genetically engineered WNV constructs for use in the high-throughput screening assays, and pharmaceutical compositions comprising an attenuated WNV effective to immunize against infections by a flavivirus, e.g., WNV, JEV, SLEV, AV, KV, JV, CV, Yv, TBEV, DENV-1, DENV-2, DENV-3, DENV-4, YFV and MVEV and other known or emerging flaviviruses.

More specifically, the present invention relates to novel lineage I WNV reverse genetics systems, and methods for making the reverse genetics systems, specifically, a fully-infectious lineage I WNV cDNA or replicon system engineered with one or more reporter genes to be used in high-throughput cell-based screening assays for the identification of novel antiflaviviral chemotherapeutics and/or vaccines effective to treat and/or immunize against infections by a flavivirus, e.g., WNV, JEV, SLEV, AV, KV, JV, CV, YV, TBEV, DENV-1, DENV-2, DENV-3, DENV-4, YFV and MVEV and other emerging flaviviruses.

The present invention further relates to high-throughput methods for screening compounds for antiflaviviral properties or improved derivatives thereof using novel lineage I WNV reverse genetics systems and/or cell lines stably containing the reverse genetics systems.

Also within the scope of the present invention is a pharmaceutical composition comprising an attenuated lineage I WNV that is less virulent but similarly immunogenic as the parent WNV and is capable of providing a protective immune response in a host.

The instant invention relates to reverse genetics system for screening and identifying antiflaviviral compounds. The invention also relates to a reverse genetics system for screening and identifying attenuated flaviviral vaccines. The reverse genetics systems of the present invention can be a full-length lineage I WNV cDNA clone and a lineage I WNV replicon system. The reverse genetics systems of the present invention can have a first reporter gene that can include a luciferase gene, a green fluorescent protein gene, beta-galactosidase gene, an oxidase gene, a peptidase gene, a glycosidase gene, a phosphatase gene, a fluorescent protein gene, and an antibiotic resistance gene. The reverse genetics systems can also include a second reporter gene which can be a selectable marker, such as neomycin resistance marker for selection of cells carrying the reverse genetics systems.

The present invention also relates to a method for preparing a fully-infectious RNA transcript from the reverse genetics systems of the invention, comprising the step of contacting the reverse genetics system with an DNA-dependent RNA polymerase that recognizes the promoter sequence operably linked to the WNV cDNA under conditions sufficient for transcription to occur. One of ordinary skill in the art will appreciate that the specific DNA-dependent RNA polymerase used depends on the promoter present which controls the transcription of the WNV genome. For example, if the T7 promoter is used to control the transcription of the WNV genome, then the T7 DNA-dependent RNA polymerase would be used to carry out transcription. Such RNA polymerases can be obtained from commercial sources, such as from NEW ENGLAND BIOLABS, INC. (MA) or PROMEGA CORPORATION (WI). The transcription reaction preferably is carried out in vitro. Further details on carrying out in vitro transcription reactions can be found in Maniatis et al., Molecular Cloning:

A Laboratory Manuel or another widely-used molecular biology handbook well-known to those in the art.

Also within the scope of the invention is a method for preparing a cell line stably replicating the reverse genetics systems of the invention, such as the lineage I WNV full-length cDNA clone and the lineage I WNV replicon system, comprising the steps of: (a) transfecting a cell host with the reverse genetics systems of the invention, and (b) selecting for cells resistant to an antibiotic.

The instant invention also relates to recombinant plasmids containing cDNA sequences corresponding to WNV lineage I, wherein said sequences comprise regions necessary for replication of the viral genome, a promoter sequence effective to control cDNA transcription, and exogenous sequences expressed concomitant with replication of the viral genome. The recombinant plasmids of the invention can carry the lineage I WNV replicon or the lineage I full-length cDNA clone.

The present invention further relates to a method of identifying potential antiflaviviral chemotherapeutics (i.e. antiflaviviral inhibitors) comprising the steps of: (a) contacting a cell line with a replicating reverse genetics system of the invention, such as a lineage I WNV replicon or a lineage I full-length WNV cDNA clone engineered with at least one reporter gene, with a potential chemotherapeutic compound, followed by measuring the level of expression of the reporter gene, wherein a reduced expression level of the reporter gene indicates a potential antiflaviviral chemotherapeutic.

The instant invention also contemplates the collecting, acquiring, transmitting, and providing to a third party any data or information obtained from the methods of the present invention, such as the methods to identify an antiflaviviral inhibitor using the reverse genetics systems of the invention.

Also contemplated by the present invention are any antiflavivirus inhibitors or antiflavivirus chemotherapeutics identified by the methods of the present invention, such as the screening methods using the reverse genetics systems of the present invention, especially the lineage I WNV replicon system and the lineage I full-length cDNA clone engineered with at least one nucleotide sequence encoding a reporter gene. The inhibitors can be provided as pharmaceutical compositions.

The instant invention also contemplates a method for generating a potential attenuated flavivirus vaccine, especially a vaccine for WNV, comprising the steps of: (a) mutating a sequence of the lineage I full-length fully-infectious WNV cDNA clone engineered with at least one reporter gene, (b) expressing the WNV cDNA clone in a host cell, and (c) detecting a decrease in reporter gene expression, wherein detecting a decrease in reporter gene expression indicates a potential attenuated WNV vaccine. The vaccine is contemplated for use in providing a protective immune response in a host, such as a human, animal, horse, bird, cat, dog, etc., for a flavivirus, such as, for example WNV, JEV, SLEV, AV, KV, JV, CV, YV, TBEV, DENV-1, DENV-2, DENV-3, DENV-4, YFV and MVEV and other emerging flaviviruses. The mutated sequence can include a portion of the regulatory sequences located at the 3' end of a WNV cDNA clone.

The present invention also contemplates any method for treating a flavivirus infection using the flavivirus inhibitors or pharmaceutical compositions of the invention, wherein the flavivirus may include, but is not limited to, WNV, JEV, SLEV, AV, KV, JV, CV, YV, TBEV, DENV-1, DENV-2, DENV-3, DENV-4, YFV and MVEV and other emerging flaviviruses. The invention also relates to any method to vaccinate or provide a protective immune response to a host, such as a human, animal, horse, bird, cat, dog, etc. using the flavivirus vaccines of the invention.

The instant invention further relates to a DNA molecule comprising a DNA sequence encoding a mRNA of a lineage I WNV genome, said DNA sequence having a 5' and a 3' end, said DNA molecule adapted to report the transcription of said DNA sequence, said DNA molecule comprising: (a) a deletion in said DNA sequence corresponding to one or more structural genes of said lineage I WNV genome; (b) a promoter at said 5' end of said DNA sequence; (c) a reporter gene at said 3' end of the DNA sequence; wherein said promoter is operably linked and adapted to control the transcription of said DNA sequence and said reporter gene.

The present invention also contemplates a DNA molecule comprising a DNA sequence encoding a full-length and fully-infectious mRNA of a lineage I WNV genome, said DNA sequence having a 5' and a 3' end, said DNA molecule adapted to report the transcription of said DNA sequence, said DNA molecule comprising: (a) a promoter at said 5' end of said DNA sequence; and (b) a reporter gene at said 3' end of the DNA sequence; wherein said promoter is adapted to control the transcription of said DNA sequence and said reporter gene.

The invention also relates to a method for screening a plurality of compounds comprising at least one flavivirus inhibitor to detect and identify said flavivirus inhibitor, comprising the steps: (a) providing a cell line comprised of cells each comprising a flavivirus reverse genetics system engineered with a least one fluorescence reporter gene; (b) detecting a first relative fluorescence signal of said cells; (c) contacting in a reaction well said cells with said plurality of compounds; (d) incubating the cells to allow said plurality of compounds to penetrate the cells; (e) detecting a second relative fluorescence signal of said cells; and (f) comparing the first and second relative fluorescence signals; wherein a lower second relative fluorescence signal indicates the presence of a flavivirus inhibitor.

Also contemplated by the instant invention is a high throughput assay for screening a plurality of compounds comprising at least one flavivirus inhibitor to detect and identify said flavivirus inhibitor, comprising the steps: (a) providing a cell line comprising cells each comprising the lineage I WNV replicon of claim 60; (b) detecting a first relative fluorescence signal of said cells; (c) contacting in a reaction well said cells with said plurality of compounds; (d) incubating the cells to allow said plurality of compounds to penetrate the cells; (e) detecting a second relative fluorescence signal of said cells; and (f) comparing the first and second relative fluorescence signals; wherein a lower second relative fluorescence signal indicates the presence of a flavivirus inhibitor.

Throughout this specification and claims, the word "comprise," or variations such as "comprises" or "comprising," will be understood to imply the inclusion of a stated integer or group of integers but not the exclusion of any other integer or group of integers.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference.

FIG. 1 illustrates the construction scheme of the full-length lineage I WNV cDNA clone. Genome organization and unique restriction sites as well as their nucleotide numbers are shown at the top of the figure. The nucleotide sequence of the parental full-length lineage I WNV strain 3356 (GenBank accession No. AF404756) is set forth in FIG. 20 (SEQ ID NO. 1).

FIG. 2 compares the sequences of the full-length lineage I WNV cDNA clone and the parental WNV strain 3356 (GenBank accession No. AF404756).

FIG. 7 shows the similar growth kinetics of recombinant and parental WNV in two different cell lines. The growth kinetics of recombinant and parental viruses was compared at high and low multiplicity-of-infections (MOIs) on BHK-21 or *Aedes albopictus* C6/36 cells ("C6/36 cells"). Growth in BHK-21 cells is compared in (A). Growth in C6/36 cells is compared in (B). Viruses were inoculated at an MOI of 5.0 (filled symbols) or an MOI of 0.05 (open symbols) in triplicate in 12-well plates. Recombinant virus is designated by squares along a solid line. Parental virus is designated by triangles along a dashed line. Error bars represent +/− standard deviation of triplicate wells. Dotted line indicates the limit of detection of 500 PFU/ml.

FIG. 9 shows the strategy of replicon RNA transcription (A) and electrophoretic analysis of full length WNV genome RNA compared with the replicon variants (B). Transcription of WNV replicon plasmids was designed to produce replicon RNA with an authentic 3' viral end and an extra nonviral guanine at the 5' end. Formaldehyde denaturing agarose gel electrophoresis compares the mobility of full length WNV genomic transcripts to transcribed replicons.

FIG. 12 demonstrates that RNA replication in cells transfected with the replicon system is not derived from parental viral contamination. (A) shows a diagram of fragments generated from RT-PCR, followed by restriction analysis, between parental virus and replicon RNA. Agarose electrophoresis shown in (B) depicts restricted fragment sizes consistent with expected fragment sizes depicted in (A). As a negative control, RNA corresponding to a replicon containing a 3' UTR deletion was used. The 1-kb plus ladder was used as a standard.

FIG. 15 shows selection of cells containing persistently replicating WNV replicons. BHK-21 cells were transfected with NeoRep and selected by G418 resistance. The resulting cells were subjected to IFA to monitor viral protein expression and monitored for CPE by phase contrast or differential interference contrast (DIC) microscopy. (A) shows cells that were cultured in the absence of G418 selection. (B) shows cells that were cultured in the presence of G418 for 15 days (passage 2) and 40 days (passage 8), demonstrating persistent expression of viral proteins and lack of apparent morphological changes.

FIG. 20 shows the nucleotide sequence of lineage I WNV strain 3356 of GenBank accession No. AF404756 (SEQ ID NO.1). The bold underline nucleotides indicate those that differ with the derivatized fully-infectious lineage I WNV cDNA clone of FIG. 21.

FIG. 21 shows the nucleotide sequence of the fully-infectious lineage I WNV strain 3356 cDNA clone (SEQ ID NO.2). The bold underline nucleotides indicate those that are different with respect to the nucleotide sequence of the parental lineage I WNV strain 3356 of FIG. 20.

DETAILED DESCRIPTION OF THE INVENTION

Figure 3:
FIG. 3 shows the identical behaviour of the in vitro RNA transcription product of pFLWNV (i.e., RNA of the full-length lineage I WNV cDNA clone) and the genomic WNV RNA as analyzed by formaldehyde-denaturing gel electrophoresis through 1.0% agarose.

The instant invention relates to novel genetically engineered flavivirus constructs, especially WNV, methods for rapidly identifying novel antiflaviviral chemotherapeutics and/or attenuated virus vaccines using genetically engineered WNV constructs, cell lines stably containing the genetically engineered flavivirus constructs, especially WNV, for use in the high-throughput screening assays, and pharmaceutical compositions comprising an attenuated flavivirus, especially WNV, effective to immunize against infections by a flavivirus, e.g., WNV, JEV, SLEV, AV, KV, JV, CV, YV, TBEV, DENV-1, DENV-2, DENV-3, DENV-4, YFV and MVEV and other known or emerging flaviviruses. More specifically, the present invention relates to novel lineage I WNV reverse genetics systems, and methods for making the reverse genetics systems, especially, a fully-infectious lineage I WNV cDNA or replicon system engineered with one or more nucleotide sequences each encoding a reporter to be used in high-throughput cell-based screening assays for the identification of novel antiflaviviral chemotherapeutics and/or vaccines effective to treat and/or immunize against infections by WNV, DENV, and other emerging flaviviruses. The instant invention is further directed to high-throughput methods for screening compounds for antiflaviviral properties or improved derivatives thereof using novel lineage I WNV reverse genetics systems and/or cell lines stably containing the reverse genetics systems. Also, the invention provides a pharmaceutical composition comprising an attenuated lineage I WNV that is less virulent but similarly immunogenic as the parent WNV and is capable of providing a protective immune response in a host against a flavivirus, e.g., WNV, DENV, and other known or emerging flaviviruses.

Thus, according to a first aspect of the present invention there is provided a fully-infectious lineage I WNV cDNA and method for constructing same that is engineered with at least one nucleotide sequence encoding a reporter effective to monitor the replication level of a WNV cDNA infectious RNA in an infected cell. The instant invention further provides a novel high-throughput, cell-based screening assay utilizing the WNV cDNA engineered with at least one nucleotide sequence encoding a reporter to identify novel antiflavirus inhibitors (i.e., chemotherapeutics) or to develop novel vaccines comprising attenuated WNV strains effective to immunize against infections by against a flavivirus, e.g., WNV, JEV, SLEV, AV, KV, JV, CV, YV, TBEV, DENV-1, DENV-2, DENV-3, DENV-4, YFV and MVEV and other known or emerging flaviviruses.

In one embodiment of the present invention, a parental WNV, especially strain 3356 (see FIG. 20), is used as a starting point in constructing the reverse genetics systems of the invention. Throughout the present application, the terms "reverse genetics systems" or "WNV reverse genetics systems" encompass the recombinant WNV cDNAs of the present invention. The terms "recombinant WNV cDNAs" of the invention refer to the "WNV cDNA clone" or "lineage I WNV DNA clone" and the "WNV replicon" or "lineage I WNV replicon". These "reverse genetics systems", in accordance with the instant invention, relate to cDNA clones of the RNA genome of WNV, especially lineage I WNV. A "reverse genetics system", however, would be understood by one of ordinary skill in the art to mean a cDNA formed from the RNA-based genome of an RNA virus. The reverse genetics system can also be cloned or inserted into a vector, such as, for example, a plasmid, phage, or cosmid, etc.

An RNA virus can be a "negative-sense" (i.e., a "minus-strand") or a "positive-sense" (i.e., a "plus-strand") RNA virus, especially WNV, but not intended to be limited thereto. The terms "positive-sense" and "negative-sense" relate to the correspondence between the RNA genome of the virus and the coding sequence of the genome. For example, if the RNA virus is a "positive-sense" virus, then the RNA genome of the virus itself forms the coding sequence for the genes of the genome. On the other hand, if the RNA virus is a "negative-sense" virus, the RNA genome is the complement of the coding sequence for the genes of the genome. A negative-sense RNA virus must transcribe their RNA genome into a positive-sense strand of RNA (i.e., mRNA) as a step during their infection cycle, which is carried out by an RNA replicase or RNA replicase complex. In contrast, the RNA genome of a positive-sense RNA virus, such as a flavivirus, can be directly translated during the infectious cycle without having to be transcribed to a complementary strand of RNA. The term "infection cycle" refers to the course of events of a viral infection, including in some viruses the steps of cell infection and entry, viral genome replication and expression, viroid formation or "packaging," and viral exit. Further, an RNA virus genome can be a single-stranded or double-stranded molecule of RNA. Further still, the RNA virus genome can be organized as a single molecule of RNA or segmented into a plurality of distinct RNA subgenomic molecules.

In accordance with the instant invention, a "parental" WNV refers to a strain that is originally isolated from the naturally-occuring population. For example, WNV isolates to be used as parental strains can be obtained directly from mosquitoes. Infected mosquitoes can be captured in dry ice-baited CDC miniature light traps. Such traps can be placed at a specific location and left overnight to lure and collect the mosquito vectors. Mosquitoes can be tested for WNV; positive-testing mosquitoes can serve as a source of WNV. Mosquito species that are suitable for WNV collection include *Aedes vexans, Ae. cinereus, Ae. trivittatus, Ae. taeniorhynchus, Ae. sollicitans, Ae. cantator, Ae. triseriatus, Ae. japonicus, Ae. canadensis, Anopheles punctipennis, An. quadrimaculatus, An. walkeri, Coquillettidia perturbans, Culex pipiens, Cx. restuans, Cx. erraticus, Cx. territans, Culiseta melanura, Cs. morsitans, Psorophora ferox,* and *Uranotaenia sapphirina*

To isolate WNV from mosquitoes, frozen pools of the insects can be thawed, and then triturated in tissue grinders or mortars with pesles in 1 to 1.5 ml of phosphate-buffered saline ("PBS") containing 0.5% gelatin, 30% rabbit serum, antibiotic, and antimycotic. After centrifugation for 10 min at 520×g, 100 µl samples of each pool of mosquitoes can be inoculated onto a monolayer of Vero cells grown in a 25-cm$^2$ flask at 37° C. in 5% $CO_2$. Cells can be examined microscopically for cytopathologic effect for up to 7 days after inoculation.

Alternatively, the flavivirus of the invention, especially WNV, can be isolated from infected hosts, such as, for example, crows, ducks, humans, and any animal susceptible to infection by said flavivirus. In one embodiment, frozen bird brain tissue can be suspended in 1.5 mls of phosphate-buffered saline by triturating with a mortar and pestle as described above for mosquito samples except that Alundum® can be added to facilitate homogenization of tissue. Two to seven tissue samples from each brain can be tested for virus as follows. Suspensions can be centrifuged at 520×g for 10 min. The supernatant of each sample can then be passed through a 0.22-µm filter before inoculation of a 100-µl sample onto a monolayer of host cells. One skilled in the art will appreciate that any cell that is capable of being infected by WNV and compatible with the replication of the virus can be used as the host cell, including, but not limited to, human, monkey, mouse, and hamster cells. Cells can be grown in a 25-cm$^2$ flask at 37° C. in 5% $CO_2$ and examined for cytopathologic effect for up to 7 days after inoculation.

It will also be apparent to one of skill in the art that WNV can be obtained from a depository (including for example commercial or public depositories) containing biological materials, such as the American Type Culture Collection (ATCC), which holds deposits of biological material including, for example, strains of algae, animal viruses, bacteria, bacteriophages, cell lines, cloned genes, embryos, filamentous fungi, hybridomas, plant tissue cultures, plant viruses, purified DNA, protozoa, recombinant DNA materials (plasmid and phage vectors, libraries, etc.), seeds, and yeasts. One of ordinary skill in the art will understand the various ways, including the regulations and procedures necessary, by which to obtain biological materials, especially the virus strains and the cells lines of the instant invention from a depository. An example of a parental WNV strain maintained by the ATCC includes strain B956, designated as ATCC No. VR-82 and is capable of infection and replication in mouse, hamster, monkey, chicken embryo, duck embryo, hamster kidney, and human cells. Thus, the strain of WNV, i.e., the parental strain, used in accordance with the present invention can be obtained from a variety of sources.

According to various embodiments of the present invention, the parental WNV is strain 3356 (GenBank accession No. AF404756), which was isolated from the kidney of an American crow collected in October 2000 from Staten Island, N.Y. (G. D. Ebel, et. al., Emerg. Infect. Dis. 7:650-653). WNV stock is made after two passages on Vero cells without plaque purification. However, one of ordinary skill in the art will understand that the parental WNV strain of the instant invention is not limited to a single isolate of WNV, but can be any known in the art or any future strain of WNV isolated.

In accordance with the instant invention, the flaviviruses of the invention, especially WNV, can be isolated from host cells infected with said flavivirus. Methods for isolating viruses, in particular, flaviviruses, from host cells are known in the art and are described in Specter, S. C. et al., *Clinical Virology Manual*, 3$^{rd}$ Edition (2000), Leda, R., *Methods in Molecular Biology*, v. 165 (2001), Collins, M. K., *Methods in Molecular Biology*, v. 8 (1991). Preferably, the flaviviruses of the invention, especially WNV, will be harvested from the culture supernatant of infected cells. Once isolated, the genomic material (i.e., genomic RNA, positive, single-stranded) can be isolated and purified. One of ordinary skill in the art will understand that many different methods can be used to isolate and/or purify genomic material from the flaviviruses of the present invention, especially WNV.

In one embodiment of the instant invention, BHK-21 cells (baby hamster kidney cells, ATCC CCL-10; Manassas Va.) are infected with an isolated, naturally-occurring strain of WNV, such as WNV 3356. Infection can be achieved by contacting the host cells with whole WNV intact virions or by transforming the host cells, such as by the method of transfection, the host cells with isolated WNV RNA. The infected cells can be grown on compatible medium, such as Dulbecco's modified minimal essential medium, supplemented with 10% fetal bovine serum, 0.1 mM nonessential amino acids, 10 U/ml penicillin, and 10 µg/ml streptomycin. One of ordinary skill in the art will appreciate that different multiplicities of infection (MOI; the ratio of virus particles to cells) can be used, for example a MOI of 0.5. It will be appreciated that the appropriate MOI will depend on numerous factors known to those of ordinary skill in the art, such as, for example, the infectivity of the virus, the susceptibility of the host to infecting virus, and the growth phase of the host cells.

In accordance with the instant invention, a flavivirus, such as, for example, WNV, can be harvested from the cell culture medium at different times following inoculation of the cells with said flavivirus, for example, after 36 hours postinoculation. Following the incubation and replication of said flavivirus in the cell line, the virus particles can be purified by a variety of methods known in the art. The genetic material of the virus can then be purified. One of ordinary skill in the art will appreciate that there are numerous methods and commercial kits available for the purification of a viral genome, such as the RNA genome of a flavivirus, especially WNV. For example, the genomic RNA can be extracted from the virus particles collected in the cell culture medium using the RNeasy RNA extraction kit (Qiagen, Valencia, Calif.). Further methods for extracting and purifying WNV genomic RNA can be found in J. Sambrook and D. W. Russell, *Molecular Cloning: A Laboratory Manual*, Third Edition (2001).

The instant invention contemplates a variety of strategies to generate reverse genetics systems of the flaviviruses of the present invention, especially WNV and its derivatives, such as the full-length lineage I cDNA clone and a lineage I replicon of the invention. Example 1 is provided to illustrate one method for constructing the lineage I WNV cDNA clone in accordance with the instant invention. One skilled in the art will appreciate that since WNV is an RNA virus containing a single segment of positive-stranded RNA, it can be converted to a cDNA molecule to enable genetic manipulation. To further enable genetic manipulation, the cDNA molecule of the WNV can be advantageously inserted, i.e., "cloned," into an appropriate cloning vector. It will be appreciated by one of ordinary skill in the art that cloning requires at least a vector and a suitable host cell that is compatible with the vector, i.e., one wherein the vector is stably maintained and replicated. Further, one of ordinary skill in the art will understand that methods of converting RNA to a cDNA molecule, such as by reverse-transcriptase PCR (RT-PCR), are well-known in the art. Further description of RT-PCR can be found in J. Sambrook and D. W. Russell, *Molecular Cloning: A Laboratory Manual*, Third Edition (2001).

It will be appreciated that a wide variety of host cells and vectors can be used for cloning purposes. The term "host cell" refers to one or more cells into which a recombinant DNA molecule is introduced. A "vector" is a replicon, such as a plasmid, phage, or cosmid, to which another DNA segment may be attached so as to bring about the replication of the attached segment. A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, IRES ("internal ribosomal entry site") and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. A control element, such as a promoter, "directs the transcription" of a coding sequence in a cell when RNA polymerase will bind the promoter and transcribe the coding sequence into mRNA, which is then translated into the polypeptide encoded by the coding sequence. Operably linked may also refer to an arrangement of two or more genes encoded on the same transcript. This arrangement results in the co-transcription of the genes, i.e., both genes are transcribed together since they are present on the same transcript. This operably linked arrangement of genes can be found in a naturally occurring DNA or constructed by genetic engineering. Further, according to this operable linkage, the genes can be translated as a polyprotein, i.e., translated as a fused polypeptide such that the resultant proteins are interlinked by a peptide bond from a single initiation event, or the genes can be translated separately from independent translation initiation signals, such as an IRES (", which directs translation initiation of internally-situated open reading frames (i.e., protein-coding regions of a transcript).

Host cells of the invention include, but are not limited to, bacterial cells, such as any Gram-positive, such as *Bacillus subtilis*, or Gram-negative bacterium, such as *Escherichia coli*, or any other suitable bacterial strain, fungal cells, such as the yeast *Saccharomyces cerevisiae*, animal cells, such as hamster, human, or monkey, plant cells, such as *Arabidopsis thaliana*, or insect cells, such as mosquito, or any other suitable cell. Host cells can be unicellular, or can be grown in tissue culture as liquid cultures, monolayers or the like. Host cells may also be derived directly or indirectly from tissues, such as liver, blood, or skin cells. Vectors can include plasmids, such as pBluescript SK, pBR322, and pACYC184, cosmids, or virus/bacteriophage, such as pox virus vectors, baculovirus vectors, adenovirus vectors, and lambda, and artificial chromosomes, such as yeast artificial chromosomes (YAC), P1-derived artificial chromosomes (PACs) and bacterial artificial chromosomes (BACs), so long as they are compatible with the host cell, i.e., are stably maintained and replicated. Further, preferred prokaryotic vectors include plasmids such as those capable of replication in *E. coli*, for example, pBR322, ColE1, pSC101, pACYC 184, etc. (see Maniatis et al., Molecular Cloning: A Laboratory Manuel), *Bacillus* plasmids such as pC194, pC221, pT127, etc. (Gryczan, T., The Molecular Biology of the Bacilli, Academic Press, NY (1982), pp. 307-329); *Streptomyces* plasmids including pIJ101 (Kendall, K. J. et al., (1987) J. Bacteriol. 169:4177-4183); *Streptomyces* bacteriophages such as phiC31 (Chater, K. F. et al., in: Sixth International Symposium on Actinomycetal es Biology, Akademiai Kaido, Budapest, Hungary (1986), pp. 45-54), and *Pseudomonas* plasmids (John, J. F., et al. (1986) Rev. Infect. Dis. 8:693-704), and Izaki, K. (1978) Jpn. J. Bacteriol. 33:729-742). Preferred eukaryotic plasmids include BPV, vaccinia, SV40, 2-micron circle, etc., or their derivatives. Such plasmids are well known in the art (Botstein, D., et al. (1982) Miami Wint. Symp. 19:265-274; Broach, J. R., in: The Molecular Biology of the Yeast Saccharomyces: Life Cycle and Inheritance, Cold Spring Harbor Laboratory, Cold Spring Harbor, N.Y., pp. 445-470 (1981); Broach, J. R., (1982) Cell 28:203-204; Bollon, D. P., et al. (1980) J. Clin. Hematol. Oncol. 10:39-48; Maniatis, T., in: Cell Biology: A Comprehensive Treatise, Vol. 3: Gene Expression, Academic Press, N.Y., pp. 563-608 (1980)).

Preferred vectors may also be of bacterial origin, which may comprise a promoter of a bacteriophage such as phage or T7 which is capable of functioning in the bacteria. In one of the most widely used expression systems, the nucleic acid encoding the fusion protein may be transcribed from the vector by T7 RNA polymerase (Studier et al, *Methods in Enzymol*. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX (Invitrogen, NL), vectors containing the trc promoters such as pTrcHisXpress™ (Invitrogen), or pTrc99 (Pharmacia Biotech, SE), or vectors containing the tac promoter such as pKK223-3 (Pharmacia Biotech), or PMAL (New England Biolabs, MA, USA).

Additionaly, recombinant viral vectors may be used. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10): 1619-32).

It will be appreciated that host cells and vectors can readily be obtained from publically-available depostories, such as GenBank at the National Center for Biotechnology Information (U.S.A) or through any commercial source, such as from Stratagene (La Jolla, Calif.), New England Biolabs (Beverly, Mass.), or BD Biosciences (Palo Alto, Calif.). One of ordinary skill in the art will further appreciate that combinations of vectors and host cells can be tested for stability prior to use. Such stability testing can be carried out, for example, by examining the integrity of a plamid vector isolated from a culture over time using known methods such as, restriction enzyme analysis in combination with agarose gel electrophoresis.

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned lineage I WNV cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/$CaPO_4$ co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., *Molecular Biomethods Handbook*, Chapter 20, p. 235-250. It will be further appreciated that infection of host cells with viral RNA, such as an RNA transcription product of the fill-length lineage I cDNA clone of the instant invention, can be achieved by the methods of transfection discussed above.

In accordance with the instant invention, the flavivirus reverse genetics systems, especially the reverse genetics systems of WNV, such as the lineage I WNV replicon or the full-length lineage I WNV cDNA, can be engineered to contain one or more genetic markers. The term "genetic marker" in accordance with the instant invention refers to a variation in the sequence and/or structure of a first nucleic acid molecule that allows it to be distinguished over a second nucleic acid molecule. The "variation" can include, but is not limited to, a deletion or insertion of nucleotides, one or more single nucleotide changes, a chemical modification to one or more nucleotides, such as a methylation, or one or more eliminated and/or added restriction enzyme recognition sequences. The genetic marker can be introduced into a nucleic acid, including but not limited to a chromosome, genome, plasmid vector, bacteriophage vector, or DNA fragment, by a variety of molecular and/or genetic methods known to one of ordinary skill in the art, such as by PCR, chemical mutagenesis, site-specific mutagenesis, and restriction fragment deletion, insertion or substitution. Example 1 is further provided to illustrate the method of introducing genetic markers into the full-length lineage I WNV cDNA. Example 2 is further provided to illustrate the method of restriction enzyme analysis, gel electrophoresis, and sequence analysis to distinguish between the parental WNV and the full-length WNV cDNA based on the genetic markers of the WNV cDNA.

According to another embodiment of the instant invention, in vitro transcription is carried out on a recombinant plasmid (such as, for example, pFLWNV of Example 1) carrying a cloned flaviviral cDNA, such as the lineage I WNV cDNA of the invention, under the control of an expressible promoter (i.e., a promoter which is effectively enabled or activated in vitro in the presence of corresponding transcription factors and RNA polymersase). The transcription process generates a fully-infectious flaviviral mRNA transcript that can be used to transfect (i.e., infect) a cell host, such as BHK-21 (hamster kidney cells) or Vero cells. In one embodiment, the lineage I WNV cDNA is operably linked with the bacteriophage transcriptional promoter, T7; to enable the in vitro transcription of the WNV cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of the flavivirus genome and for controlling the expression of a nucleotide sequence encoding a reporter is contemplated by the present invention. It will be appreciated that the promoter is typically selected from promoters which are functional in mammalian cells suspectible to infection by the flaviviruses of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of the flavivirus genome or construct is to occur.

With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of the flavivirus genome can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

The resultant mRNA transcript according to the instant invention can be fully-infectious, i.e., able to infect a cell and carry out a complete infection cycle culminating in the production of new virus particles. Example 3 is provided to exemplify the transcription of lineage I cDNA to form fully-infectious WNV RNA.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availablity of purified recombinant proteins facilitates the generation of large quantities of RNA from cloned cDNA sequences. In constrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukarotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., *Molecular Biomethods Handbook*, Chapter 26, p. 327-334 and Sambrook, J. and D. W. Russell, *Molecular Cloning: A Laboratory Manual*, Third Edition (2001).

In another aspect of the instant invention, the reverse genetics systems, such as the lineage I WNV replicon or the full-length lineage I WNV cDNA, are engineered to contain one or more nucleotide sequences each encoding a reporter. The expression of the reporter-encoding nucleotide sequences can be monitored and/or measured to indicate the replication activity of WNV RNA, i.e., the degree to which the WNV RNA is being replicated in the cell or the relative requency by which a gene or promoter is transcribed. In a preferred embodiment, the nucleotide sequence encoding the reporter is engineered into a WNV cDNA to enable the co-transcription of the reporter with the WNV genome such that a single mRNA transcript is formed containing all of the open reading frames for each WNV gene and the reporter. One of ordinary skill in the art will understand that the term "reporter" refers to a type of protein that can by easily assayed or detected, or one which has an enzymatic activity that can be measured and/or detected. A reporter may also be one whose activity or properties thereof enables the cell in which it is expressed to persist under certain environmental conditions wherein the cell would not survive in the absence of the reporter. This enables a cell expressing the reporter to be "selected" for under a certain over cells that are not expressing the reporter. Although not meant to be limiting to the scope of the application, one class of reporters includes the antibiotic resistance markers, such as, for example, the neomycin phosphotransferase (Neo) of the invention. The term "activity" as it is used in the instant invention refers to a catalytic activity of a protein or enzyme that can be assayed. One of skill in the art will appreciate that a single protein or enzyme can comprise a plurality of activities and thus, not limited each to a single activity. Further, the activity of a protein is typically linked to a specific physical region, domain, or set of domains on the protein and thus, by joining proteins together, either naturally as with multi-subunit proteins or recombinantly, as with "fusion proteins", different activities can be combined.

Some reporter are enzymes, which can be detected by introducing calorimetric or fluorogenic substrates, i.e., substrates that produce a detectable color or emit a fluorescence signal when acted upon by the reporter (e.g. firefly luciferase, a reporter, catalyzes the cleavage of a fluorescence-emitting substrate such as luciferin). Enzymes that can be used as reporter genes can include oxidases, luciferases, peptidases (such as caspase-3), glycosidases (such as beta-galactosidase) and phosphatases (such as alkaline phosphatase). Reporter can also include fluorescent proteins, such as green fluorescent protein (GFP), the fluorescent signal of which can be detected directly following illumination with ultraviolet light. The invention contemplates the use of any currently known or yet-to-be discovered fluorescent proteins as the reporters of the invention. It will be appreciated by one of ordinary skill in the art that novel naturally-occurring fluorescent proteins can potentially be discovered in the environment from naturally-occurring fluorescence organisms, such as many species of ocean coral and other deep-sea life. It will also be appreciated that reporters, such as fluorescent proteins, and their corresponding nucleotide sequences and cloning tools, such as, reporter-encoding vectors, can be obtained from commercial sources, such as, for example, BD BIOSCIENCES (CA), which provides the BD LIVING COLORS™ GFP-based and Reef Coral Fluorescent Proteins (RCFP), such as, for example, AmCyan1, ZsGreen1, ZsYellow1, DsRed2, AsRed2, and HcRed1. In accordance with the instant invention, an antibiotic resistance marker can function as the reporter. In addition, antibiotice resistance genes also function as selectable markers. The term "selectable marker" refers to a gene whose product enables a cell to grow in the presence or absence of a specific environmental condition, such as in the presence of an antibiotic. In an embodiment of the present invention, a lineage I WNV replicon is provided containing a neomycin resistance gene (Neo), which, when expressed in a cell, enables the cell to grow in the presence of the antibiotic, Geneticin. Cells not expressing Neo do not survive. In another example, the chloramphenicol acetytransferase (CAT) gene found in the *E. coli* transposon Tn9 can be used. The usual substrate for this assay is $^{14}$C-chloramphenicol. The resulting acetylated products can be quantified using direct-scintillation counting. Also, nonradioactive substrates of CAT are available, which can be detected and quantified using fluorimetry techniques.

In one embodiment of the present invention, the reporter is GFP. One of ordinary skill in the art will be familiar with the use of GFP as a reporter gene. GFP-expression vectors are commercially available (BD BIOSCIENCES). GFP-expressing cells can be directly observed using fluorescence microscopy. GFP-expressing cells can also be screened using existing high-throughput screening instrumentation, including fluorescence-quantification instruments, such as luminometers or fluorimeters. It will be appreciated that that the instant invention contemplates both yet-to-be developed high-throughput screening instruments, as well as any suitable currently available high-throughput screening instruments, such as, the BD Monolight 3096 (BD Biosciences, Franklin Lakes, N.J.), which is an easy-to-use, ultra-sensitive, photon-counting luminometer designed for the detection of bio/chemiluminescence in a microplate format, or the Jenway Model 6200 Fluorimeter (Wolf Laboratories Limited, York, UK). In an embodiment of the instant invention, cells infected with lineage I WNV reverse genetics systems engineered with a GFP gene are monitored by detection of the expression of the GFP reporter using a fluorescence-activated cell sorting (FACS) system. FACS systems are commercially available, such as, for example the BD FACS-Vantage SE System (BD Biosciences) or the MOFLO modular flow cytometer (DakoCytomation). In another embodiment, cell-based assays are carried out in microtiter/microarray plates containing a plurality of reaction wells, such as, about 100, about 400, or about 1600, wherein the fluorescence signal from each well can be measured simultaneously by a "reader" and compared using any fluorescence-plate reading instrumentation available in the art. The high throughput methods of the invention further contemplate software available to facilitate the high throughput reading and storage of data, in the form of images and measurements or reporter gene expression, such as the relative expression levels of GFP as indicated by the relative level of fluorescence emitting from the cells of the assayed cell line.

A further description of GFP and its use as a reporter in cell-based assays can be found in Hicks, B. W., (2002) *Green Fluorescent Protein: Applications and Protocols*, v. 183 of Methods in Molecular Biology.

In one embodiment of the instant invention, the GFP gene is inserted into the fully-infectious lineage I WNV cDNA clone in a position downstream of the NS5 gene, but upstream of the 3' untranslated regulatory region. Preferrably, the GFP gene is orientated in the same direction as the genes of the WNV genome such that the GFP gene is co-transcribed (i.e., GFP gene is not preceded by separate promoter) with the WNV genes upon in vitro transcription of the WNV cDNA. In a further embodiment, the GFP gene is preceded by an internal ribosomal entry site (IRES) upstream of the coding region of the GFP gene to enable independent translation of the GFP coding region from the RNA transcribed from the GFP-containing WNV cDNA.

In another embodiment of the instant invention, the reporter is firefly luciferase. It will be appreciated that luciferase catalyzes the oxidation of D-luciferin in the presence of ATP, $Mg^{2+}$ and $O^2$ to give oxyluciferin, $CO^2$ and a photon of light. The reaction in vitro is extremely rapid, reaching maximum levels of emitted light within 3-5 seconds after which there is an equally rapid decay to 10% of the peak value. Therefore, it will be understood that in order to take full advantage of the sensitivity of the assay, a luminometer can be employed that automatically mixes sample and substrate and measures light emission over a 10 second period. The instant invention also contemplates the use of the *E. coli* lacZ gene the corresponding reporter, LacZ. LacZ is the glycoside hydrolase β-D-galactosidase (β-gal). A variety of substrates are available for the enzyme allowing quantitation of gene expression by spectrometry, fluorimetry, and by fluorescence-activated cell sorting (FACS analysis, and other microplate/microtiter plate fluorescence assays. The most common use of β-gal is in combination with X-gal from which it produces an insoluble blue product.

In yet another embodiment of the instant invention, two different reporters are used. It will be understood that the reporters can be any known reporters in the art, such as, for example, oxidases, luciferases, peptidases (such as caspase-3), glycosidases (such as beta-galactosidase), phosphatases (such as alkaline phosphatase), and fluorescent proteins, such as GFP or a variant thereof. In a further embodiment, a lineage I WNV replicon is provided with both a neomycin-resistance gene and a GFP gene. The neomycin-resistance gene (neo) enables the selection of only those infected cells which stably replicate the WNV replicon, i.e., neo, which encodes the protein Neo, allows a cell that is stably replicating the WNV replicon to grow in the presence of the antibiotic, neomycin. In this way, a cell line can be obtained that stably replicates the WNV replicon, wherein each cell of the cell line contains the WNV replicon. Thus, the neo gene is utilized as a selectable marker. Further, GFP, one reporter according to the present embodiment can be monitored by fluorescence detection. It will be appreciated that the level of expression of the reporter, such as GFP of the present embodiment, is expressed at a level that is proportional to the replication activity of the WNV replicon, i.e., the expression of the reporter is directly proportional to the quantity of WNV replicon RNA in the cell. It will be appreciated that any combination of a selectable marker (which also can be regarded as a specific type of reporter) known in the art and another reporter known in the art can be used to construct a WNV replicon containing two different reporters. Further, it will be understood that the invention contemplates combining more than two reporter and/or selectable markers.

The term "IRES" or "internal ribosomal entry site" as it is used in the present invention refers to a specific sequence of RNA that directs the initiation of translation from a site downstream of the 5' end of the mRNA, i.e., internal mRNA sequence for initiation of translation. Translation from an IRES can be understood from the more commonly known mechanisms of eukaryotic translation called "cap-dependent translation initiation" or "scanning ribosome mechanism" (SRM). SRM states that initial contact between protein components (initiation factors and the 40S ribosomal subunit) and mRNA occurs at the 5' end of the mRNA followed by the scanning of the RNA by the ribosome to reach an authentic translation initiator AUG, which often is the first AUG sequence. The discovery of the 5'-terminal cap structure (m7GpppN) of eukaryotic mRNA and the description of proteins with the ability to bind both to the cap structure and to ribosomal subunits provided a plausible mechanism by which the 40S ribosomal subunits could be attracted to the 5' end of mRNA. The 5' cap structures are believed to play an important role in the initial ribosome entry or binding step.

Initiation of translation at an internal site of the mRNA by an IRES (which forms a secondary structural element in the RNA molecule) is referred to as "cap-independent tranlation initiation." IRESes were first discovered in picornaviruses (Jackson & Kaminski 1995; Jang et al, (1988) J. Virol. 62(8): 2636-43). Viral IRESes can be divided into several functional groups based on their primary sequence and structure (Jackson & Kaminski 1995), which include type I IRESes (e.g., from enteroviral and rhinoviral), type II IRESes (e.g., from cardioviruses and aphthoviruses), and type III IRESes (e.g., from hepatitis A virus), which are relatively inefficient initiators of translation.

IRESes can be functionally discriminated from other 5'UTR secondary structures by their ability to mediate translation of the downstream ORF of a bi-cistronic reporter mRNA, independent of the translational status of the first ORF (Jang et al 1988, Pelletier & Sonenberg 1988). The majority of general initiation factors, including eIF-4F, appear to be required for IRES-mediated translation (reviewed in Jackson 1995). Exceptionally, the IRESes from hepatitis C and classical swine fever viruses appear to bind the small ribosomal subunit and position it properly at the AUG, without the need for initiation factors (Pestova et al 1998). This mechanism of initiation may be most analogous to prokaryotic translation, in that the IRES may be functionally equivalent to Shine-Dalgarno sequences (Pestova et al 1998). Translation from other IRESes requires additional trans-acting factors, such as polypyrimidine tract-binding protein (PTB) (Hellen et al 1993, Kaminski et al 1995) and the La autoantigen (Meerovitch et al 1993, Svitkin et al 1994a). Further description of translation control, particularly by IRESes can be found in N. K. Gray and M. Wicker, Annu. Rev. Cell Dev. Biol. (1998) 14: 399-458.

Figure 17:
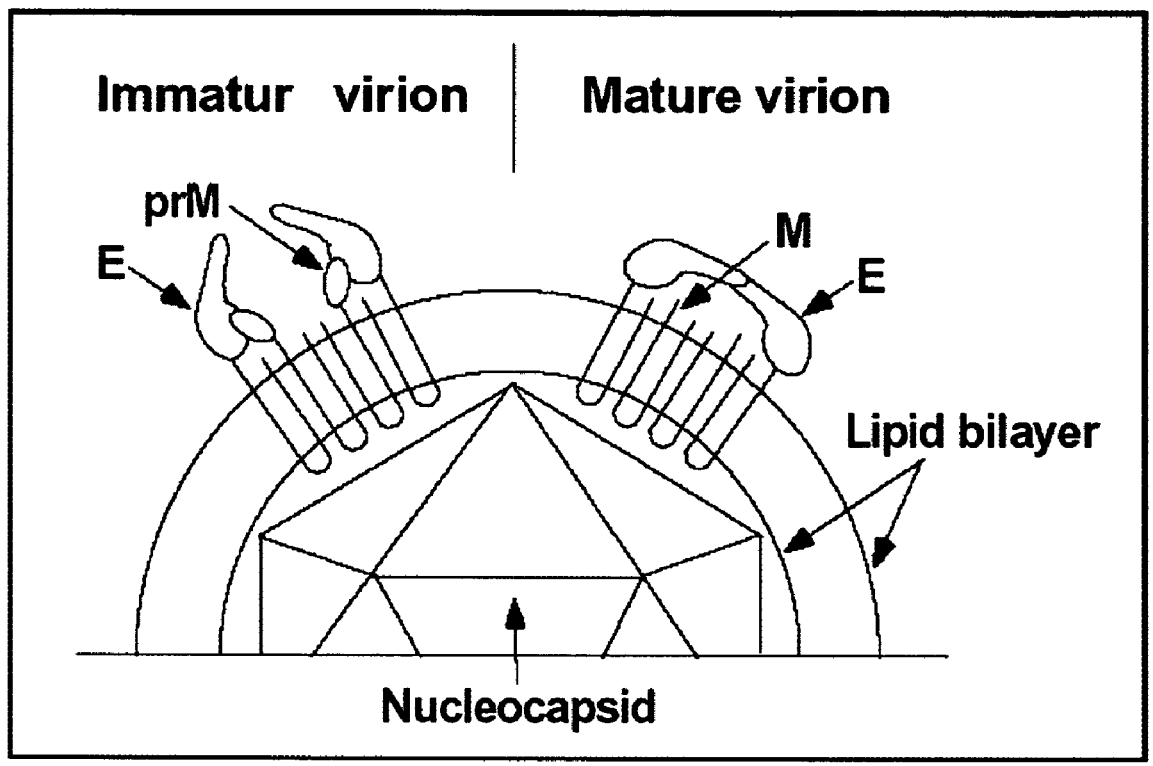
FIG. 17 shows a schematic contrasting the immature and mature flavivirus virions.

In another aspect of the instant invention, high throughput methods for screening antiflaviviral chemotherapies using the flavivirus reverse genetics systems of the present invention, especially the lineage I WNV cDNAs or the lineage I WNV replicon systems are provided. In one embodiment, the high throughput methods are cell-based assays, which measure the level of expression of a reporter, such as GFP, in the presence of a potential antiflaviviral chemotherapeutic, such as an inhibitor. One of ordinary skill in the art will understand that screening for and identification of antiflaviviral chemotherapeutics according to the cell-based approaches of the instant invention is advantageous over biochemical based approaches. First, biochemical-based screening methods are limited to the testing of a single protein or activity at a time. In contrast, cell-based approaches (i.e. "genetic approaches") for screening chemotherapeutics, such as the methods provided by the instant invention, screen for potential chemotherapeutics against any and all activities required during the normal viral infection cycle in a simultaneous manner.

One of ordinary skill in the art will appreciate that each and every aspect of the infection cycle of a flavivirus can be a potential target for antiflaviviral chemotherapy, e.g., an inhibitor of genome replication, an inhibitor of viral assembly, or an inhibitor of viral protein expression. A description of the infection cycle of a flavivirus is provided to highlight some of the key processes that occur therein that may be targets, however, one skilled in the art will appreciate that further research in the area of flavivirus virology may indicate additional potential targets and strategies for antiflaviviral chemotherapy, all of which are contemplated by the instant invention. Further, it will be understood that in addition to viral targets, host functions required for a successful flavivirus infection cycle may also be targeted by antiflaviral chemotherapy, for example, cellular factors relating to virus entry into the cell or cellular proteases necessary for correct processing of the flavivirus translation products.

In the first aspect of the normal infection cycle, the flavivirus attaches to an as yet unidentified receptor on the host cell surface. Host cells capable of being infected by a flavivirus include cells of mammalian, avian, or insect origin. After binding, virions are taken up by receptor-mediated endocytosis. In the endocytotic vesicle, acid-catalyzed membrane fusion releases the nucleocapsid into the cytoplasm. A conformational change in the viral E peptide is induced by low pH to expose the fusogenic domain. The flavivirus genome is then translated as a large polypeptide that is processed co- and post-translationally by cellular proteases and a virally encoded serine protease into 10 discrete products, which include the capsid (C), pre-membrane protein (prM), envelope protein (E), and 7 non-structural proteins, NS1, NS2A, NS2B, NS3, NS4A, NS4B, and NS5 (FIG. 16). Translation of the polypeptide is associated with the rough endoplasmic reticulum (ER), allowing some peptides to be translocated into the lumen of the ER, while others remain on the cytoplasmic side. Next, a cellular signal peptidase in the lumen of the ER cleaves the polypeptide to generate the N-termini of prM, E, NS1 and NS4B (FIG. 16). During the egress of the virion, prM is cleaved by the host enzyme furin to form structural protein M and the N-terminal 'pr' segment. The remaining cleavages of the polypeptide are mediated by NS2B-3 protease and generate the N-termini of NS2B, NS3, NS4A and NS5.

Non-structural peptides are primarily involved in the replication of viral RNA as parts of a replication complex. NS1 and its interaction with NS4A are required for RNA replication (Muylaert I. R., et al., J. Virol. (1997) 71:291-298; Lindenbach B., et al., J. Virol. (1997) 71:9608-9617; Lindenbach B. D. et. al., J. Virol. (1999) 73:4611-4621). The hydrophobic NS2a peptide was recently shown to function in the assembly and/or release of infectious flavivirus particles (Kummerer B. M., et al., J. Virol. (2002) 76:473-4784). NS2B forms a complex with NS3 and is a required co-factor for the serine protease function of NS3 (Chambers T. J., et al. J. Virol. (1991) 65:6042-6050; Chamber T. J., et al., J. Virol. (1993) 67:6797-6807; Arias C. F. et al., Virology (1993) 193:888-899; Falgout B. et al. J. Virol. (1993) 67:2034-2042). NS3 is a multi-functional peptide with serine protease, nucleoside triphosphatase and helicase activities. The functions of the membrane-associated NS4A and NS4B peptides are not yet known. NS5 functions as the viral RNA-dependent RNA polymerase (Tan B. H., et al., Virology (1996) 216:317-325; Ackermann M., et al., J. Biol. Chem. (2001) 276:39926-39937; Guyatt K. J., et al., J. Virol. Methods (2001) 92:37-44.) and as the methyltransferase involved in the methylation of the 5' RNA cap structure (Koonin E. V., J. Gen. Virol. (1993) 74:733-740). Upon flavivirus infection, the plus-strand genomic RNA is transcribed into a complementary minus-strand, which in turn serves as the template for the synthesis of more plus-strand genomic RNA (CHamber T. J. et al., Annu. Rev. Microbiol. 91990) 44:649-688). The synthesis of flavivirus plus- and minus-strand RNA is asymmetric; plus-strand RNA is produced in amounts 10- to 100-fold greater than that of minus-strand RNA (Muylaert I. R., Virology (1996) 222: 159-168; Diamond M. S., et al., J. Virol. (2000) 74:7814-7823).

Virus assembly takes place within the lumen of the ER, with the first step being the generation of fusion-incompetent, immature virions, with the E protein forming a stable heterodimeric complex with prM (FIG. 17). Immature virions are subsequently transported through the host secretory pathway to the cell surface, where exocytosis occurs. Shortly before the release of the virions from the cell surface, prM is cleaved to M by the host protease, furin. Upon cleavage of prM, the E-M interaction is destabilized and E peptides form homodimers yielding infectious mature virions (FIG. 17). Previous research using TBE virus suggested that the function of prM in immature virions is to hold the E peptide in a stable conformation, protecting it during its passage through the acidic secretory pathway from undergoing the irreversible conformational changes that are required for fusion activity, and that would otherwise lead to premature inactivation (Heinz F. X., Adv. Virus Res. (2000) 55:231-269. The atomic structure of the ectodomain of the TBE virus E protein has been determined by X-ray crystallography (Rey F. A., et al., Nature (1995) 375:291-298). It will be understood that the structure of the E protein, in addition to other solved flavivirus crystal structures, provides a possible basis for the rational design of flavivirus inhibitors.

One of ordinary skill in the art will appreciate that flavivirus replicon systems, such as the WNV replicon system of the instant invention, contain deletions of structural genes of the virus. Examples of structural genes include the genes encoding the capsid, envelope, and membrane proteins. Examples 10 is provided to illustrate a method for constructing the lineage I WNV replicon system, which contains deletions in the structural genes. Since replicon RNA contains only the non-structural genes required for viral replication, it will still replicate inside host cells upon transfection, but will be unable to be packaged to form viral particles that can infect neighboring cells. Nucleotide sequences encoding reporters, such as sequences encoding firefly luciferase or green fluorescent protein, can be engineered into the replicon system in a manner similar to the lineage I cDNA, and whole viruses containing the reporter-encoding nucleotide sequences can be generated by providing the deficient structural genes in trans. "In trans" will be appreciated by one of ordinary skill in the art to mean proteins supplied by expression from a separate DNA molecule, such as from a helper phage. One of ordinary skill in the art will understand that helper phage function to supply necessary proteins to the flavivirus replicon system to assist in replicon virus assembly wherein such proteins may include the capsid, envelope, and membrane proteins. Upon infection of the host cells with such viruses, the reporter protein will be produced and the level of reporter expression could indicate the replication level of viral RNA. It will be appreciated that detecting a reduction in intensity of the reporting signal in the presence of a compound indicates a potential antiviral compound, which can be further tested by genetics-based or biochemical-based methods. It will be understood that since no structural proteins are expressed in the subsequent round of infection, the replicon particles will limit the infection to a single cycle (also known as suicide infection). It will be appreciate though that unlike the embodiments that take advantage of the full-length WNV cDNA, the replicon WNV will not identify inhibitors of viral packaging and assembly, since no viral particles are formed, i.e., only inhibitors of replication aspects will be detected.

It will be appreciated that cell-based assays, i.e. genetic assays, for detecting inhibitors of viral activity are preferable to biochemical assays, which are limited to testing one protein target at a time. Genetic assays allow more than one protein to be targeted, and require uptake of the chemotherapeutic into cells, providing a physiologically relevant situation that often leads to higher success rates when tested in in vivo animal models. One of ordinary skilled in the art will appreciate that current cell-based assays for inhibition of flaviviral activities are time-consuming and labor-intensive involving assays such as quantification of cytopathic effects or RT-PCR. In contrast, the present invention provides a large-scale high-throughput assay for testing large amounts of antiviral compounds, such as with compound libraries. Using a reporter such as green fluorescent protein, alkaline phosphatase, horseradish peroxidase, or luciferase, such as Renilla (synthetic-hRLuc-, or native-RLuc) or firefly (available from PROMEGA CORPORATION, WI), rapid detection of changes in expression levels of these reporters is possible. For fluorescent reporters such as green fluorescent protein, flow cytometry (also known as fluorescence activated cell sorting or FACS) can be used to rapidly detect and quantify virus-infected cells in culture. The method of flow cytometry is well known to those with ordinary skill in the art, and is reviewed in McSharry, J. J. Clin Microbiol Rev (1994) 7(4):576-604 and Methods 2000 Jul.; 21(3):249-57. An advantage of flow cytometry is that heterogeneous populations of cells passed through the FACS machine can be collected and enriched according to the level of fluorescence detected, and used in subsequent assays.

The instant invention contemplates other assays to be used to detect reporter expression, such as luciferase (e.g., Renilla or firefly), whose expression levels can be measured by a bioluminescence assay. Additionally, calorimetric assays using alkaline phosphatase and nitroblue tetrazolium (NBT)/5-bromo-4-chloro-5-indolyl-phosphate (BCIP) substrates can also be used to screen for potential antiviral compounds. Alkaline phosphatase substrates can also be modified to emit a luminescent or fluorescent signal. Chemiluminescence and chemifluorescence can also be utilized with horseradish peroxidase. For radiolabeled compounds, scintillation assays are also used, as described above.

One of ordinary skill in the art will also appreciate that many lead compound testing procedures used in the drug discovery process benefit from running multiple chemical or biochemical reactions in parallel, such as the identification of drug leads and evaluation of compound solubility and stability. Typically, screening methods are performed in 96-well plates with sample volumes of approximately 300 µl. Emerging high throughput screening technologies in the art aim to reduce the amount of chemical library and other reagents consumed, as well as increase system throughput and the number of detection methods that can be integrated into such a system, and also to incorporate cell-based assays. The invention contemplates any method of high-throughput screening suitable in the art. For example, multiwell/microarray plates, such as 96-, 384-, or 1536-well polycarbonate plates can be used in connection with automated plate-reading instrumentation for the simultaneous detection and/or quantification of reporter signals. An advantage of the multiarray plate screening methods is that a smaller volume is required, which conserves space, assay reagents, compound library reagents, and scarce target materials. These technologies can be modified to incorporate cell-based plate assays, using fluorescence, luminescence, fluorescence polarization, time-resolved fluorescence, fluorescence resonance energy transfer, scintillation proximity assays, and calorimetric assays. In the case of fluorescence reporters, multi-channel plate readers have the ability to quantitatively detect multiple reporter signals that have different excitation wavelengths in a single cell population, further increasing the throughputness of the drug screening process. Other solid supports can be used, such as nylon membranes, silicon chips, and glass slides.

It will be understood by one of ordinary skill in the art that further reduction of the volumes of the wells of microplate arrays can lead to the trapping of gas bubbles, rapid sample evaporation, lower signal levels, and presents a formidable challenge for conventional liquid handling techniques such as pipetting. The micro- and nanotiter high-throughput technologies can be coupled to automated robotic systems, which virtually eliminate pipetting error and other problems in liquid handling. Additionally, temperature and environmental storage facilities and assay platforms can be used to address the problem of sample evaporation. These technologies used in conjunction can allow multiple synthetic combinatorial libraries of lead compounds to be screened, based on fluorescence signals emitted from GFP expression, luciferase activity, calorimetric assays such as ELISAs, which can use many different kinds of enzymes such as those detailed above, to produce a quantitative signal. Those skilled in the art will appreciate the numerous methods by which one could measure reporter expression in an automated, high-throughput manner. It is understood that with scaling-up to accommodate these high-throughput assays, data acquisition software can be implemented to analyze and collect data gained from these assays.

It will be appreciated that high throughput methods of the invention will involve performing screens on many thousands of compounds. To be most effective, the high-throughput methods will require parallel handling and processing of many compounds and assay component reagents. The high throughput screens of the present invention contemplate the use of mixtures of compounds and biological reagents along with some indicator compound loaded into arrays of wells in standard microtiter plates with a plurality of reactions wells, such as, for example, 96 or 384 wells. As a general reference, the microplates of will contain cell cultures where the cells of the cultures can comprise the flavivirus reverse genetics systems of the invention which are engineered with a least one nucleotide sequence encoding a reporter. For example, the cells of a given assay can be infected with a lineage I WNV replicon system or fully-infectious lineage I WNV cDNA clone wherein each of the respective derived WNV genomes can be further engineered to contain a nucleotide sequence encoding a reporter, especially GFP. The signal measured from each well, either fluorescence emission in the case of GFP, optical density, or radioactivity, integrates the signal from all the cells in the well giving an overall population average of, for example, the expression level of the GFP engineered WNV replicon. One of ordinary skill in the art will appreciate the plethora of instrumentation abaible commercially for the high throughput stage of data acquistion, such as automated microplate readers (i.e. imaging plate reader) which detect, read, store, and allow one to analyze fluorescence data from a microplate. All such instrumentation that would be known to one of ordinary skill in the art is contemplated by the instant invention.

Science Applications International Corporation (SAIC) 130 Fifth Avenue, Seattle, Wash. 98109) describes an imaging plate reader. This system uses a CCD ("cooled coupled device") camera to image the whole area of a 96 well plate. The image is analyzed to calculate the total fluorescence per well for all the material in the well. Such as device is contemplated by the high throughput assays of the present invention, for example, in determining the level of fluorescence of the GFP- or luciferase-engineered flavivirus genetics systems, in particular, the lineage I WNV fully-infectious cDNA and replicon system. Any device capable of detecting, or imaging, or acquiring the fluorescence signals from the cell-based assays of the present invention are contemplated.

Molecular Devices, Inc. (Sunnyvale, Calif.) describes a system which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a measurement of the average response of a population of cells. The image is analyzed to calculate the total fluorescence per well for cell-based assays. Fluid delivery devices have also been incorporated into cell based screening systems, such as Molecular Devices, Inc.'s system, in order to initiate a response, which is then observed as a whole cell population average response using a macro-imaging system.

It will be appreciated that the types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio et al., (1996) Mol. Biol. Cell. 7:1259; Giuliano et al., (1995) Ann. Rev. Biophys. Biomol. Struct. 24:405; Heim and Tsien, (1996) Curr. Biol. 6:178).

The methods of the instant invention relating to the detection of fluorescence signals, such as from GFP- or luciferase-expressing cells, the methods can involve live cells or fixed cells. The choice of fixed or live cell screens depends on the specific cell-based assay required. Methods for high throughput screening of live or fixed cells by fluorescence-based technologies are generally known in the art and can be found for example in U.S. Pat. No. 6,416,959, which is incorporated herein in its entirety.

One of ordinary skill in the art will appreciate that fixed cell assays comprise an array of initially living cells in a microtiter plate format that can be first treated with various compounds of interest, such as a potetial anti-flavivirus inhibitor, then fixed such that the cells are no longer living, then labeled with specific reagents, such as a flavivirus nucleic acid probe coupled to a fluorescent marker, and then measured and/or detected. One advantage of the fixed cell assay is that no environmental control of the cells is required after fixation. Although information is acquired it is limited to one time point. The availability of thousands of antibodies, ligands and nucleic acid hybridization probes, such as those for a flavivirus genome, which can be applied to cells makes this an attractive approach for many types of cell-based screens, such as those of the instant invention. The fixation and labeling steps can be automated, allowing efficient processing of assays.

The invention also contemplates high throughoutput methods involving living cells. Unlike fixed cells, an array of living cells containing the desired reagents, such as reagents to detect a flavivirus genome or a flavivirus expressed product, can be screened over time, as well as space. Environmental control of the cells (temperature, humidity, and carbon dioxide) is required during measurement, since the physiological health of the cells must be maintained for multiple fluorescence measurements over time. It will be appreciated that a fluorescent physiological indicators, or "biosensor," can be used to report changes in biochemical and molecular activities within the cells (Giuliano et al., (1995) Ann. Rev. Biophys. Biomol. Struct. 24:405; Hahn et al., (1993) In Fluorescent and Luminescent Probes for Biological Activity. W. T. Mason, (ed.), pp. 349-359, Academic Press, San Diego). According to the present invention, a biosensor is a macromolecule consisting of a biological functional domain and a luminescent probe or probes that report the environmental changes that occur either internally or on their surface and can be used to monitor the viability of the cells of the cell-based assays of the present invention. A class of luminescently labeled macromolecules designed to sense and report these changes have been termed "fluorescent-protein biosensors". The protein component of the biosensor provides a highly evolved molecular recognition moiety. A fluorescent molecule attached to the protein component in the proximity of an active site transduces environmental changes into fluorescence signals that are detected using a system with an appropriate temporal and spatial resolution such as the cell scanning system of the present invention. Because the modulation of native protein activity within the living cell is reversible, and because fluorescent-protein biosensors can be designed to sense reversible changes in protein activity, it will be appreciated that these biosensors can essentially be reusable. Each of the aforementioned references are incorporated herein in their entirety by reference.

In embodiments of the present invention relating to high throughput screening methods for compounds that inhibit the replication of a flavivirus, such as, for example, WNV, in a cell, a cell array can be used to screen a large amount of compounds in a parallel manner. It will be appreciated that screening large numbers of compounds for activity against a flavivirus with respect to a particular biological function requires preparing arrays of cells for parallel handling of cells and reagents. Standard 96 well microtiter plates which are 86 mm by 129 mm, with 6 mm diameter wells on a 9 mm pitch, are used for compatibility with current automated loading and robotic handling systems. The microplate is typically 20 mm by 30 mm, with cell locations that are 100-200 microns in dimension on a pitch of about 500 microns. Methods for making microplates are described in U.S. patent application Ser. No. 08/865,341, incorporated by reference herein in its entirety. Microplates may consist of coplanar layers of materials to which cells adhere, patterned with materials to which cells will not adhere, or etched 3-dimensional surfaces of similarly pattered materials. For the purpose of the following discussion, the terms 'well' and 'microwell' refer to a location in an array of any construction to which cells adhere and within which the cells are imaged. Microplates may also include fluid delivery channels in the spaces between the wells. The smaller format of a microplate increases the overall efficiency of the system by minimizing the quantities of the reagents, storage and handling during preparation and the overall movement required for the scanning operation.

Those skilled in the art will recognize a wide variety of ways to measure fluorescence, for example, from a well of a microplate in the high throughput cell-based assays of the invention. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), Ann. Rev. of Biophysics and Biomol. Structure 24:405-434; Giuliano et al. (1995), Methods in Neuroscience 27:1-16).

It will be appreciated that any device known in the art for reading and processing the results of the high throughput assays of the present invention, such as the lineage I WNV replicon reporter systems, can be used. For example, in embodiments relating to fluorescence-based reporter, such as GFP or *Renilla* or firefly luciferase, where cell-based assays are carried out in parallel in multi-well plates, a reader system can be used. High throughput 'whole plate' reader systems are well known in the art and are commonly used as a component of a high throughput screening system used to screen large numbers of compounds (Beggs (1997), J. of Biomolec. Screening 2:71-78; Macaffrey et al., (1996) J. Biomolec. Screening 1:187-190). Many of the readers can be fully or partially automated.

The high throughput screening methods of the present invention, in particular, the screening methods to identify inhibitors of a flavivirus, such as WNV, DENV, or another emerging flavivirus, through reporter assays, such as with GFP or *Renilla* or firefly luciferase, may include any known data storage, processing, and retrieval systems known in the art. It will be appreciated that high throughput screening of the invention methods can generate a large volume of data, which must be electronically storable, retrievable, and accessible to maximize the utility of said data.

In one embodiment, the high throughput assay of the invention for the detection of the fluorescence signals emitted from cells infected with the flavivirus reverse genetics systems of the invention, such as the lineage I WNV fully-infectious cDNA or the WNV replicon system engineered with GFP or luciferase, can include an (a) image processor and image capturing device, (b) computing device, which is coupled to the image processor, and (c) a database. The image processor receives information from the image capturing device, which in turn acquires fluorescence signals of the GFP or luciferase expressed in the cells of the cell-based assay. For example, an image capturing device according to the invention could be a digital camera which contains an automatic shutter for exposure control and is adapted to receive fluorescent light from a microscope assembly set for visualizing the cells of the cell-based assays of the invention. Here, the digital camera could be in communication with a computing device, such as a desktop personal computer, via an image processor. The computing device facilitates the user to visualize, manipulate, analyze, render, and process, etc., the data generated by the methods of the present invention. The data can be stored and retrieved in a suitable database, which can be located on a local computing device, such as a computer hard drive, or over a network system on a remotely-located computer.

One of ordinary skill in the art will also appreciate that the data can also be transmitted to another another person, computing device, or destination via any known method of data transfer, including, for example portable storage media, network transfers, or by providing printed copies of data. Thus, oweing to the transferability of the data generated from the methods of the instant invention, especially the high throughput screening assays taught herein, those skilled in the art will appreciate that there can be a cooperation between a plurality of persons or research groups that are distally located from one another. For example, a first research group in a first global location could carry out a first segment of the high throughput methods of the instant invention whereas a second research group in a second global location in coordination therebetween could carry out a second segment of the high throughput methods of the invention. For example, the first segment carried out by a first research group might relate to generating the data from a cell-based screen of the present invention to identify potential anti-flavivirus inhibitors and providing said data to an accessible database. The second segment carried out by the second research group might relate to the acquirement of the data from the database and analyzing said data to indentify and further study potential inhibitors of a flavivirus.

In one embodiment involving fluorescence-related reporters, such as GFP or *Renilla* or firefly luciferase, the invention can be carried out using a microwell format in a microplate. The microplate, such as one having 96-, 384-, or 1536-wells, could be placed in an "XY" microplate reader and the fluorescence signal contained in each of the wells of the microwell plate could be detected by a digital camera and the data sent to a database. A computing device, such as a laptop computer, could retrieve the information from the assay and display the results thereon. Any known software and/or image processing technology is contemplated by the present invention for obtaining the results of the cell-based assays of the present invention, especially the fluorescence-based assays involving GFP or luciferase lineage I WNV reverse genetics systems. Acquiring, processing, and storing of fluorescence-based data and other assay-relevant data from high throughput cell-based screens is known in the art and can be found in U.S. Pat. Nos. 5,989,835, 6,631,331, 6,620,591, 6,633,818, and 6,416,959, wherein each of said patents is incorporated herein by reference in their entirety.

The present invention further contemplates any suitable future-developed instrumentation for measuring, acquiring, detecting, analyzing, processing, and storing the data generated from the screening methods of the instant invention. One of ordinary skill in the art will appreciate that instrumentation and technology to facilitate high throughput assays are continually being developed, such as improved fluorescence readers, robotics, bioinformatics, software, and assay reaction vessels. The present invention contemplates any such method suitable for carrying the instant invention.

In another embodiment, the instant invention provides a full-length cDNA clone of a lineage I WNV or a subgenomic fragment thereof (i.e., a portion of the fill-length cDNA clone) for use in generating an attenuated virus vaccine capable of providing a protective immune response against a flavivirus, e.g., WNV, DENV, or any known or emerging flavivirus. The lineage I WNV cDNA clone or subgenomic fragment thereof can be manipulated genetically using any method of genetic engineering known to one of ordinary skill in the art to construct a suitable genetic variant. Ideally, a live virus vaccine is completely apathogenic but remains highly infectious and replication-competent upon peripheral inoculation and thus efficiently induces a protective immune response. Moreover, the ideal live virus vaccine is incapable of reverting to or evolving into a virulent phenotype. Further, attenuated flaviviruses that might be used as live virus vaccines can be constructed from these infectious cDNA clones.

The development of a vaccine would be an advance in the art, given the lack of suitable anti-WNV therapies available at the present time. More in particular, the development of a lineage I WNV vaccine would advance the art since lineage I WNV is the main human pathogen. One of ordinary skill in the art will appreciate that a virus vaccine can be generated by mutating or otherwise inactivating a parent virus to a degree such that the mutated or inactivated virus is capable of mounting an immune response, but incapable of producing a viral infection in the host. One type of virus vaccine is a "killed virus vaccine", which consists of virus particles that have been chemically treated with formalin or physically treated with heat or irradiation so that they are no longer able to replicate. Some vaccines of this type are influenza, rabies, and the Salk polio vaccines. These vaccines can only be developed from viruses whose nucleic acid can be reliably inactivated. A drawback with this type of vaccine is that a large amount of pathogenic virus is necessarily produced during its manufacture (Parham, P. Immunology. New York: Garland, 2000).

Another type of virus vaccine are "live-attenuated virus vaccines" or "attenuated virus vaccines," which according to an embodiment of the present invention, consists of a live virus, advantageously the full-length lineage I WNV cDNA or subgenomic fragment thereof, that has been mutated such that it has a reduced ability to replicate in human cells and thus, apathogenic, but retain its immunogenicity to a level that is similar or equivalent to the parent virus—therein forming an "attenuated full-length lineage I WNV cDNA or subgenomic fragment therof." It will be appreciated that attenuated virus vaccines are usually more potent at eliciting protective immunity than inactivated virus vaccines because the attenuated virus can usually replicate to a limited extent and thus mimics a real infection. Further, the antigenic proteins of the attenuated virus are more immunogenically authentic than those same antigens of killed-virus vaccnines. One of ordinary skill in the art will further appreciate that growth of the virus in cells of non-human animal species produces attenuated virus. Since the viruses are grown in the non-human hosts, they evolve such that they become less fit for growth in humans, i.e. "attenuated," and more fit for the subject infected host. Some examples of this type of vaccine include the vaccines for measles, mumps, Sabin polio, and yellow fever. Attenuated viral strains can also be produced by random mutagenesis through the natural progression through the human population. As a virus passes through the human population the virus generally diversifies by mutation, sometimes producing a strain with reduced pathogenicity (Parham, 2000; Mandl et al, (1998) J. Virol. 72(3): 2132-2140).

The instant invention also contemplates a vaccine composition comprising the attenuated WNV strains of the invention. The term "vaccine composition" intends any pharmaceutical composition containing an attenuated virus, which composition can be used to prevent or treat a flavivirus infection, especially a WNV infection, in a subject. The compositions of the invention can include any pharmaceutically acceptable carrier known in the art.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor-T cells, and/or cytotoxic T cells and/or γδ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The present invention contemplates the genetic alteration of any suitable region of the WNV genome to achieve an attenuated WNV virus that is apathogenic, but capable of eliciting a protective immune response. For example, flaviviruses have non-coding regulatory sequences at the 5' and 3' ends that are responsible for replication and processing of viral particles. These sequences do not harbor many conserved motifs and are capable of forming secondary and tertiary structures, which are recognized not only by proteins encoded by the viral genome, but also host cell proteins that allow for proper translation of the viral RNA. The 5' and 3' ends of the flavivirus genome contain what is called a "cyclization sequence", which when deleted, abolishes replication of the viral genome. The 3' end in particular contains sequences that form hairpin and stem-loop structures, and has been shown to affect replication in TBEV. Mutations in these regions of the 3' UTR have been successfully incorporated into full-length infectious clones of TBEV, resulting in live, attenuated viruses proficient for immunogenicity, but which lack wild-type replicative activity (Mandl et al, 1998). Similarly, mutations in the structural gene encoding for the capsid protein also produce similar effects in TBEV (Kofler et al, 2002).

One skilled in the art will appreciate the numerous targets for mutagenesis that have been previously characterized to be successful. Each and every step in the formation of mature virions can be related to the functions of specific proteins and/or regulatory sequences encoded by the viral genome, and these targets can be mutagenized to create viruses which lack pathogenicity, but can mount an antibody response in a host. Potential functional targets include replication, processing of cell-surface antigens such as glycoproteins or capsid proteins, packaging of the viral genome into virion particles, and any host-supplied function relied upon by the infecting virus during the course of its full infection cycle. It is understood that large deletions often yield inactive viruses, thus point mutations or small in-frame deletions are more advantageous. Typically, a functional assay for determining if the mutated virus is indeed attenuated involves transfection of the mutated viral sequence into a suitable host cell line, and measuring or observing the level of cytopathic effects produced in the cell. A measurement of viral replication over time is also used, as well as viral plaque assays. The instant invention relates to production of live, attenuated virus using the full-length infectious clone, which contains a nucleotide sequence encoding a reporter. The reporter would allow for easy detection of infected cells, and since the reporter is indicative of the levels of viral replication, changes in reporter expression will determine if the mutated virus is attenuated. Finally, using various inoculation doses allows the determination of LD50 as a quantitative parameter of virulence and that of ID50 as a quantitative parameter of infectivity. With regard to the development of a safe and efficient vaccine the goal is to get a mutant that shows a large LD50/ID50 ratio (attenuation index) (Kofler et al, J. Virology 2002 76(7):3534-3543).

In another aspect of the present invention, a pharmaceutical composition comprising an attenuated WNV vaccine and/or a antiflaviral chemotherapeutic (e.g. inhibitor) is provided. In a further embodiment, the attenuated WNV vaccine is prepared by genetic engineering of the sequence of the lineage I WNV cDNA such that the resultant RNA transcript produced from the engineered lineage I WNV cDNA directs the replication and packaging of an attenuate WNV variant that is less virulent than, but similarly immunogenic as the parental WNV, i.e., the attenuated WNV will not cause WNV-associated disease, but will be able to provide a protective immune response in a host against a flavivirus, e.g., WNV, DENV, or any other known or emerging flavivirus.

In accordance with the instant invention, the attenuated lineage I WNV vaccine can be used in a therapeutically effective amount in pharmaceutical composition to provide a protective immune response to infections by WNV in humans and animals and to prevent or reduce the transmission of WNV from non-human host animals. One of ordinary skill in the art will understand that, given the close relatedness of WNV and other flaviviruses, such as, DENV and JEV, use of the attenuated WNV vaccine of the present invention can afford immunity to infections by other known or emerging flaviviruses, such as, for example, SLEV, AV, KV, JV, CV, YV, TBEV, DENV-1, DENV-2, DENV-3, DENV-4, YFV and MVEV.

The pharmaceutical compositions comprising the attenuated WNV virus vaccine and/or the antiflaviviral chemotherapeutic of this invention may be in a variety of conventional depot forms. These include, for example, solid, semisolid and liquid dosage forms, such as tablets, pills, powders, liquid solutions or suspensions, liposomes, capsules, suppositories, injectable and infusible solutions. The preferred form depends upon the intended mode of administration and prophylactic application.

Such dosage forms may include pharmaceutically acceptable carriers and adjuvants which are known to those of skill in the art. These carriers and adjuvants include, for example, RIBI, ISCOM, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium trisilicate, polyvinyl pyrrolidone, cellulose-based substances, and polyethylene glycol. Adjuvants for topical or gel base forms may be selected from the group consisting of sodium carboxymethylcellulose, polyacrylates, polyoxyethylene-polyoxypropylene-block polymers, polyethylene glycol, and wood wax alcohols.

The vaccines and chemotherapeutic compositions of this invention may also include other components or be subject to other treatments during preparation to enhance their immunogenic character or to improve their tolerance in patients.

Any pharmaceutically acceptable dosage route, including parenteral, intravenous, intramuscular, intralesional or subcutaneous injection, may be used to administer the vaccine composition. For example, the composition may be administered to the patient in any pharmaceutically acceptable dosage form including those which may be administered to a patient intravenously as bolus or by continued infusion over a period of hours, days, weeks or months, intramuscularly—including paravertebrally and periarticularly—subcutaneously, intracutaneously, intra-articularly, intrasynovially, intrathecally, intralesionally, periostally or by oral or topical routes. Preferably, the compositions of the invention are in the form of a unit dose and will usually be administered to the patient intramuscularly.

The pharmaceutical compostions comprising the attenuated WNV vaccine according to the instant invention may also be administered to any animal, including, but not limited to, horses, cattle, monkeys, birds, pet animals (i.e., "companion animals"), such as dogs, cats, birds, ferrets, hamsters, rodents, squirrels, birds and rabbits, to provide a protective immune response therein against a flavivirus, e.g., WNV, DENV, or any other known or emerging flavivirus, and/or to spread or limit the lateral passage of infection by a flavirus to humans. For example, the pharmaceutical compositions comprising the attenuated WNV vaccine can be combined with animal feed stock and/or water provisions, dog food, cat food, bird food, or rodent food. One of skill in the art will understand this method of administration is sometimes referred to as "bait dropping," in which the pharmaceutical composition is included within the food and/or water of the organism to be vaccinated.

The pharmaceutical compositions comprising the attenuated WNV vaccine of this invention may be administered to the patient at one time or over a series of treatments. The most effective mode of administration and dosage regimen will depend upon the level of immunogenicity, the particular composition and/or adjuvant used for treatment, the severity and course of the expected infection, previous therapy, the patient's health status and response to immunization, and the judgment of the treating physician.

For example, in an immunocompetent patient, the more highly immunogenic the attenuated virus, the lower the dosage and necessary number of immunizations. Similarly, the dosage and necessary treatment time will be lowered if the attenuate virus is administered with an adjuvant. Generally, the dosage will consist of 10 μg to 100 mg of the purified attenuate virus, and preferably, the dosage will consist of 10-1000 μg.

In a preferred embodiment of this invention, the attenuated WNV is administered with an adjuvant, in order to increase its immunogenicity. Useful adjuvants include RIBI, and ISCOM, simple metal salts such as aluminum hydroxide, and oil based adjuvants such as complete and incomplete Freund's adjuvant. When an oil based adjuvant is used, the polypeptide usually is administered in an emulsion with the adjuvant.

In yet another embodiment of the instant invention, a method for treating an infection by a flavivirus, e.g., WNV, DENV, or any other known or emerging flavivirus, is provided that combines the steps of first, identifying a antiflaviviral chemotherapeutic in accordance with the methods of the instant invention, and second, administering the antiflaviviral chemotherapeutic in a therapeutic amount to treat the infection by the flavivirus.

In still another embodiment of the present invention, a method of transferring data is provided wherein an antiflaviviral chemotherapeutic is identified in accordance with the methods of the instant invention. The invention contemplates that any data generated or collected during the method of identifying the antiflaviviral chemotherapy can be transmitted or transferred to a third party. For example, the data relating to expression levels of a reporter, such as GFP, in cell-based assays using the reverse genetics systems of the instant invention, could be tabulated, acquired and collected for an entire compound library, containing potentially a plurality of flaviviral inhibitors, and then transmitted electronically, for example by email, or over the internet or a network to a third party laboratory, individual, or research group. The data can also be transferred (i.e., posting) electronically to a network, such as the World Wide Web or other global communications networks. One of ordinary skill in the art will appreciate that the third party can utilize the transferred data resulting from the cell-based assays of the invention to provide or facilitate the identification of a flavivirus inhibitor for the pharmaceutical compostions of the instant invention.

Also contemplated by the present invention are databases containing data generated from the methods of the instant invention. One of ordinary skill in the art would recognize that many variations, modifications, and alterations of databases would be useful for storing data generated from the assays of the invention. For example, a database can be provided, which contains all of the data generated for a particular cell line or a particular cell-based assay, the screening of a complete or incomplete compound library, the reporter expression data from a screening method in accordance with the instant invention, or any other type of data generated from the methods of the instant invention, or data generated from the use of the pharmaceutical compositions, such as efficacy data. The invention further contemplates providing access to the database for commercial purposes. Access can be electronic access over a global communications network, such as the World Wide Web. Data from the cell-based assays of the present invention, more in particular, the results of the assays of the flavivirus reverse genetics systems of the present invention, such as, for example, the lineage I WNV fully-infectious cDNA or replicon system engineered with one or more nucleotide sequences encoding a reporter, especially GFP, luciferase, and Neo.

Figure 1:
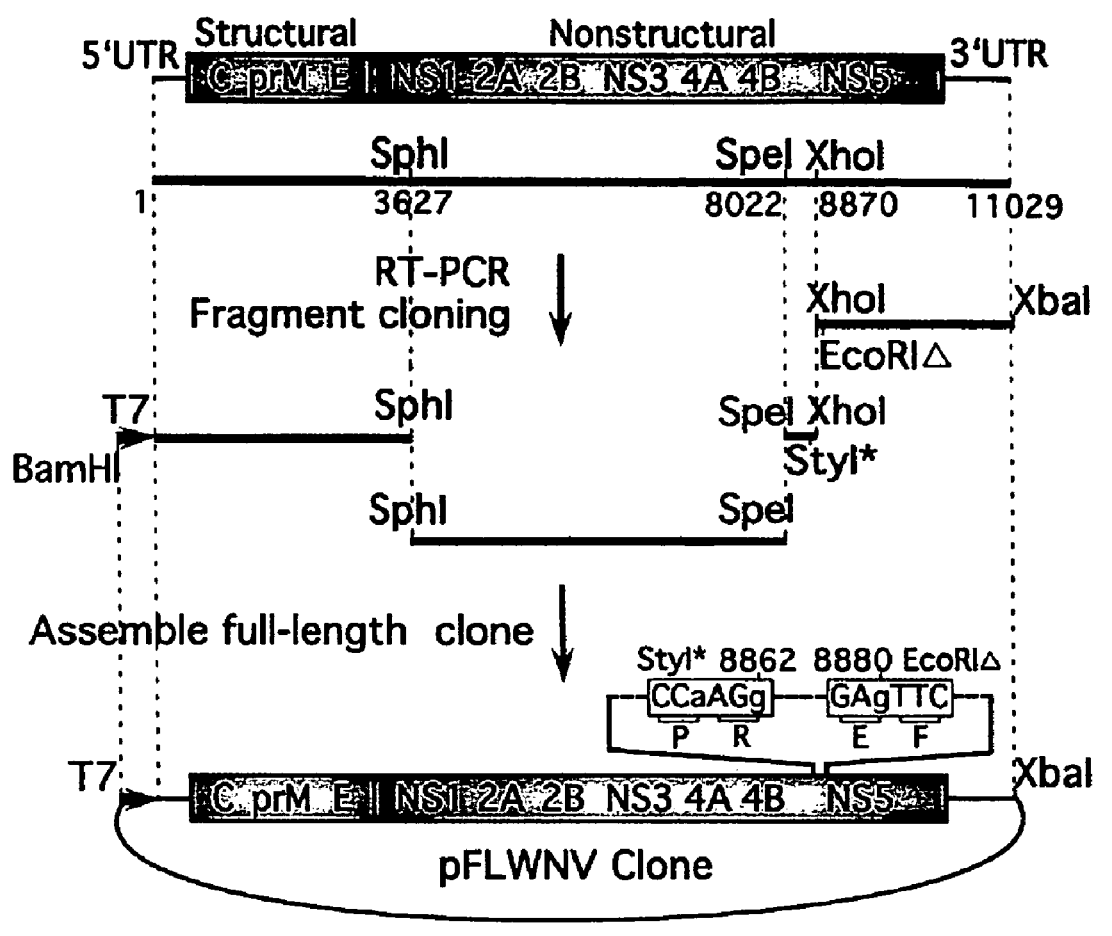

Turning to the figures, FIG. 1 shows the construction of the full-length recombinant cDNA clone of WNV. Genome organization and unique restriction sites as well as their nucleotide numbers are shown at the top of the figure. Four cDNA fragments represented by thick lines were synthesized from genomic RNA through RT-PCT to cover the complete WNV genome. Individual fragments were assembled to form the full-length cDNA clone of WNV (pFLWNV). The complete WNV cDNA is positioned under the control of T7 promoter elements for in vitro transcription. It will be appreciated, however, that other suitable promoters can be used to control the transcription of the WNV cDNA, including, for example, any bacterial, viral, phage, or eukaryotic promoter, especially, SP6 and T3. Three silent mutations (shown in lowercase) were engineered to create a StyI site and to knock out an EcoRI site (triangle) in the NS5 gene to enable discrimination between parental WNV and the cDNA clone by restriction analysis (see FIG. 5). The numbers are the nucleotide positions based on the sequence from GenBank accession No. AF404756 (SEQ ID NO.1).

FIG. 2 shows the sequence differences between the full-length recombinant cDNA clone and the parental WNV strain 3356 (GenBank accession No. AF404756). The data indicate for each affected nucleotide postion, the identity of the nucleotide in the 3356 WNV, the identity of the nucleotide in the recombinant cDNA clone, the amino acid change, and the gene location.

FIG. 3 shows that the in vitro RNA transcription product of pFLWNV (i.e., the recombinant fully-infectious lineage I WNV RNA) behaves the same as genomic WNV RNA purified from the virus as analyzed by formaldehyde-denaturing gel electrophoresis through 1.0% agarose. For in vitro transcription, 5 ug of pFLWNV was linearized with XbaI. Mung bean nuclease (5 U; New England BioLabs) was directly added to the XbaI digestion reaction mixture, and the reaction mixture was further incubated at 30° C. for 30 minutes to remove the single-stranded nucleotide overhang gerated by the XbaI digestion. The linearized plasmids were extracted with phenol-chloroform twice, precipitated with ethanol, and resuspended in 10 ul of RNase-free water at 0.5 ug/ul. The mMESSAGE mMACHINE kit (Ambion, Austin, Tex.) was used to in vitro transcribe RNA in a 20 ul reaction mixture with an additional 2 ul of GTP solution. The reaction mixture was incubated at 37° C. for 2 hours, followed by the addition of DNase I to remove the DNA template. RNA was precitpitated with lithium chloride, washed with 70% ethanol, resuspended in RNase-free water, quantitated by spectrophotometry, and stored at −80° C. in aliquots.

Figure 4:
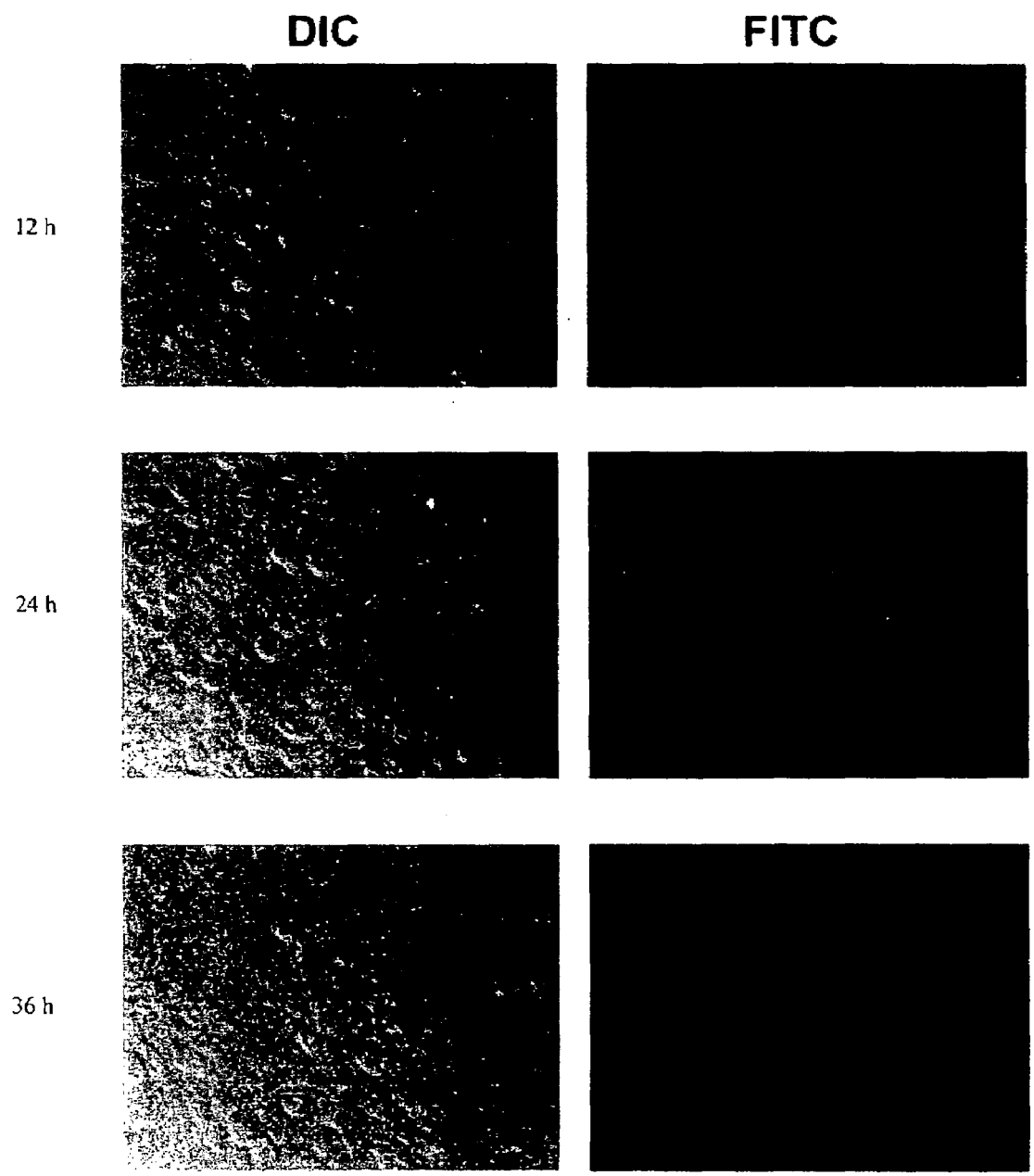
FIG. 4 illustrates the full-infectivity of the in vitro RNA transcription product of pFLWNV (i.e., RNA of the full-length lineage I WNV cDNA clone) in BHK-21 cells by monitoring viral protein expression using indirect immunofluorescence analysis (IFA). BHK-21 cells transfected with full-length WNV RNA transcript were analyzed by IFA at 12, 24, and 36 hours posttransfection. Photomicrographs were taken at magnifications of ×400. The left and right panels represent the same field of view for each time point. The left panels were visualized with differential interference contrast (DIC), and the right panels were visualized with a fluorescein isothicyantate (FITC) filter set.

FIG. 4 shows that the in vitro RNA transcription product of pFLWNV (i.e., recombinant viral RNA) is fully infectious in BHK-21 cells by monitoring viral protein expression using indirect immunofluorescence analysis (IFA). BHK-21 cells transfected with full-length WNV RNA transcript were analyzed by IFA at 12, 24, and 36 hours posttransfection. Photomicrographs were taken at magnifications of ×400. The left and right panels represent the same field of view for each time point. The left panels were visualized with differential interference contrast (DIC), and the right panels were visualized with a fluorescein isothicyantate (FITC) filter set. For the IFA, WNV immune mouse ascites fluid and goat anti-mouse immunoglobulin G antibodies conjugated with FITC were used as primary and secondary antibodies, respectively.

FIG. 5 shows that the virus recovered from cells transfected with the in vitro RNA transcription product of pFL-WNV (i.e., recombinant viral RNA) were not parental virus contamination. To distinguish the recombinant viral RNA from the parental viral RNA, a StyI site was created in, and an EcoRI site was removed from, the NS5 gene of the recombinant virus to serve as genetic markers. A 388-bp fragment (from nt 8706 to 9093) spanning the StyI or EcoRI site was amplified through RT-PCR from RNA extracted from either recombinant virus or parental virus. The RT-PCR fragments were subjected to StyI and EcoRI digestion.

The figure demonstrates that the 388-bp fragment derived from recombinant virus is cleaved by StyI but not by EcoRI, whereas the RT-PCR fragment amplified from parental viral RNA is cleaved by EcoRI but not by StyI. The predicted sizes of the resulting restriction fragments following digestion with StyI or EcoRI are shown in (A). The actual electrophoretic pattern of restriction fragments following StyI and EcoRI digestion of both the recombinant and the parental WNV RNA is shown in (B). The pattern of restriction fragments shown in the gel (B) are consistent with the predicted sizes of restriction fragments in (A) thereby demonstrating that the recombinant virus isolated from the transfected cells is not parental virus contamination. As a negative control, no RT-PCR products were detected from the extracted supernatant collected from cells 5 days after transfection with a mutant RNA containing a deletion of the 3'-terminal 199 nt of the WNV genome (lane 9, 3' dltn). A 100-bp ladder was loaded on lanes 1, 5, and 10 as a standard.

FIG. 6 shows that the plaque morphology of Vero cells infected with the parental WNV and Vero cells transfected with recombinant fully-infectious WNV RNA were identical. (A) shows the plaque morphology of Vero cells in six-well plates infected with 100 plaque-forming units (PFU) of patental WNV 3356 (GenBank accession no. AF404756). (B) shows the plaque morphology of Vero cells infected with 100 PFU of the recombinant WNV fully-infectious RNA derived from pFLWNV of FIG. 1. The plaques of both (A) and (B) are 3 days postinoculation and were stained for 24 hours with neutral red to visualize the plaques.

FIG. 7 shows that the growth kinetics of recombinant fully-infectious and parental WNV in two different cells lines are similar. The growth kinetics of recombinant and parental viruses was compared at high and low multiplicity-of-infections (MOIs) on BHK-21 or *Aedes albopictus* C6/36 cells ("C6/36 cells"). Growth in BHK-21 cells is compared in (A). Growth in C6/36 cells is compared in (B). Viruses were inoculated at an MOI of 5.0 (filled symbols) or an MOI of 0.05 (open symbols) in triplicate in 12-well plates. Recombinant virus is designated by squares along a solid line. Parental virus is designated by triangles along a dashed line. Error bars represent +/− standard deviation of triplicate wells. Dotted line indicates the limit of detection of 500 PFU/ml.

FIG. 8 depicts the strategy of lineage I WNV replicon construction and schematic drawings of the constructed replicons. The WNV genome is shown in (A) along with restriction sites used for cloning. The numbers referring to nucleotide positions are based on the sequence of WNV strain 3356 (Accession No. AF404756). The dotted lines and dotted open boxes refer to an in-frame deletion in the structural region of C-prM-E. All replicons depicted in (B) contain the identical in-frame deletion of the structural region. Recombinant replicons contain silent nucleotide changes to generate a StyI site and to eliminate an EcoRI site. The nucleotide sequences encoding GFP and Neo reporters, along with an upstream IRES regulatory sequence, was engineered into the 3' untranslated region of WNV at the NsiI site. The IRES-GFP cassette region was cloned in accordance with the direction of transcription of the WNV sequence (+GFPRep; "plus-sense") and in the opposite direction (−GFPRep; "minus-sense") as a negative control. Further, the IRES-Neo cassette was clone in the plus-sense (NeoRep).

FIG. 9 shows (A) the strategy of replicon RNA transcription and (B) electrophoretic analysis of full length WNV genome RNA compared with the replicon variants of FIG. 8. Transcription of WNV replicon plasmids was designed to produce replicon RNA with an authentic 3' viral end and an extra nonviral guanine at the 5' end. Formaldehyde denaturing agarose gel electrophoresis compares the mobility of full length WNV genomic transcripts to transcribed replicons.

FIG. 10 depicts indirect immunofluorescence analyses of BHK-21 cells transfected with replicon RNA at various time points post-transfection. WNV immune mouse ascites fluid and FITC-conjugated goat anti-mouse antibodies were used as primary and secondary antibodies, respectively. Cells transfected with a replicon containing a terminal 597-nt deletion of the 3' UTR was used as a negative control.

FIG. 11 shows 5' nuclease RT-PCR analysis of WNV RNA. A standard curve of real-time RT-PCR was generated to demonstrate replicon RNA quantitation in transfected cells. Threshold cycles ($C_T$) were graphed versus the log of the titrated amount of virus (PFU) (A). (B) shows the quantitation of viral RNA during WNV infection. BHK-21 cells were infected with WNV at an MOI of 1 and harvested at the indicated time points post-infection. Extracted RNAs were quantitated by real-time RT-PCR based on polarity of the viral RNA transcripts. The replicon RNAs were quantitated based on polarity in (C). BHK-21 cells were transfected with replicon RNAs and harvested at the indicated time points. One representative experiment of two is shown.

FIG. 12 demonstrates RNA replication in cells transfected with replicon is not derived from parental viral contamination. (A) shows a diagram of fragments generated from RT-PCR, followed by restriction analysis, between parental virus and replicon RNA. Agarose electrophoresis shown in (B) depicts restricted fragment sizes consistent with the expected fragment sizes depicted in (A). As a negative control, RNA corresponding to a replicon containing a 3' UTR deletion was used. The 1-kb plus ladder was used as a standard.

Figure 13:
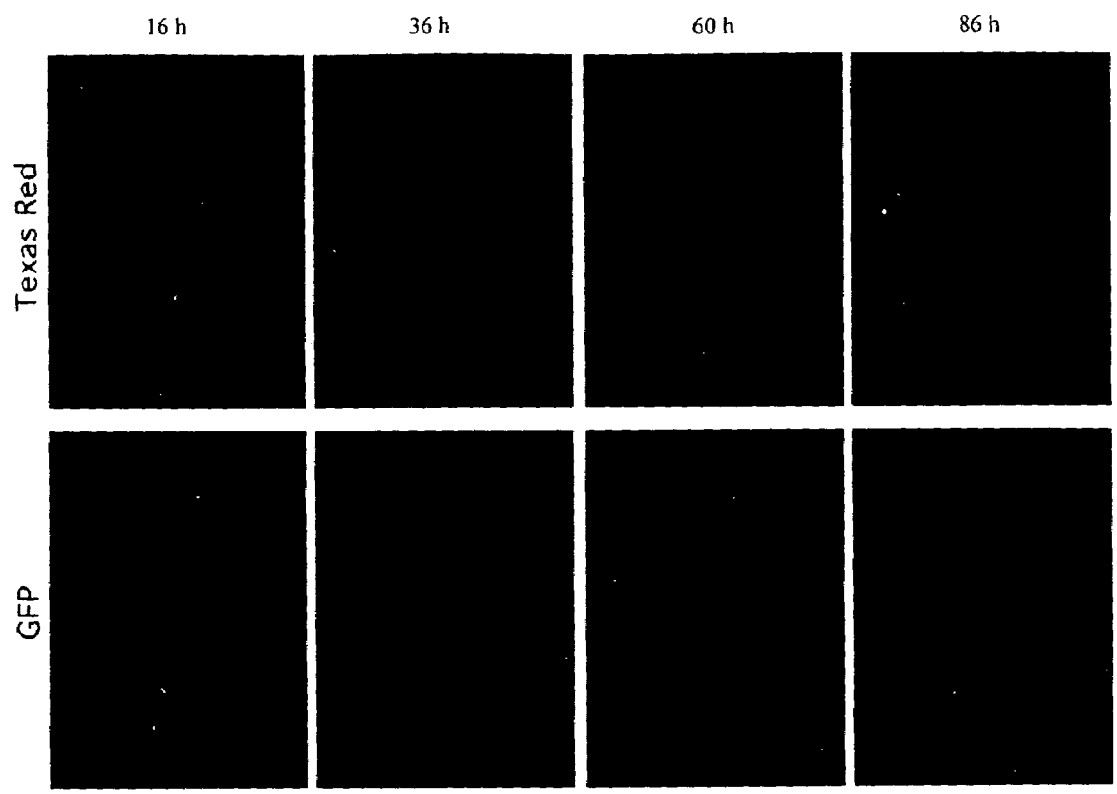
FIG. 13 shows expression of the GFP reporter gene in the WNV replicon. BHK-21 cells were transfected with the +GFPRep and monitored for both GFP expression (left panels) and synthesis of viral proteins by IFA (right panels) at indicated time points post-transfection in (A). (B) depicts the colocalization of cells expressing both GFP and viral proteins.

FIG. 13 shows expression of the GFP reporter in cells infected with GFP-engineered WNV replicon. BHK-21 cells were transfected with the +GFPRep (i.e., the lineage I WNV replicon engineered with a GFP gene) and monitored for both GFP expression (left panels) and synthesis of viral proteins by IFA (right panels) at indicated time points post-transfection in (A). (B) depicts the colocalization of cells expressing both GFP and viral proteins.

Figure 14:
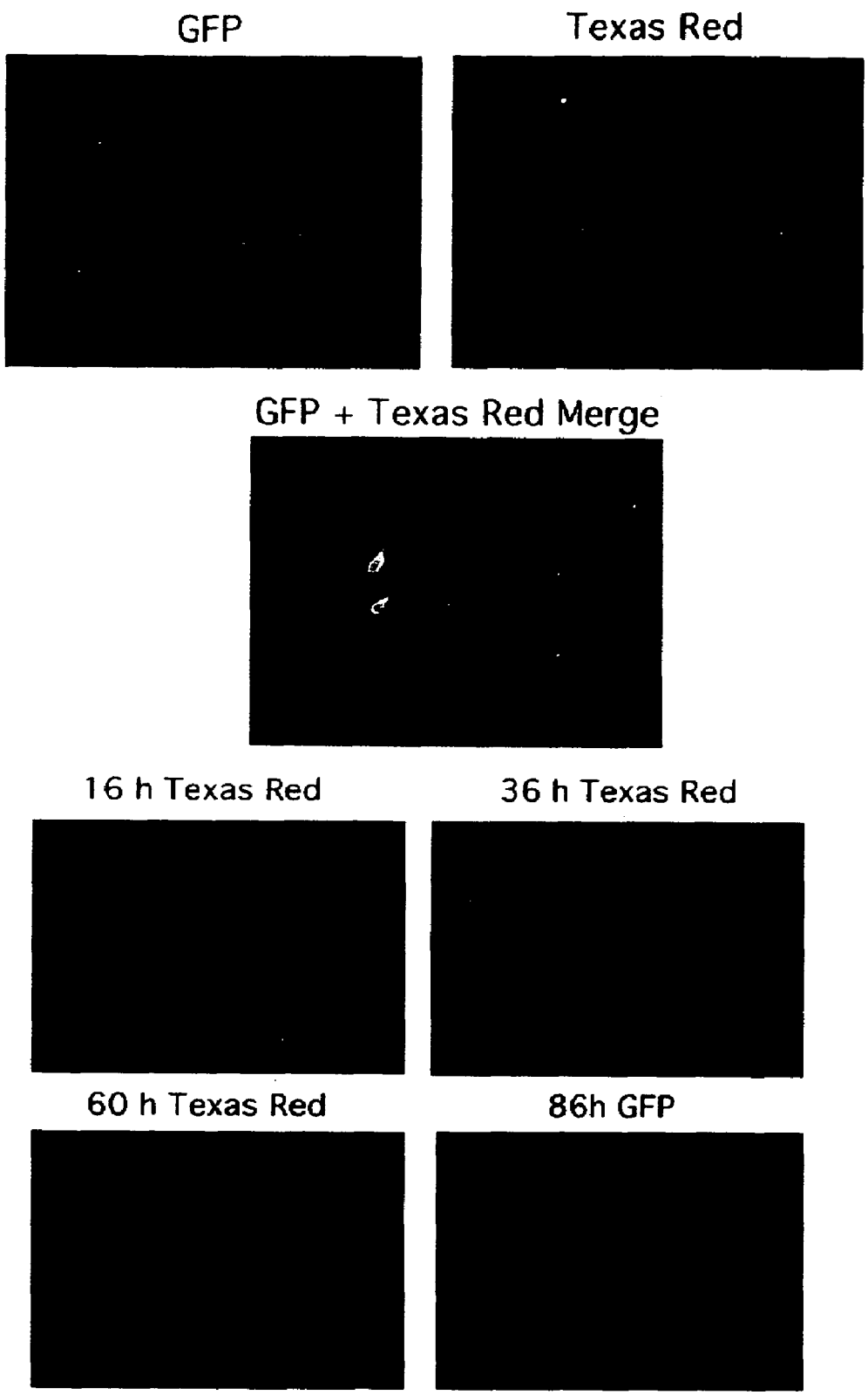
FIG. 14 demonstrates that cells transfected with replicons containing a GFP reporter gene positioned in the minus-sense orientation do not express GFP. Cells were detected at 36 and 60 h post-transfection. Both GFP signals and viral proteins were monitored.

FIG. 14 demonstrates that cells transfected with replicons engineered with a nucleotide sequence encoding a GFP reporter positioned in the minus-sense orientation (−GFPRep) do not express GFP. Cells were detected at 36 and 60 h post-transfection. Both GFP and viral proteins were monitored.

FIG. 15 shows selection of cells containing persistently replicating WNV replicons. BHK-21 cells were transfected with NeoRep (i.e., the lineage I WNV replicon engineered with a neo, neomycin resistance gene according to FIG. 8) and selected by G418 ("Geneticin") resistance. The resulting cells were subjected to IFA to monitor viral protein expression and monitored for CPE by phase contrast or differential interference contrast (DIC) microscopy. (A) shows cells that were cultured in the absence of G418 selection. (B) shows cells that were cultured in the presence of G418 for 15 days (passage 2) and 40 days (passage 8), demonstrating persistent expression of viral proteins and lack of apparent morphological changes.

Figure 16:
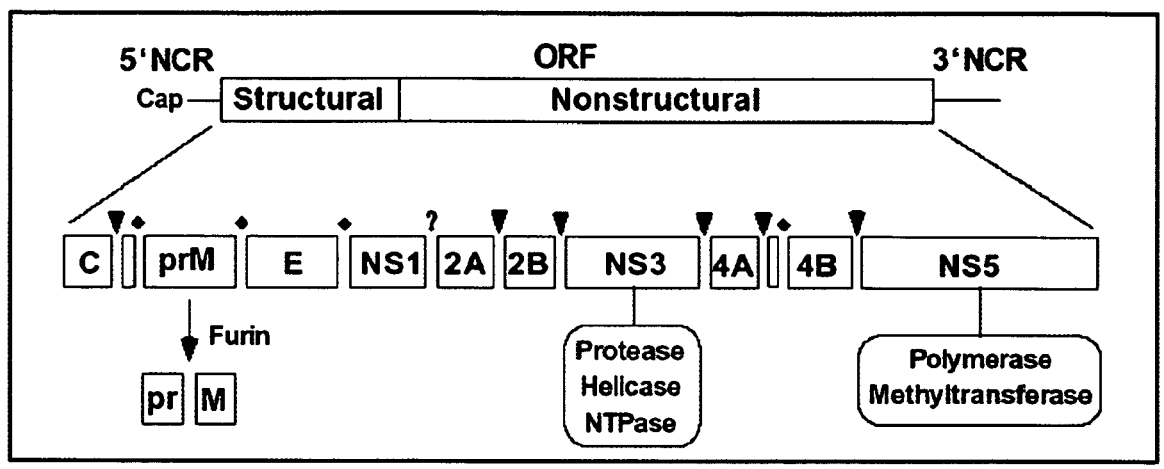
FIG. 16 shows a schematic of the flavivirus genome structure.

FIG. 16 shows a schematic of the flavivirus genome structure. The flavivirus genome is approximately 11 kb in length. The genomic RNA consists of a 5' non-coding region (5' NCR), a single open reading frame (ORF), and a 3' NCR. The single ORF encodes a long polyprotein that is processed into 10 viral proteins, 3 structural proteins and 7 non-structureal proteins. Cleavage sites for host signalase, viral serine protease, and unknown protease are indicated by diamonds, arrows and a question mark, respectively. The prM protein is processed to pr and M protein during late virus maturation by the host protease furin. The enzymatic activities of NS3 and NS5 proteins are indicated.

FIG. 17 shows a schematic contrasting the immature and mature flavivirus virions. The heterodimers of prM and E are shown on the left (immature virion) and homodimers of E, following cleavage of prM, on the right (mature virion). The icosahedral nucleocapsid is shown as enclosed by the lipid bilayer envelope of the virus.

Figure 18:
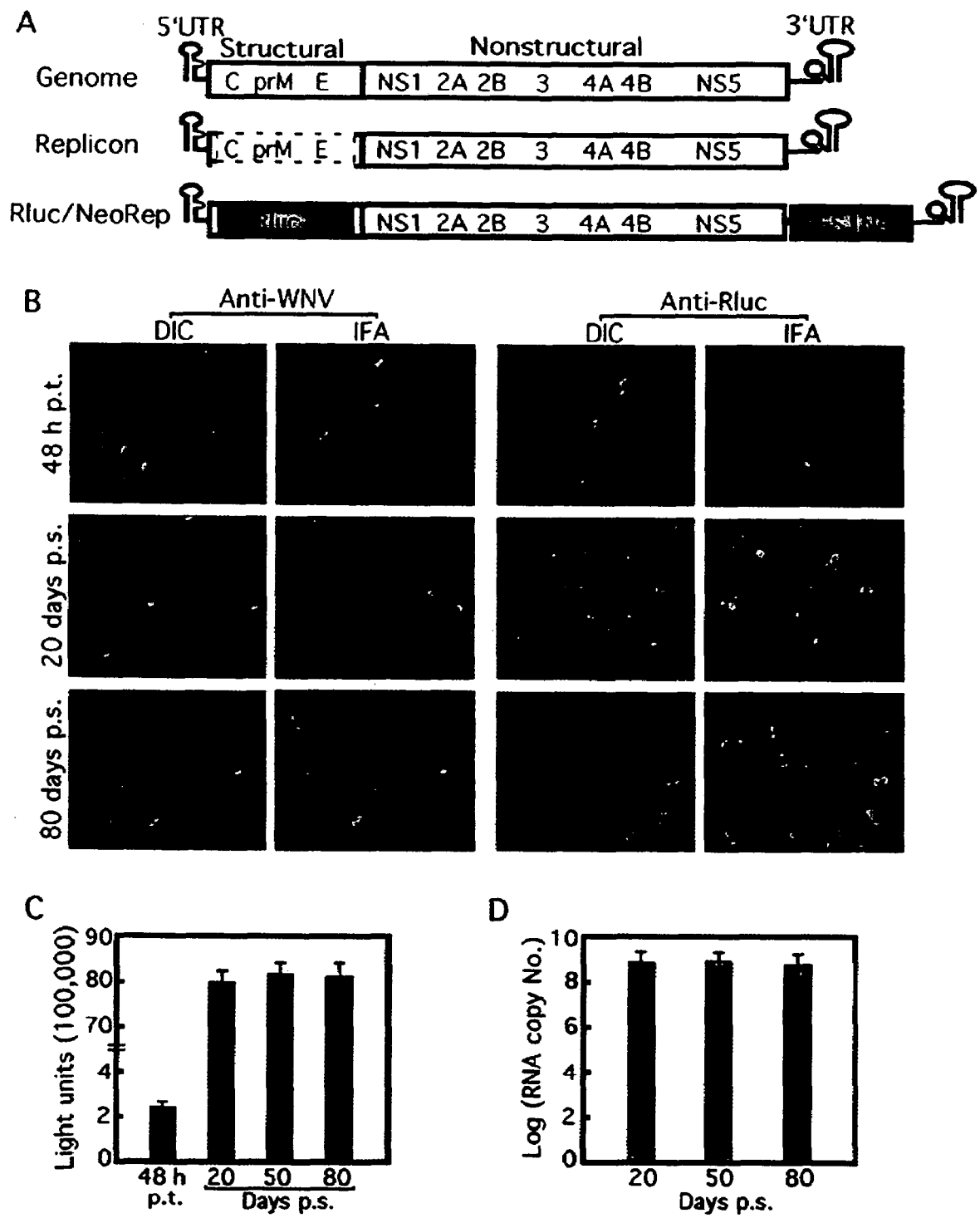
FIG. 18 shows the construction and characterization of a stable cell line containing a dual reporter replicon of lineage I WNV containing nucleotide sequences encoding the reporters neomycin phosphotransferase (Neo) and *Renilla* luciferase (Rluc).

FIG. 18 shows the construction and characterization of a stable cell line containing a dual reporting replicon of WNV. (A) shows the WNV genome, subgenomic replicons, and dual reporting replicons. Compared with the full-length WNV genome, the wild-type replicon contained an in-frame deletion of the structural region (dotted open box) from nt 190 to 2379. An AflII site was generated (indicated by #) at the junction of the deletion by a silent coding mutation G186T (in lower case). In Rluc/NeoRep, the Rluc was fused in-frame with the ORF in the position where the structural genes were deleted; the IRES-Neo fragment was inserted into the NsiI site (nt 10436) in the upstream region of the 3' UTR of the replicon. Rluc/NeoRepNS5mt contains a frameshift insertion of a nucleotide U between nt 8027 and 8028 to knock out the active site of the NS5 RdRp gene. The numbering of the nt position is according to GenBank accession no. AF404756 (see FIG. 20; SEQ ID NO.1). The drawing is not to scale.

(B) shows the IFA of cells at 48 h post-transfected (p.t.) with Rluc/NeoRep (top panel), and IFA of Rluc/NeoRep-transfected cells at 20 and 80 days post-selection (p.s.) under G418 (lower two panels). The same field as imaged by differential interference contrast (DIC) and IFA staining with Texas red is presented, to show percentage of cells containing the replicating Rluc/NeoRep. The expression of viral and Rluc proteins is as indicated. In performing the IFA, approximately $10^5$ cells were seeded into 4-chamber slides (Nalge, Naperville, Ill.), reacted with WNV immune mouse ascites fluid (1:100 dilution; ATCC, Manassas, Va.) or with a mouse anti-Rluc monoclonal antibody (1:200 dilution; Chemicon, Temecula, Calif.) as a primary antibody, and further reacted with goat anti-mouse IgG conjugated with Texas red (1:400 dilution; KPL, Gaithersburg, Md.) as a secondary antibody.

(C) shows Rluc activity in cells at various time points p.t. or p.s. as indicated. Rluc activities derived from the Rluc/NeoRep-containing cells are represented by filled bars. Background level of Rluc activity from cells at 48 h after transfection with the replication-defective replicon, Rluc/NeoRepNS5mt, is indicated by a hollow bar. Signals from $4 \times 10^4$ equivalent cells were presented for the Rluc quantification.

(D) shows WNV replicon RNA copy numbers in cells at various time points p.s. as indicated. Signals from $10^5$ equivalent cells were estimated for the Rluc/NeoRep RNA quantification.

Figure 19:
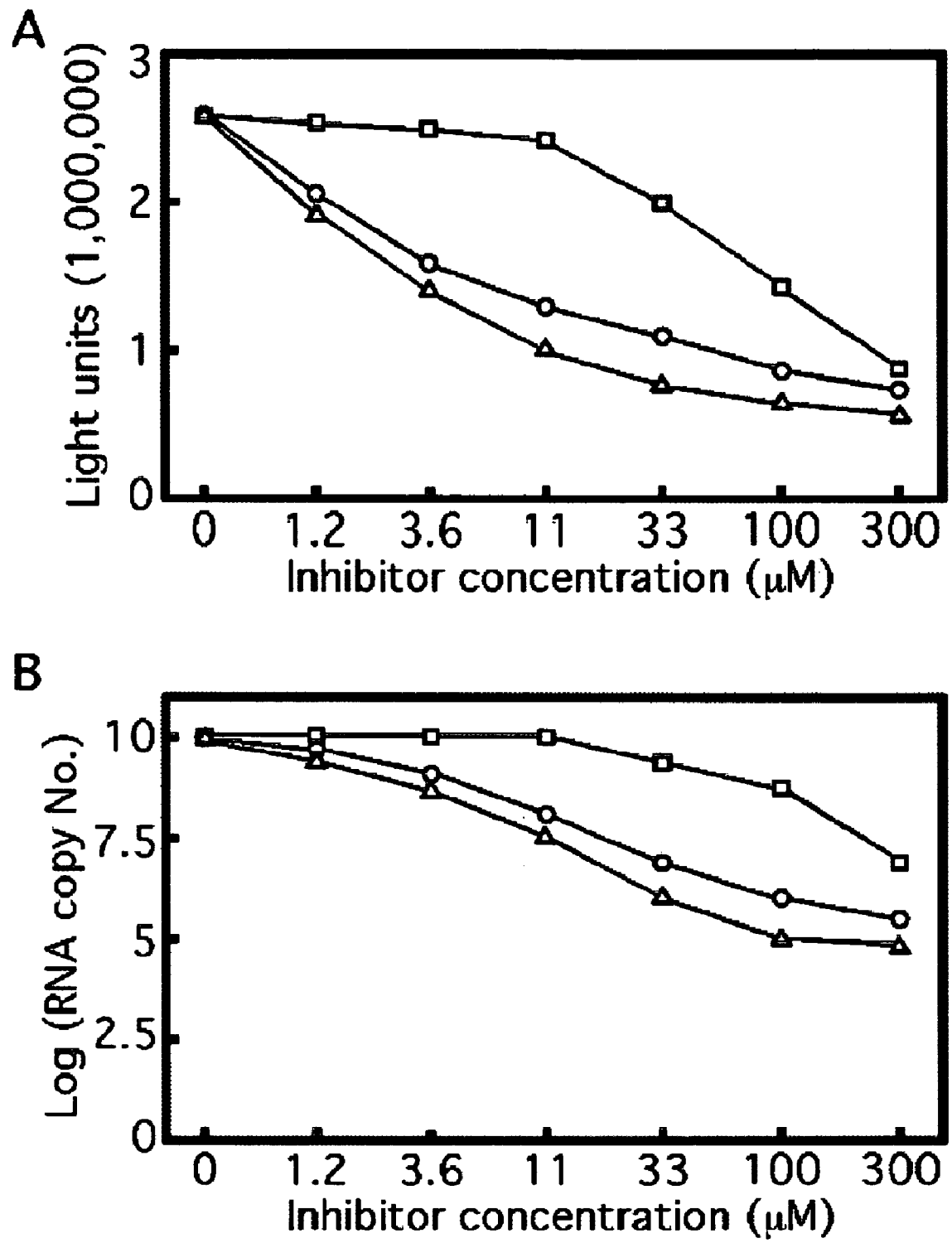
FIG. 19 demonstrates the use of a cell line containing a lineage I WNV replicon engineered with nucleotide sequences encoding the reporters *Renilla* luciferas (Rluc) and neomycin phosphotransferase (Neo) as a high-throughput assay for antiviral drug discovery. Replicon-containing cells were treated with mycophenolic acid (triangle), 6-azauridine (circle), and ribavirin (square) at indicated concentrations for 24 h. The inhibition of viral replication by each compound was measured by the Rluc activity (A) and the replicon RNA copy number (B). One representative experiment of three is shown.

FIG. 19 demonstrates that the reporting cell line containing Rluc/NeoRep can be used as a high-throughput assay for antiviral drug discovery. Replicon-containing cells were treated with mycophenolic acid (triangle), 6-azauridine (circle), and ribavirin (square) at indicated concentrations for 24 h. The inhibition of viral replication by each compound was measured by the Rluc activity (A) and the replicon RNA copy number (B). One representative experiment of three separate experiments is shown.

A better understanding of the present invention and of its many advantages will be had from the following examples, which further describe the present invention and given by way of illustration. The examples that follow are not to be construed as limiting the scope of the invention in any manner. In light of the present disclosure, numerous embodiments within the scope of the claims will be apparent to those of ordinary skill in the art.

EXAMPLES

Example 1

Generation of a Full-Length Infectious cDNA Clone of Lineage I West Nile Virus

BHK-21 (baby hamster kidney cells, ATCC CCL-10; Manassas, Va.) cells were grown in Dulbecco's modified minimal essential medium, supplemented with 10% fetal bovine serum, 0.1 mM nonessential amino acids, 10 U/ml penicillin, and 10 µg/ml streptomycin. Cells were infected with parental WNV at a multiplicity of infection (MOI) of 0.05, which was isolated from the kidney of an American crow collected in October 2000 from Staten Island, N.Y. Virus was harvested from the cell culture medium at 36 hours post-infection. Genomic RNA was extracted from the cell culture medium using the RNeasy RNA extraction kit (Qiagen, Valencia, Calif.). cDNA fragments, which in total encompassed the entire WNV genome were synthesized from the isolated genomic RNA by reverse transcription-polymerase chain reaction (RT-PCR) using ThermoScript reverse transcriptase (Gibco BRL, Rockville, Md.).

To select for the appropriate plasmid vector and host bacterial strain, different vectors and bacterial hosts were tested for stability. Ultimately, plasmid pBR322 and *E. coli* HB101 (Gibco BRL) were chosen for cloning the WNV genome. Plasmid pBR322 was modified by replacing the SphI-EcoRI fragment in the tetracycline resistance gene with a pair of complementary oligonucleotides to create a new multiple cloning site containing the unique restriction sites BamHI, SphI, SpeI, XhoI, and XbaI. Following this, substituting a cytosine (C) for a guanine (G) nucleotide mutated the original SphI site in pBR322. This modified plasmid vector, known as pBRLinker, was used as the cloning vector in subsequent experiments.

Plasmids were electroporated into *E. coli* HB101 using a GenePulser apparatus (Bio-Rad, Hercules, Calif.). Cloning procedures for bacterial propagation had higher success rates when performed at room temperature than did those performed at 37C. All constructs containing inserts greater than 3 kb were propagated at room temperature, however it was also shown that propagation of the clones at room temperature was not necessarily essential once the clones had been constructed. Each intermediate cloning product was verified by sequence analysis (Applied Biosystems, Foster City, Calif.) before it was used in subsequent cloning steps. All restriction enzymes were obtained from New England Biolabs (Beverly, Mass.).

FIG. 1 shows the overall scheme of the cloning strategy. The primers used to generate individual fragments are listed in Table 1.

The full-length cDNA clone was constructed in four steps: 1) A fragment from SpeI to XhoI was amplified using primers designated 8016V and 8881C, and cloned into their respective restriction sites in pBRLinker, resulting in plasmid pSpe-Xho. To distinguish between the parental virus from the recombinant virus, a StyI site (underlined sequence) was engineered in primer 8881C, containing the silent mutations of nucleotide C→alanine (A), and A→G at positions 8859 and 8862, respectively (underlined sequence). 2) Primers 8865V and 11029C amplified a fragment from XhoI to XbaI. This fragment was inserted into the aforementioned pSpe-Xho plasmid to generate clone pSpe-Xba. Primer 8865V contained an A→G substitution at nt 8880 (underlined sequence). This mutation removed an EcoRI site within the sequence of the parental virus. 3) Primers 3286V and 8804C amplified a fragment from SphI to SpeI. This fragment was inserted into pBRLinker, resulting in pSph-Spe. The fragment from SphI to SpeI was then subcloned into pSpe-Xba to yield pSph-Xba. 4) A cDNA fragment from BamHI to SphI was cloned into the plasmid pSph-Xba into their respective restriction sites. Primer 1V contained sequences for the T7 promoter (italicized sequence), with a BamHI site appended to the 5' end of the sequence (lower case, underlined sequence). The resulting plasmid, designated pFLWNV, contained the complete WNV cDNA under control of the T7 promoter.

Example 2

Comparison of Parental WNV RNA with Recombinant WNV RNA by Sequencing and Gel Electrophoresis In vitro transcription was carried out on pFLWNV, prepared according to Example 1, using T7 RNA polymerase to generate RNA ("recombinant RNA") from the full-length recombinant WNV cDNA sequence of the plasmid. Form-

TABLE 1

Oligonucleotides used to construct the full-length cDNA of WNV

| Primer | Primer Sequence | Amplified fragment |
|---|---|---|
| 1V | CAAA*GGATCC*TAATACGACTCACTATAGAGTAGTTCGCCTGTGTGAGCTGA (*BamHI* underlined, T7 promoter italicized) (SEQ ID NO.3) | BamHI - SphI |
| 3839C | ATGTTCTCCTGGTTGGTCCA (SEQ ID NO.4) | BamHI - SphI |
| 3286V | GTAGAGATTGACTTCGATTAC (SEQ ID NO.5) | SphI - SpeI |
| 8804C | CGTACTTCACTCCTTCTGGC (SEQ ID NO.6) | SphI - SpeI |
| 8016V | GCCCCAACTAGTGCAAAGTTATGGATGGAAC (SEQ ID NO.7) | SpeI - XhoI |
| 8881C | ATTCTT*CTCGAG*AGCACAT*CCTTGG*ACGTTTTTCTCTGGCC (*XhoI* italicized, *StyI* underlined) (SEQ ID NO.8) | For engineering a StyI site within SpeI - XhoI fragment |
| 8865V | GTGCT*CTCGAGAG*GAGTTCATAAGA (*XhoI* italicized, *EcoRI*Δ underlined) (SEQ ID NO.9) | For knocking out an EcoRI site within XhoI - XbaI fragment |
| 11029C | AACAA*TCTAGA*GATCCTGTGTTCTCGCACCAC (*XbaI*) (SEQ ID NO.10) | XhoI - XbaI | aldehyde-denaturing 1.0% agarose gel electrophoresis was carried out on both the recombinant RNA and the parental WNV RNA genome. The result revealed that the recombinant RNA had an identical mobility pattern to that of the genomic RNA extracted from parental WNV (see FIG. 3).

Further, the sequence analysis of the full-length cDNA clone revealed 11 nucleotide changes when compared with the parental viral sequence (see FIG. 2). All but one mutation were silent mutations. The only exception was a thymine (T)→C mutation at nt 7826, which resulted in a conservative change from a valine to an alanine residue. Three nucleotide changes were intentionally engineered for use as genetic markers to distinguish the recombinant virus from the parental viral stock. As detailed above, nt 8859, corresponding to C, was changed to A and nt 8862, corresponding to A, was changed to G. These two mutations resulted in a StyI site, which is not present in the parental genome. Nucleotide 8880, corresponding to an A→G mutation, abolished the parental EcoRI site in the recombinant viral genome. Other mutation in the cDNA clone may derive from the quasispecies of the original virus stock because the parental virus was not plaque purified. It is also possible that some of the mutations occurred during the cloning procedures.

Example 3

Production of Highly Infectious RNA Transcripts from WNV cDNA

Plasmid pFLWNV was amplified in the *E. coli* strain HB101 and purified by column chromatography using the MaxiPrep kit (Qiagen). The purified plasmid DNA was linearized with XbaI and the resultant single-stranded nucleotide overhang was eliminated by digestion with mung bean nuclease (New England Biolabs). Subsequently, the linearized plasmid was extracted twice with phenol-chloroform and ethanol-precipitated. Finally, the purified DNA was resuspended in 10 µof RNase-free water and quantitated by spectrophotometry.

The mMessage mMACHINE kit (Ambion, Austin, Tex.) was used to carry out an in vitro transcription reaction in a 20 µl reaction volume supplemented with 2 µl of GTP solution (optimized 4/3 ratio of methylated cap analogue to GTP). The reaction was allowed to proceed for 2 hours at 37° C., followed by addition of DNase I to remove residual template DNA. The synthesized RNAs were precipitated in lithium chloride, washed in 70% ethanol, resuspended in RNase-free water, and quantitated by spectrophotometry. Approximately 30 to 40 µg of RNA was generated from 2 µg of DNA template in a 20 µl reaction mixture. Increasing the ratio of cap analogue to GTP substantially reduced the RNA yield.

To measure infectivity, 10 µg of RNA transcript was electroporated at a confluency of $10^7$ cells in 0.8 ml of cold phosphate-buffered saline (PBS), pH 7.5, in 0.4-cm cuvettes using the Gene Pulser apparatus at settings of 0.85 kV and 25 µF, pulsing three times with no pulse controller. After a 10-minute recovery, cells were mixed with media and incubated in a T-75 flask at 5% $CO_2$ at 37° C. until cytopathic effects (CPE) were observed. Apparent CPE were observed in cells on day 3 posttransfection. The cell culture medium was harvested, clarified by centrifugation at 10,000×g, and viral titer was determined using Vero cells (ATCC CCL-81) in plaque assays. High titers of $1\times10^9$ to $5\times10^9$ plaque forming units (PFU)/milliliter were reproducibly obtained, indicating that the resulting recombinant RNA was highly infectious.

Example 4

Indirect Immunofluorescence Analysis to Authenticate Viral Protein Expression with Recombinant WNV RNA Transcripts Indirect immunofluorescence analysis (IFA) was used to monitor viral protein expression in BHK-21 cells transfected with recombinant WNV RNA transcripts (see FIG. 4). Cells were plated on coverslips and fixed with 3.7% paraformaldehyde in PBS pH 7.5. The fixed cells were incubated in methanol for 30 minutes at −20° C. The fixed cells were washed with PBS and incubated at room temperature for 45 minutes in WNV immune mouse ascites fluid (1:100 dilution; ATCC). The secondary antibody used was goat anti-mouse immunoglobulin G conjugated with fluorescein isothiocyanate (FITC) at room temperature for 30 minutes (1:100 dilution; KPL, Gaithersburg, Md.). Coverslips were washed of excess antibody, and mounted to a slide using fluorescent mounting medium (KPL). Signals were visualized with a fluorescence microscope equipped with a video documentation system (Zeiss, Thornwood, N.Y.). No IFA staining was observed in cells 12 hours posttransfection. At 24 hours posttransfection, fluorescence was detected in the majority of the cells. The staining intensity varied among the IFA-positive cell population. The fluorescent signal increased, and all cells were IFA-positive at 36 hours posttransfection.

To eliminate the possibility that the positive IFA was merely derived from translation of the transfected RNA rather than from RNA replication in cells, cells were transfected with a mutant RNA containing an expected lethal deletion of the 3'-terminal 199 nt of the genomic RNA. The 3' deletion RNA was synthesized from the cDNA plasmid digested with a WNV-unique DraI site (nt position 10830). No positive IFA staining was detected in cells at any time points posttransfection (data not shown).

These results showed that the positve IFA signals were initially derived from the replication of the recombinant RNA in transfected cells and that progeny virus was subsequently generated and spread to neighboring cells through new rounds of infection.

Example 5

Determination of the Specific Infectivity of In Vitro RNA Transcription Product from the Full-Length Recombinant WNV cDNA The specific infectivity of RNA transcribed from the full-length cDNA clone of pFLWNV was determined in order to evaluate the efficiency of the system. The specific infectivity of RNA was estimated to be $5\times10^4$ to $1\times10^5$ PFU/µg of RNA. Similar specific infectivity was obtained for a mutant RNA containing an extra four nucleotides (5'-CUAG-3') at the 3' end. The mutant RNA was synthesized from the XbaI-linearized DNA template without mung bean nuclease treatment. Genomic RNA purified from virus showed a specific infectivity of $5\times10^5$ to $1\times10^6$ PFU/µg, approximately 10-fold higher than that of transcript RNA. Since uncapped RNA exhibits specific infectivity $10^2$- to $10^3$-fold lower than that of the capped transcript, the discrepancy of infectivity between viral and transcript RNA is most liely due to incomplete capping of the in vitro-transcribed RNA population or to sequence differences, as outlined in FIG. 2.

Example 6

Demonstration of the Stability of Recombinant Full-Length cDNA Plasmid by Multiple Cell Passage The genomic stability of the full-length cDNA clone was tested by amplifying the plasmid pFLWNV in *E. coli* HB101 for six continuous passages. Restriction analysis with StyI and EcoRI determined that the plasmid purified from each of these passages was, in fact, the original pFLWNV. BHK-21 cells transfected with RNA transcripts synthesized from DNA derived from the sixth passage showed specific infectivity and CPE that were indistinguishable from those of the first passage cells, indicating that the cDNA clone was stable (see FIG. 5).

Example 7

Figure 6:
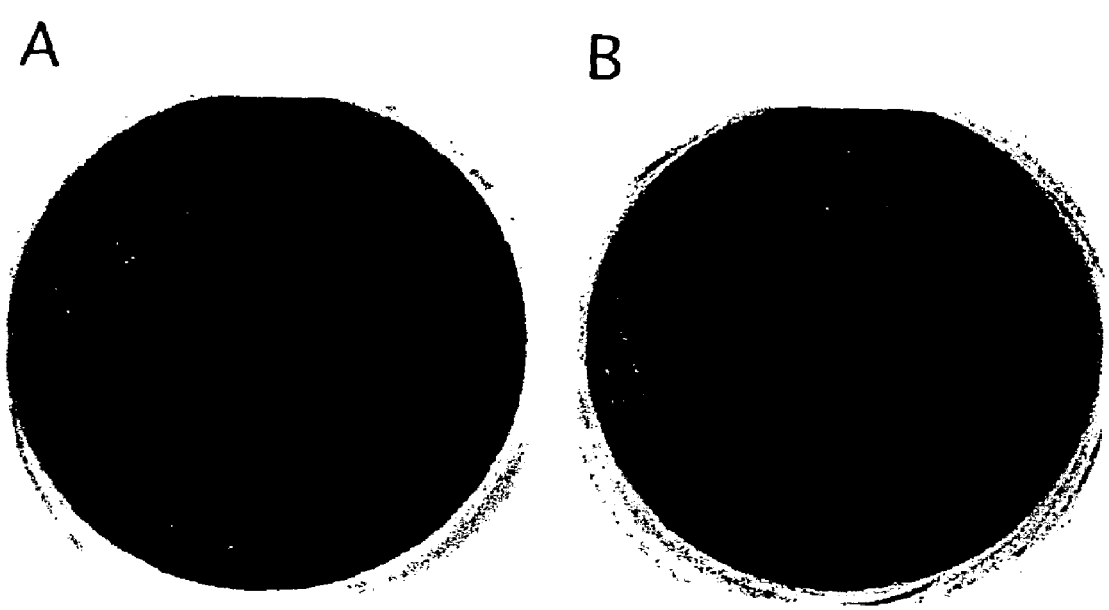
FIG. 6 shows the similarity in plaque morphology of Vero cells infected with either the parental WNV (A) or Vero cells transfected with recombinant WNV RNA transcription product of pFLWNV (B). The Vero cells were infected with either 100 plaque-forming units (PFU) of patental WNV 3356 (GenBank accession no. AF404756) or WNV RNA derived from pFLWNV. The plaques of both (A) and (B) are 3 days postinoculation and were stained for 24 hours with neutral red to visualize the plaques.

Comparison of Plaque Morphologies of Cultured Mammalian and Insect Cells Infected with Either Parental or Recombinant WNV The plaque morphology of Vero cells transfected with recombinant WNV RNA was directly compared with Vero cells infected with the parental viral stock (see FIG. 6) to assess the differences, if any, in the characteristics of virus-produced plaques. Vero cells were maintained in minimal essential medium supplemented with 10% fetal bovine serum, 10 U/ml of penicillin, and 10 µg/ml streptomycin. There were no differences in plaque size or morphology between recombinant and parental viruses, indicating that phenotype, replication, and spread of parental and recombinant viruses were indistinguishable in both mammalian and insect cells.

Similarly, the growth of BHK-21 and C6/36 *Aedes albopictus* cells (ATCC CRL-1660) was monitored (see FIG. 7). Subconfluent cells in 12-well plates were inoculated with either the parental or recombinant WNV at an MOI of 5 or 0.05 in triplicate wells. Virus stocks were diluted in BA-1 (M199-H [Gibco-BRL], 0.05 M Tris pH 7.6, 1% bovine serum albumin (BSA), 0.35 g sodium bicarbonate/liter, 100 U of penicillin/ml, 100 µg of streptomycin/ml, and 1 µg of amphotericin B [Fungizone]/ml). Attachment was allowed to proceed for 1 hour under 5% $CO_2$ at 37° C. for BHK-21 cells, and under 5% $CO_2$ at 28° C. for C6/36 cells. The inocula were removed and cell monolayers washed three times with BA-1, and 2 ml of medium was added to each well. Plates were incubated for up to 6 days. The medium was sampled at 7.5, 16, 24, 32, 40, 48, and 72 hours for BHK-21 cells, as well as at 96 and 124 hours for C6/36 cells.

At an MOI of 5, one-step growth curves for both recombinant and parental viruses on BHK-21 and C6/36 cells were similar. Additionally, growth characteristics at a low MOI of 0.05 were also equivalent on both cell types. No quantitative or qualitative differences in CPE were observed between the viruses at each MOI.

This also indicated that phenotype, replication, and spread in both mammalian and insect cells were indistinguishable comparing parental to recombinant viruses.

Example 8

Figure 5:
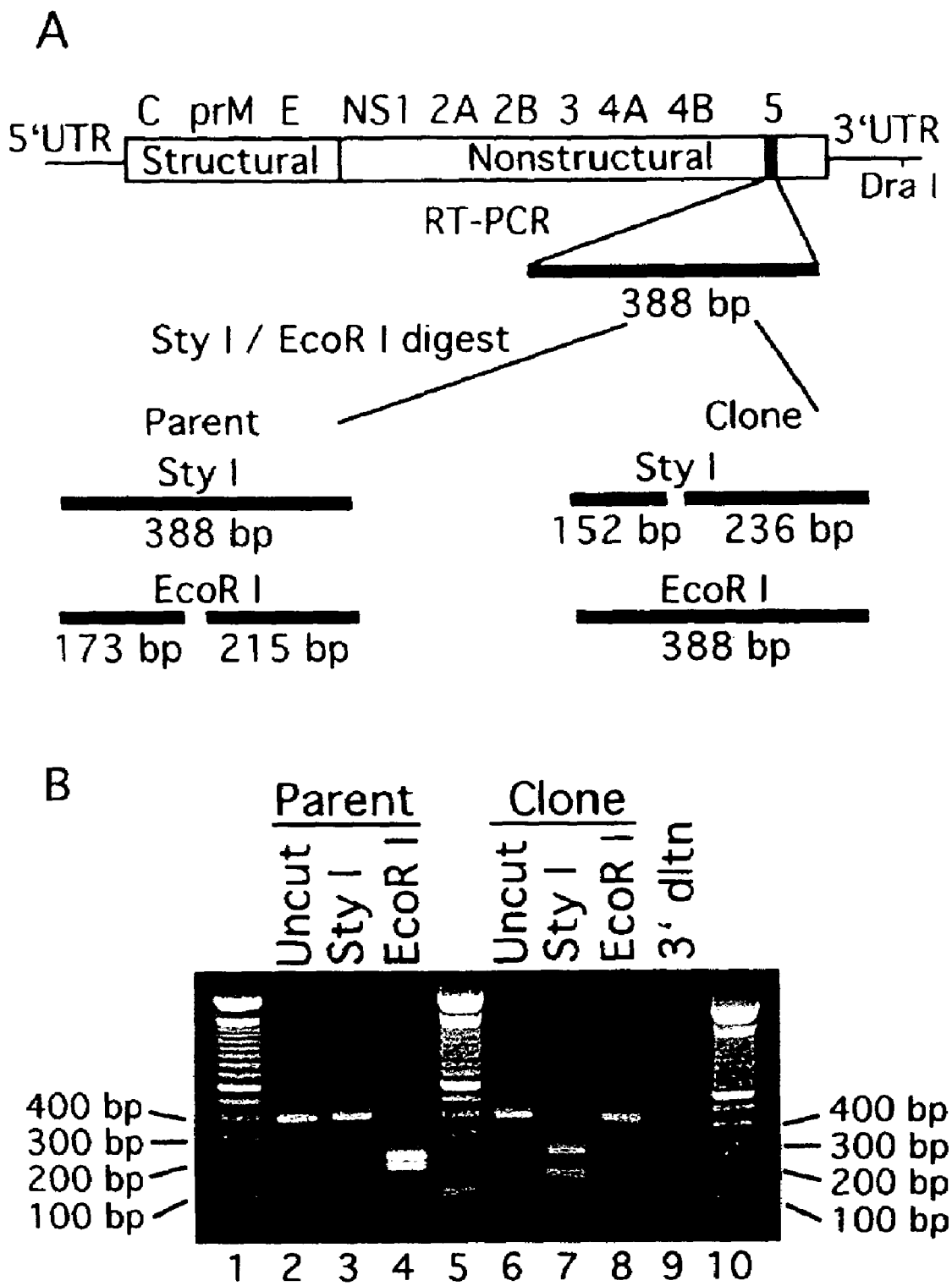
FIG. 5 shows how to distinguish between the full-length lineage I WNV cDNA clone and the parental virus. (A) shows that the 388-bp fragment derived from the full-length cDNA clone is cleaved by StyI but not by EcoRI, whereas a RT-PCR fragment amplified from parental viral RNA is cleaved by EcoRI but not by StyI. (B) shows the electrophoretic pattern of restriction fragments following StyI and EcoRI digestion of both the recombinant and the parental WNV. The pattern of restriction fragments shown in the gel (B) are consistent with the predicted sizes of restriction fragments in (A) thereby demonstrating that the recombinant virus isolated from the transfected cells is not parental virus contamination.

Authentication of Recombinant WNV by Molecular Analysis of Recovered Virus from Cells Infected with Recombinant cDNA RNA To determine if the recovered viral RNA from cells infected with recombinant cDNA RNA was not due to contaminating parental virus, the recovered RNA was tested by RT-PCR and restriction analysis (see FIG. 5). A StyI site was created and an EcoRI site was knocked out in the NS5 gene of the recombinant virus. A 388-bp fragment spanning nt 8706 to 9093 was amplified by RT-PCR from RNA extracted from either parental or recombinant virus. Digestion of the RT-PCR products with StyI and EcoRI showed different restriction fragment sizes, depending on the origin of the RNA. Consistently, RT-PCR products amplified from parental virus were cleaved with EcoRI to generate fragments of 173 and 215 bp, however StyI could not digest parental viral RT-PCR products. In contrast, products derived from the recombinant virus could not be cleaved by EcoRI, but could be digested by StyI, resulting in fragments of 152 and 236 bp in size. As a negative control, cells transfected with RNA containing a deletion of the 3'terminal 199 nt of the WNV genome did not yield any RT-PCR product. This indicates that virus recovered from cells transfected with the infectious full-length recombinant cDNA clone was not derived from contaminating parental virus.

Example 9

Comparison Of Parental and Recombinant WNV Virulence in Mice

The virulence of the recombinant WNV was compared to that of the parental WNV in mice (see Table 2 and FIG. 7). Female outbred CD-1 mice (Charles River Laboratories, Wilmington, Mass.) were housed in biosafety level 3, environmentally controlled rooms. The mice were obtained at 5 weeks of age and acclimatized for 1 week. Eight mice per group were inoculated with diluent alone (endotoxin-free PBS+1% BSA) or with $10^2$ PFU of parental or recombinant WNV subcutaneously in the left rear footpad. Mice were evaluated clinically and weighed daily for two weeks, then monitored daily and weighed thrice weekly for two more weeks. Observed clinical signs of infection included ruffled fur, paresis, hindleg paralysis, and tremors. Morbidity was defined as a greater than 10% weight loss or clinical signs for two or more days. Mice were euthanized if they became moribund. Exposure to virus was confirmed by ELISA on day 28 post-inoculation in mice that survived viral challenge. The morbidity, mortality, and average survival times are included in Table 2:

TABLE 2

Morbidity and mortality of parental and recombinant WNV in adult mice

| Inoculum | Morbidity (# of sick/total) | Mortality (# of dead/total) | Avg. survival time (days [SD]) |
|---|---|---|---|
| Diluent | 0/8 | 0/8 | NA |
| Parental WNV | 7/8 | 5/8 | 9.4 [1.96] |
| Recombinant WNV | 5/8 | 4/8 | 10.2 [2.50] |

There were no observable differences in the severity or quality of the clinical signs, and furthermore, there were no statistical differences in the morbidity, mortality, or average survival times. Thus, the virulence between parental and recombinant viruses was indistinguishable.

Example 10

Construction of Replicons of Lineage I West Nile Virus

Figure 8:
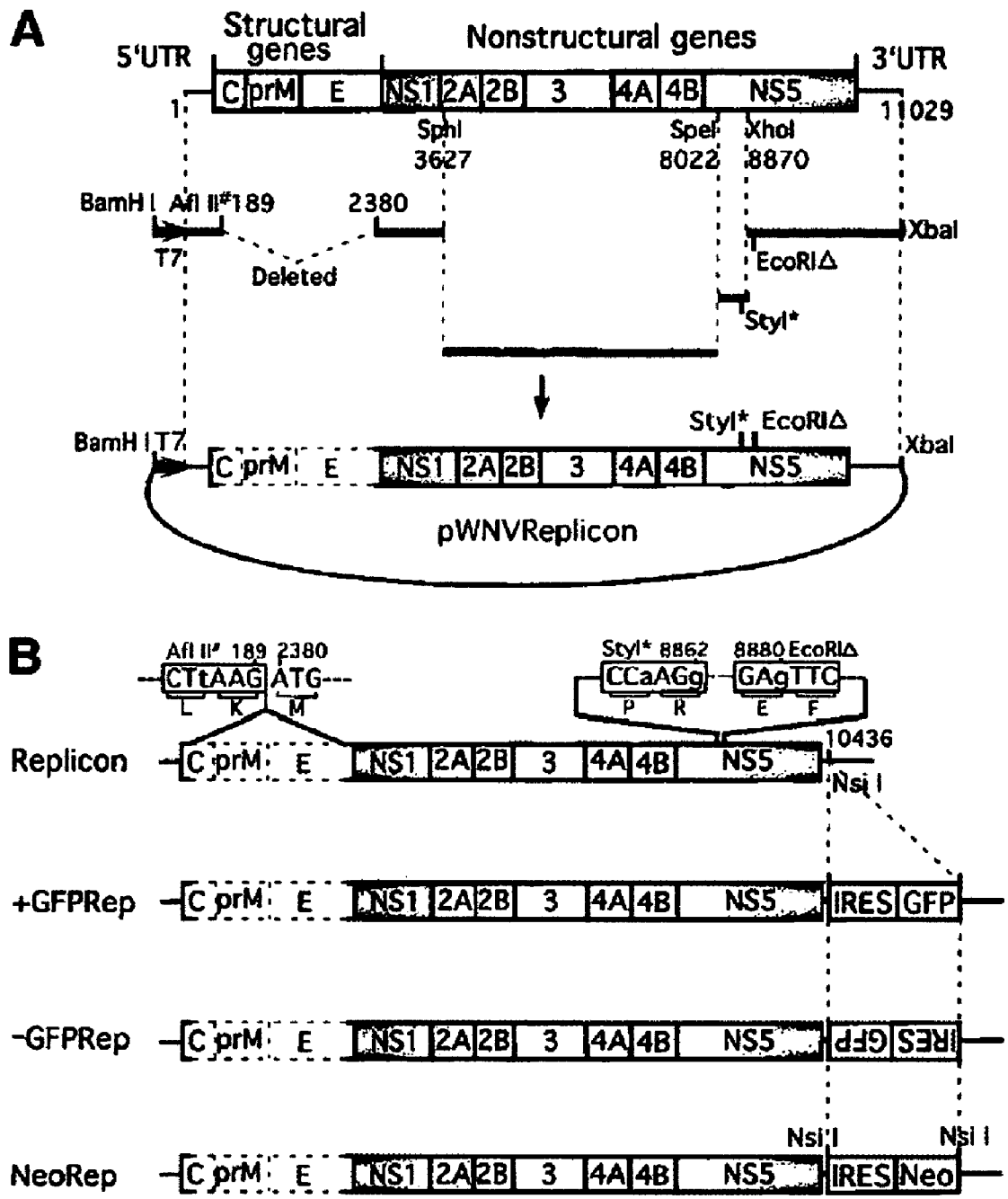
FIG. 8 depicts the strategy of WNV replicon construction and schematic drawings of the constructed replicons. The WNV genome is shown in (A) along with restriction sites used for cloning. The numbers referring to nucleotide positions are based on the sequence of WNV strain 3356 (Accession No. AF404756; SEQ ID NO.1). The dotted lines and dotted open boxes refer to an in-frame deletion in the structural region of C-prM-E. All replicons depicted in (B) contain the identical in-frame deletion of the structural region. Recombinant replicons contain silent nucleotide changes to generate a StyI site and to eliminate an EcoRI site. The GFP and Neo reporter gene fragments, along with an upstream IRES ("internal ribosome entry site") regulatory sequence, were engineered into the 3' untranslated region of WNV at the NsiI site.

Replicons containing cDNA sequences corresponding to the WNV genome were cloned into the pBRLinker plasmid essentially as described in Example 1, but with some modifications (see FIG. 8). The T7 promoter sequence was added to the plasmid by amplification of the WNV 5' untranslated region (UTR) fragment using primer 1V and primer 197C (see Table 3 for sequences).

TABLE 3

Primers Used in Construction of WNV Replicons

| Primer | Primer Sequence | Amplified Fragments |
|---|---|---|
| 1V | CAAA*GGATCC*TAATACGACTCACTATAGAGTAGTTCGCCTGTGTGAGCTGA<br>(*Bam*HI underlined, T7 promoter italicized)<br>(SEQ ID NO.11) | *Bam*HI - *Afl*II |
| 197C | TAGCCCT<u>CTTaAG</u>TCCAATCAAG<br>(*Afl*II underlined)<br>(SEQ ID NO.12) | *Bam*HI - *Afl*II |
| 2380V | TtccttctCTtAAGATGGGCATCAATGCTCGTGAT<br>(*Afl*II underlined)<br>(SEQ ID NO.13) | *Afl*II - *Sph*I |
| 3839C | ATGTTCTCCTGGTTGGTCCA<br>(SEQ ID NO.14) | *Afl*II - *Sph*I |
| 3286V | GTAGAGATTGACTTCGATTAC<br>(SEQ ID NO.15) | *Sph*I - *Spe*I |
| 8804C | CGTACTTCACTCCTTCTGGC<br>(SEQ ID NO.16) | *Sph*I - *Spe*I |
| 8016V | GCCCCAACTAGTGCAAAGTTATGGATGGAAC<br>(SEQ ID NO.17) | *Spe*I - *Xho*I |
| 8881C | ATTCTT*CTCGAG*AGCACAT<u>CCTTGG</u>ACGTTTTTCTCTGGCC<br>(*Xho*I italicized, *Sty*I underlined)<br>(SEQ ID NO.18) | *Spe*I - *Xho*I |
| 8865V | GTGCT*CTCGAG*AG<u>GAGTTC</u>ATAAGA<br>(*Xho*I italicized, *Eco*RIΔ underlined)<br>(SEQ ID NO.19) | *Xho*I - *Xba*I |
| 11029C | AACAA<u>TCTAGA</u>GATCCTGTGTTCTCGCACCAC<br>(*Xba*I underlined)<br>(SEQ ID NO.20) | *Xho*I - *Xba*I |
| FIRES | ATAATT<u>ATGCAT</u>CCGCCCCTCTCCCTC<br>(*Nsi*I underlined)<br>(SEQ ID NO.21) | IRES-GFP |
| RGFP | CCAGCC<u>ATGCAT</u>TACTTGTACAGCTCGTCCCA<br>(*Nsi*I underlined)<br>(SEQ ID NO.22) | IRES-GFP |
| RIRES | *GCAATCCATCTTGTTCAATCATGGTATTATCATCGTGTTTTTCAAAGG*<br>(SEQ ID NO.23) | IRES (italicized sequence) |
| FNeo | CCTTTGAAAAACACGATGATAATACC*ATGATTGAACAAGATGGATTGC*<br>(SEQ ID NO.24) | Neo (italicized sequence) |
| RNeo | ACAACC<u>ATGCAT</u>CAGAAGAACTCGTCAAGAAG<br>(*Nsi*I underlined)<br>(SEQ ID NO.25) | Neo (italicized sequence) |
| FLuc | TACACT<u>CTTAAG</u>ATGGCTTCCAAGGTGTACGA<br>(*Afl*II)<br>(SEQ ID NO.26) | |
| RLuc | CACAAG<u>CTTAAG</u>CTGCTCGTTCTTCAGCACG<br>(*Afl*II)<br>(SEQ ID NO.27) | |

The native WNV 5' UTR was retained because it contains a cis-acting cyclization sequence necessary for proper replication of the viral genome. Primer 1V contains the T7 promoter sequence following a BamHI restriction site. Primer 197C generated a G→T silent mutation at nt 186 to engineer a new AflII site. A second fragment from AflII to SphI was generated using primers 2380V. This primer set amplified a fragment containing an AflII site directly fused with nt 2380, resulting in a deletion of the structural coding region from nt 190 to 2379. Nucleotides 2380-2469, corresponding to the C-terminal coding sequence of the E protein within the structural domain, was retained to preserve correct processing and translocation of the NS1 gene product and the remaining nonstructural polyprotein in the correct topology across the membrane of the endoplasmic reticulum. The digested fragments of BamHI to AflII and AflII to SphI were directly cloned into plasmid pSph-Xba at the corresponding restriction sites by three-way ligation. The resulting plasmid, named pWNVReplicon, contained the T7 promoter followed by the WNV sequence with a deletion from nt 190 to 2379. This deleted portion corresponds to greater than 92% of the C-prM-E structural region of the genome.

Standard cloning procedures were performed and products amplified in *E. coli* strain HB101 at room temperature. Plasmids were electroporated into cells in 0.2 cm cuvettes using a GenePulser apparatus with settings of 2.5 kV, 25 µF, and 200Ω. Sequences of all intermediate products of cloning were verified by sequence analysis using automated DNA sequencing. PCR amplification was achieved using Deep Vent polymerase (New England Biolabs, Beverly, Mass.). RNA transcription and transfection was performed essentially as described in Example 1. Intact replicon RNA was verified by formaldehyde gel electrophoresis and compared to full-length WNV genomic transcripts (see FIG. 9).

Example 11

Construction of Lineage I West Nile Virus GFP Reporter Replicons

GFP-expressing lineage I WNV replicons were constructed by inserting a nucleotide sequence encoding the green fluorescent protein reporter preceded by an internal ribosomal entry site (IRES) into the upstream end of the 3' untranslated region of the original lineage I WNV replicon of Example 10. The IRES-GFP DNA fragment was amplified from plasmid pIRES2-EGFP (Clontech, Palo Alto, Calif.) using primers FIRES and RGFP (see Table 3 for primer sequences). This fragment contained an NsiI site at nt 10,436 of the 3' untranslated region of the original replicon. Clones with insertions of either plus-sense (+GFPRep) or minus-sense IRES-GFP (−GFPRep) were selected. RNA transcription and transfection was performed essentially as described in Example 3. Intact replicon RNA was verified by formaldehyde gel electrophoresis and compared to full-length WNV genomic transcripts (see FIG. 9). In place of the GFP-encoding nucleotide sequence, a nucleotide sequence encoding luciferase (firefly) was inserted at the 3' end of the WNV replicon vis-à-vis the same strategy as the GFP-encoding nucleotide sequence. Both the GFP and luciferase-based lineage I WNV replicons were shown to maintain stable expression levels of the GFP and luciferase reporters (data not shown).

Example 12

Construction of Lineage I West Nile Virus Neomycin Reporter Replicons

Preparation of fragments containing IRES-Neo was achieved by individually amplifying PCR products of IRES and the neomycin resistance gene by primer pairs FIRES and RIRES, and FNeo and RNeo, respectively (see Table 3 for primer sequences). Overlapping sequences were designed at the junction of the IRES and Neo sequences. Fragments of IRES and Neo were ligated to yield IRES-Neo through overlapping PCR. The fused IRES-Neo was subcloned into the NsiI restriction site of the 3'UTR of the original replicon to yield a plus-sense IRES-Neo replicon. RNA transcription and transfection was performed essentially as described in Example 3. Intact replicon RNA was verified by formaldehyde gel electrophoresis and compared to full-length WNV genomic transcripts (see FIG. 9).

Example 13

Figure 10:
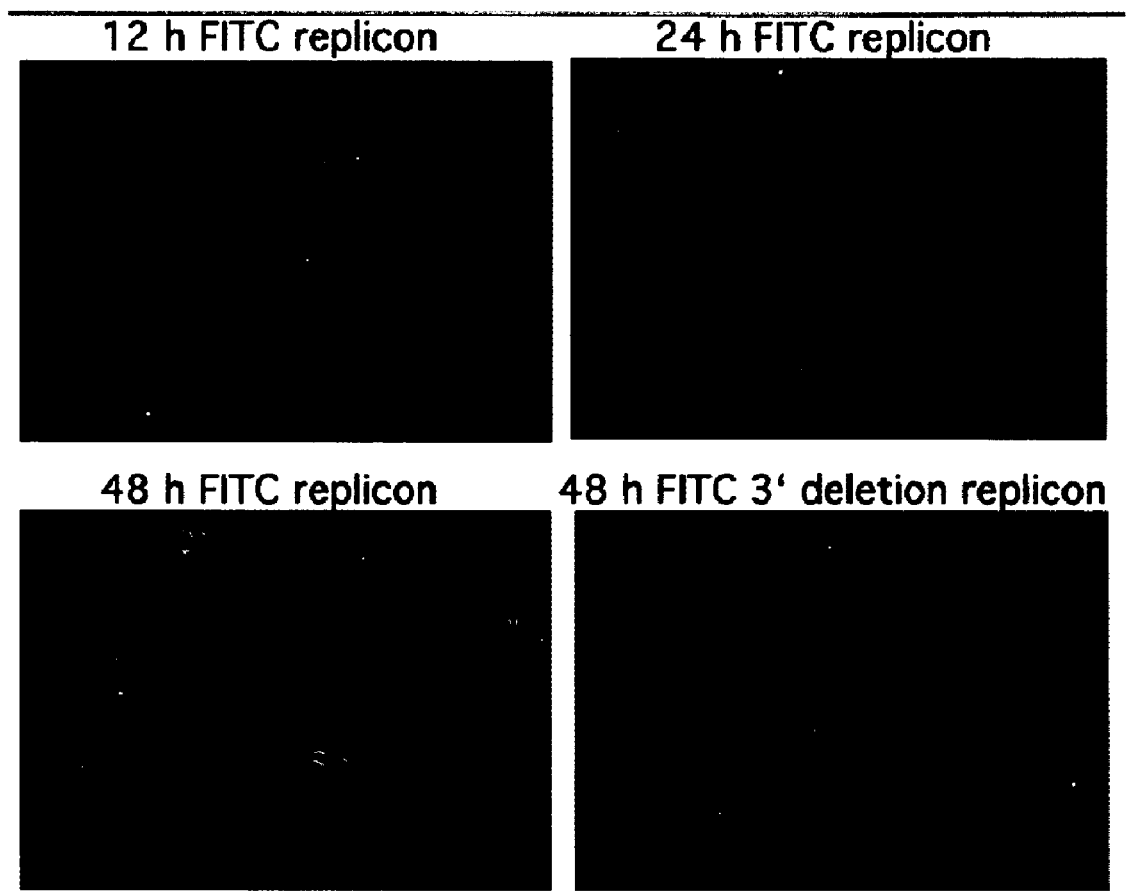
FIG. 10 depicts indirect immunofluorescence analyses of BHK-21 cells transfected with replicon RNA at various time points post-transfection. WNV immune mouse ascites fluid and FITC-conjugated goat anti-mouse antibodies were used as primary and secondary antibodies, respectively. Cells transfected with a replicon containing a terminal 597-nt deletion of the 3' UTR were used as a negative control.

Characterization of Replicons of Lineage I West Nile Virus by Indirect Immunofluorescence Analyses Replicon RNA was transfected into BHK-21 cells by electroporation. RNA replication was monitored by indirect immunofluorescence using anti-WNV mouse ascites fluid and goat anti-mouse FITC-conjugated or Texas Red-conjugated secondary antibodies, essentially as described in Example 4 (see FIG. 10). During a time-course of infection, no IFA signals were detected 12 h post-transfection. Staining was apparent at 24 h and signals increased at 48 h post-transfection. No cytopathic effects were observed in IFA-positive cells, indicating that viral genome replication occurred independently of infectious virion production. As a negative control, the same replicon plasmid containing a deletion of the 3'UTR was transfected into cells. This replicon failed to replicate, as shown by the absence of positive IFA signals, indicating that the positive IFA signals seen in cells resulted from the replication of the transfected replicon, rather than from translation of the unamplified input RNA.

Example 14

Characterization of Lineage I WNV Replicons by Analysis of Replicon RNA Synthesis Extracted RNA was quantitated by spectrophotometry and used in real-time RT-PCR reactions to quantitate replicon RNAs (ABI Prism 7700 Sequence Detector with Taq-Man One-Step RT-PCR; Applied Biosystems). Transfected BHK-21 cells were harvested by trypsinization at various time points post-transfection. Total RNA was extracted using RNeasy kits (Qiagen). Primers 3111V (5'-3') and 3239C (5'-3') were targeted to amplify nt position 3111 to 3239 in the NS1 gene and distinguish between minus and plus-sense RNAs. The 50 µl reactions contained 2.5 µg of extracted RNA, 1 µM concentration of primer, 0.2 µM probe, and One-Step RT-PCR master mix. The reactions were subjected to 48° C. for 30 minutes at room temperature, followed by 95° C. for 10 minutes to heat-inactivate reverse transcriptase and activate Taq polymerase. Following this, a second primer was then added to the reactions, and the tubes subjected to PCR amplification through 40 cycles of 95° C. for 15 seconds and 60° C. for 1 minute. RNA was quantitated within the linear range of the assay and by reference to RNA extracted from a viral stock with a known titer expressed in plaque forming units (PFU). Standard titers used were 800, 80, 8, 0.8, and 0.08 PFU.

Figure 11:
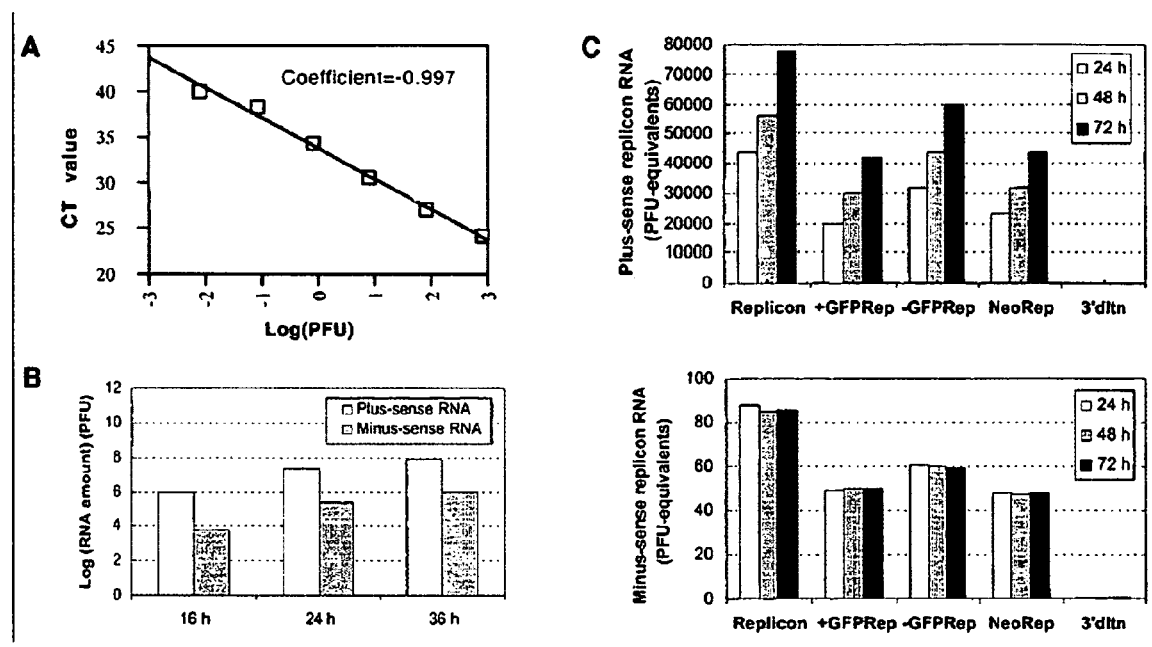
FIG. 11 shows 5' nuclease RT-PCR analysis of WNV RNA. A standard curve of real-time RT-PCR was generated to demonstrate replicon RNA quantitation in transfected cells. Threshold cycles ($C_T$) were graphed versus the log of the titrated amount of virus (PFU) (A). (B) shows the quantitation of viral RNA during WNV infection. BHK-21 cells were infected with WNV at an MOI ("multiplicity of infection") of 1 and harvested at the indicated time points post-infection. Extracted RNAs were quantitated by real-time RT-PCR based on polarity of the viral RNA transcripts. The replicon RNAs were quantitated based on polarity in (C). BHK-21 cells were transfected with replicon RNAs and harvested at the indicated time points. One representative experiment of two is shown.

One set of primers and probe targeted a region of the WNV NS1 gene between nt 3111 to 3239, and was used to selectively quantitate either minus- or plus-sense replicon RNA. The reverse transcription step was performed asymmetrically using either a sense or an antisense primer to distinguish the polarity of the replicon reporter-encoding nucleotide sequence. The second primer was added after the reverse transcription step to allow real-time PCR amplification. The assay was first validated to quantitate RNA synthesis during a normal WNV infection (see FIG. 11). BHK-21 cells were infected with parental WNV at MOI=1. Cells were harvested at 16, 24, and 36 h post-infection and the resultant RNA extracted. Both plus and minus-sense viral RNA increased by approximately 2 logs of PFU from 16 h to 36 h post-infection. The ratio of plus-sense to minus-sense RNA was approximately 100:1. This is consistent with comparisons of plus- and minus-sense RNA quantitation by ribonuclease protection assay (Muylaert et al, (1996) Virology 222: 159-168).

Real-time RT-PCR was then applied to estimate replicon RNA synthesis. RNA was extracted from cells at 24, 48, and 72 h post-transfection. From 24 h to 72 h, plus-sense RNA was detected from $4.4 \times 10^4$ PFU to $7.8 \times 10^4$ PFU. The amount of minus-sense RNA was measured from approximately 85-88 PFU. Transfection of cells with a negative control replicon harboring a deletion of the 3'UTR did not produce significant, detectable levels of either plus- or minus-sense RNA. This indicates that replicon RNA replicated efficiently in transfected cells and plus-sense RNA is synthesized preferentially to minus-sense RNA.

To determine if the transfected cells expressed parental or replicon WNV, restriction analysis was performed using StyI and EcoRI (see FIG. 12). As detailed above, StyI was engineered into the recombinant sequence, while the native EcoRI site from the parental sequence was destroyed. Consistently, StyI was capable of cleaving sequences, while EcoRI failed, indicating that the template for RNA replication was the replicon and not contaminating parental virus.

Example 15

Analysis of Replicon RNA Containing a Nucleotide Sequence Encoding a GFP Reporter Nucleotide sequences encoding GFP and neomycin reporters were engineered into the WNV replicon to facilitate easy detection of replication of the WNV replicons and to determine if exogenous reporter genes were capable of being expressed via the replicon system. An IRES was inserted upstream of the reporter-encoding nucleotide sequences to facilitate cap-independent bicistronic expression of the reporters. GFP expression from the plus-sense +GFPRep was detected from 60 h to 86 h post-transfection. This is in contrast to cells subjected to IFA analysis, where signals were detected from 36 h to 80 h post-transfection (FIG. 13). Co-localization experiments were performed in cells transfected 86 h prior to harvesting. The results show that identical cells expressed GFP and viral proteins. Replicons with IRES-GFP inserted in the opposite, minus-sense orientation, denoted as −GFPRep, were transfected into cells. However, even in cells at the 86 h post-transfection time point, no GFP-expressing cells were detected (FIG. 14). Longer incubation did not yield GFP-positive cells, indicating that GFP expression was not achieved from −GFPRep. Viral proteins, however, were synthesized, as an increasing IFA signal from 36 to 60 h post-transfection of −GFPRep was detected.

RNA replication in cells transfected with +GFPRep was analyzed by real-time RT-PCR. The amount of plus-sense RNA increased from $\sim 2 \times 10^4$ PFU to $4.2 \times 10^4$ PFU from 24 to 72 h post-transfection. Minus-sense RNA remained at around 50 PFU during the same time period. This indicates that plus-sense RNA is transcribed preferentially over minus-sense and replication was efficient enough to drive detectable expression of GFP. When examining −GFPRep by real-time PCR, approximately $3.2 \times 10^4$ PFU, $4.4 \times 10^4$ PFU, and $6 \times 10^4$ PFU of plus-sense RNAs were detected at 24, 48, and 72 h post-transfection, respectively. The amount of minus-sense RNA from −GFPRep remained at 60 PFU during the same time period. The −GFPRep construct was sequenced to ensure that the absence of GFP expression was not due to mutations in IRES-GFP generated during the cloning procedure. Thus, while efficient replication of −GFPRep does occur in transfected cells, no GFP expression was detected.

Example 16

Generation of Cells Stably Expressing WNV Replicons Containing Neomycin Resistance Gene BHK-21 cells were transfected with 20 µg of Neo replicon RNA to generate a cell line that stably and persistently expresses WNV replicons. Approximately $5 \times 10^4$ cells were plated in 60-mm dishes and allowed to recover for 4-6 h before addition of 1 mg/ml G418 (geneticin, Gibco BRL) in Dulbecco's modified Eagle's medium (DMEM) supplemented with 10% FBS. Medium was replaced every 2-3 days with fresh G418. Individual foci were cloned, expanded, and stored frozen in 10% dimethyl sulfoxide (DMSO) and 40% FBS in liquid nitrogen. Expression of the Neo replicon allowed for selection of cells containing persistently replicating RNA. IFA analysis of cells at 36 h post-transfection revealed that in the absence of G418 selection, less than 10% of cells stained positive for viral proteins (see FIG. 15). A time-course analysis of real-time RT-PCR demonstrated that NeoRep RNA was synthesized to levels similar to that of +GFPRep. At later times, G418-selected cells from passage 2 (15 days after initial selection by G418) expressed high levels of viral proteins as determined by IFA analysis. After 40 days of selection, each individual cell remained IFA positive and without apparent morphological changes or cytopathic effects, indicating that cells that persistently replicate NeoRep efficiently express viral proteins without apparent detrimental effects.

Example 17

Construction of Full-Length Infectious cDNA Clones Containing Nucleotide Sequences Encoding a GFP Reporter Example 1 describes the construction of full-length infectious cDNA clones of WNV Lineage I. Also, Example 11 describes the insertion of reporter-encoding nucleotide sequences GFP and luciferase into lineage I WNV replicons whose expression is regulated by an upstream IRES sequence. Likewise and in a similar manner, GFP was incorporated into the fully-infectious lineage I WNV cDNA clone of the invention. The pFLWNV plasmid, which is described above, which carries the full-length lineage I WNV cDNA clone, was be used as a starting point in construction. pFLWNV contains a NsiI restriction site in its 3'UTR. A DNA fragment carrying a nucleotide sequence encoding IRES-GFP was amplified from plasmid pIRES2-EGFP (Clontech, Palo Alto, Calif.) using primers FIRES and RGFP (see Table 3 for primer sequences) and inserted into the NsiI site of pFLWNV. Clones with insertions of either plus-sense or minus-sense IRES-GFP were selected. RNA transcription and transfection was performed essentially as described in Example 3. Intact RNA was verified by formaldehyde gel electrophoresis and compared to full-length WNV genomic transcripts (data not shown). In place of the GFP-encoding nucleotide sequence, a nucleotide sequence encoding luciferase (firefly) was inserted at the 3' end of the WNV replicon vis-à-vis the same strategy as the GFP-encoding nucleotide sequence. Both the GFP and luciferase-based lineage I WNV fully-infectious cDNA clones were shown to maintain stable expression levels of the GFP and luciferase reporters (data not shown).

Example 18

Construction of Dual Reporter Replicon Systems

Similar to what is described in Examples 12 and 16, a variant replicon, engineered with nucleotide sequences encoding a Neo selectable marker and a GFP reporter, will be transfected into cells, and the cells cultured in the presence of neomycin. The Neo and GFP genes will be linked by the autoprotease sequence, 2A, from the Foot and Mouth Disease virus, allowing the two proteins to be disjoined following co-translation from the single IRES sequence upstream of the genes. The reporter sequences, along with the IRES sequence, will be flanked by NsiI sites at the 5' end of the IRES the 3' end of GFP sequence, allowing for insertion of the entire IRES-Neo-GFP fragment into the NsiI site located at nt 10436. Cells will be cultured in the presence of G418 as described in Example 16 and GFP fluorescence will be monitored by fluorescence microscopy using FITC optics. The stability and persistence of the GFP signal will be tested in cells that have been passaged continuously in the presence of G418. Similarly, luciferase can be substituted for GFP, resulting in a replicon containing IRES-Neo-Luc.

Example 19

High-Throughput Assays for Screening Inhibitors Using Full-Length Infectious Clones and Single or Dual Reporter Replicon Systems A cell-based assay to screen large numbers of potential antiviral compounds will also be developed. This assay can use any of the following constructs described above: 1) full length infectious cDNA clone containing a nucleotide sequence encoding a reporter (see Example 17), 2) a replicon system comprising a single reporter-encoding nucleotide sequence as described in Examples 11 and 12, and 3) a replicon system comprising two reporter-encoding nucleotide sequences adescribed in Example 18. The assay will utilize BHK-21 cells that express the plasmids, and identical yet separate cell populations will be contacted with a different potential antiviral compound. The assay will screen for compounds that result in a reduction in the reporter signal from the WNV reverse genetics systems. For GFP-expressing cells, any reduction in the fluorescent signal can be monitored by fluorescence activated cell sorting (FACS; or flow cytometry). Alternatively, fluorescent signals can be detected by fluorescent plate assay, performed in micro- and nanotiter plates. Still further, fluorescence detection instrumentation known in the art can be used, including automated "fluorescence readers" and software. For cells expressing only the neomycin resistance gene, reduction in expression of this gene will be determined by enzyme-linked immunosorbent assay (ELISA), using antibodies specific to the neomycin resistance gene product. Using the replicon systems will not screen for inhibitors that are directed against viral packaging and virion assembly, as the replicons contain deletions of the structural regions of WNV genome. When screening for inhibitors specific for the structural regions, the full-length infectious cDNA clone containing one or more reporter-encoding nucleotide sequences will be used. For high throughput screening, a plurality of potential inhibitors can be screened in parallel by utilizing known technologies in the art, such as multi-wells microplates. In the case of microplates, a reader can be used to acquire the fluorescence signals generated by the assay. Data can be storeed to databases in accordance with the invention and manipulated, analyzed, accessed, transferred, and visualized by using a computing device known in the art, such as, for example a personal computer or network station. The high throughput methods further contemplate using any suitable bioinformatics method, software, or instrumentation known to one of ordinary skill in the art to facilitate in data analysis, i.e., "making sense of the data."

A variant of the replicon system can also be used, termed "suicide infection". In this method, the replicons will be co-transfected into BHK-21 cells along with plasmids containing structural regions of the genome that were deleted in the replicon. In this manner, the genes responsible for virion assembly are supplied in trans, allowing for assembly of infectious viral particles. However, because the replicons themselves are responsible only for viral genome replication and do not contain the structural genes, infection is limited to one replication cycle. Potential antiviral activities of compounds can be monitored by reduction of the reporter signal expressed during replication of replicon RNA.

Potential antiviral candidates obtained from the above genetic cell-based assays will be further analyzed by enzymatic assays using purified recombinant proteins encoded by WNV. The cell-based genetic assays described above allow more than one protein activity to be targeted, and a biochemical assay would allow the specific target to be identified. Two proteins in particular, the NS3 and NS5 genes, encode for proteins that have been targets for other antiviral compounds for other viruses. NS3 exhibits protease, helicase, and NTPase activities, while NS5 encodes RNA-dependent RNA polymerase activity. The biochemical assay will use the scintillation proximity assay (SPA), which is a radioisotopic homogeneous assay technology that is widely accepted as a tool for evaluation of large volumes of compounds. This technique relies upon the observation that energy emitted from a radioisotope will only travel a limited distance in an aqueous environment. A potential antiviral compound, labeled with a radioisotope, will bind to a fluorescently tagged microsphere bound to an antibody against the protein of interest (e.g. NS3, NS5). This antibody-microsphere complex will specifically bind the NS3 or NS5 protein. The fluorescent tag is unique in that they fluoresce only when excited by radioactive energy, such as $^3$H β particles and $^{125}$I Auger electrons. Thus, when the radiolabeled compound is bound to the microsphere-protein complex, this allows the radiation energy emitted to activate the fluorescent compound and emit light detectable by a scintillation counter. In this manner, novel antiviral compounds can be identified in the genetic assays and their direct targets verified by SPA.

Example 20

Production of Attenuated Virus by Deletion of 3' Untranslated Region of WNV

The 3'UTR of WNV contains regulatory sequences that are necessary for proper replication of the virus. It is these sequences, particularly the conserved regions, which have been shown in other flaviviruses such as TBEV, to be key in development of live, attenuated virus for vaccine production (Mandl et al, (1998) *J. Virol.* 72(3): 2132-2140). The single replicon system described in Example 11 was modified to contain a nucleotide sequence encoding a luciferase reporter in place of GFP, with an upstream IRES sequence. In addition, targeted deletions of sequences in the 3'UTR, specifically the conserved sequence element 2 (CS2) region spanning nt 10875 to 10896 and the repeated conserved sequence element 2 (RCS2) region, which spans nt 10801 to 10822, were generated in the same replicon. These RNAs were in vitro transcribed and transfected into cells essentially as described in Example 3. Replication of replicon RNA was measured by luciferase activity on a luminometer (LB9501-1, Perkin-Elmer, Boston, Mass.).

Luciferase activity was decreased to 8-18% of wild-type activity in the 3'UTR mutants, indicating that while viral replication was not abolished, it was severely reduced.

Each of the references cited in the present Example are incorporated herein by reference in their entirety.

Example 21

Engineering of a Lineage I WNV Replicon with Both *Renilla* Luciferase (Rluc) and Neomycin Phosphotransferase (Neo)

To develop a high-throughput antiviral assay for the screening and identification of potential flavivirus inhibitors, especially inhibitors of WNV, nucleotide sequences encoding two reporter, namely, *Renilla* luciferase (Rluc) and neomycin phosphotransferase (Neo), were engineered into the WNV replicon of Example 10, resulting in WNV Rluc/NeoRep (FIG. 18). Translation of the Neo gene was driven by an EMCV internal ribosomal entry site (IRES) in the upstream end of the 3' UTR of the replicon. To prepare the IRES-Neo fragment, individual IRES and Neo were amplified through PCR from plasmid pIRES2-GFP (Clontech, Palo Alto, Calif.) and pcDNA3.1 (Invitrogen, Carlsbad, Calif.), using primer F-IRES (SEQ ID NO. 21; Table 3) and R-IRES (SEQ ID NO. 23; Table 3), and F-Neo (SEQ ID NO. 24; Table 3) and R-Neo (SEQ ID NO. 25; Table 3), respectively. Fragments of IRES and Neo were then fused to yield IRES-Neo through overlapping PCR (Monath, T. 2001. Ann. N.Y. Acad. Sci. 951:1-12). The fused IRES-Neo was inserted into the NsiI site (nt 10436) in the 3' UTR of the original replicon. Next, the Rluc gene was PCR-amplified from plasmid pRL-SV40 (Promega, Madison, Wis.) using primer F-Rluc (SEQ ID NO.26; Table 3) and R-Rluc (SEQ ID NO.27; Table 3), and then fused in-frame into the AflII site of the replicon (Shi, P. Y., et al. 2002. Virology 296: 219-233; Lo, M. K., et al. 2003. J. Virology 77, 12901-12906.) Rluc gene was selected as a reporter for assay development because of its relatively small size (936 bp) and its robust enzymatic activity. Each of the references cited in the present Example are incorporated herein by reference in their entirety.

Example 22

Testing the Competency of Replication of the Engineered Lineage I WNV Replicon of Example 21

To test whether the dual reporting replicon of Example 21 is replication competent, Rluc/NeoRep RNA was in vitro transcribed and transfected into BHK-21 cells as previously described (Shi, P. Y., et al. 2002. Virology 296:219-233; Shi, P. Y., et al. 2002. J. Virol. 76:5847-56; Lo, M. K., et al. 2003. J. Virology 77, 12901-12906). BHK-21 cells at 48 h post-transfection (p.t.) expressed both viral and reporter Rluc proteins, as evidenced by the positive cells from the immunofluorescence assay (IFA; top panel in FIG. 18B). Less than 10% of the cells were IFA-positive, principally due to low transfection efficiency. Although the Rluc protein contained fusion tags at its N and C termini derived from the viral C protein and E protein, respectively (Rluc/NeoRep in FIG. 18A), a high level of Rluc activity was detected from cell lysates harvested at 48 h p.t. (a filled far in FIG. 18C). By contrast, transfection of BHK-21 cells with an equal amount of a mutant replicon, containing a frameshift insertion of a nucleotide U between nt 8027 and 8028 to knock out the active site of the NS5 RdRp gene (Rluc/NeoRepNS5mt in FIG. 18A), yielded no signals in either IFA (data not shown) or Rluc assay at 48 h p.t. or longer (a hollow bar in FIG. 18C). These results suggested that the positive IFA and Rluc activity from the cells at 48 h after transfection with the Rluc/NeoRep were due to translation of replicating viral RNA, not the translation of the input replicon RNA. Each of the references cited in the present Example are incorporated herein by reference in their entirety.

Example 23

Establishing a Cell Line Containing the Engineered Lineage I WNV Replicon of Example 21

To establish a stable cell line containing persistently replicating dual reporting replicon, we transfected BHK-21 cells with the Rluc/NeoRep and selected the transfected cells under geneticin (G418). Briefly, approximately $8 \times 10^6$ BHK-21 cells were electroporated with 10 micrograms of Rluc/NeoRep RNA at settings previously described (Shi, P. Y., et al. 2002. J. Virol. 76:5847-56; Lo, M. K., et al. 2003. J. Virology 77, 12901-12906), recovered in cuvettes for 10 min, resuspended in 50 ml DMEM medium containing 10% FBS, and transferred to a T-150 flask. After an overnight recovery, the cells were subjected to G418 selection (1 mg/ml) in DMEM with 10% FBS. Medium was replaced every 2 to 3 days with fresh G418. After 10 days of selection, the majority of the cells died, presumably because these cells were untransfected, or because they expressed an insufficient amount of Neo. However, many surviving cells were observed. Individual foci were cloned, expanded, and stored in 10% dimethyl sulfoxide (DMSO) and 40% FBS in liquid nitrogen. Cells were continually passaged under G418 selection for over 80 days (over 25 passages).

To test the stability of the replicon-containing cell lines, cells at various time points post-selection (p.s.) were examined for viral and Rluc protein expression, and for replicon RNA copy numbers. (i) IFA showed that all cells expressed viral and Rluc proteins on days 20 and 80 p.s. (lower two panels in FIG. 18B). Western blotting of the cell lysates harvested on day 80 p.s. also showed expression of viral and Rluc proteins of the expected molecular masses (data not shown). (ii) Stable and high levels of Rluc activity were detected from cells collected on days 20, 50, and 80 p.s. (FIG. 18C). For Rluc assay, $10^6$ cells were lysed in 500 microliters of lysis buffer; 20 microliters of lysate was measured for Rluc activity according to the manufacturer (Promega) using a Lumat luminometer (EG & G, Berthold, Australia). Approximately $8 \times 10^6$ light units were consistently detected from $4 \times 10^4$ cells, about 200 light units per cell. (iii) A consistent level of replicon RNA was maintained in cells at 20, 50, and 80 days p.s. (FIG. 18D). Real-time RT-PCR, targeting the viral NS1 region, was used to quantify replicon RNA as previously reported (Shi, P. Y., et al. 2002. Virology 296:219-233; Shi, P. Y., et al. 2002. J. Virol. 76:5847-56; Lo, M. K., et al. 2003. J. Virology 77, 12901-12906). Total RNA extracted from $10^6$ cells was eluted in 50 microliters of RNase-free water using RNeasy kits (Qiagen); 5 microliters of RNA was quantified by real-time RT-PCR, using in vitro trancribed RNA as standards. About $10^9$ replicon molecules in $10^5$ cells was estimated, or about $10^4$ replicon RNAs per cell.

These results demonstrated that the reporting cell line is stable, and contains persistently replicating Rluc/NeoRep.

Each of the references cited in the present Example are incorporated herein by reference in their entirety.

Example 24

Examining Whether the Cell Line of Example 23 Could be Used as an Antiviral Assay To examine whether the reporting cell line can be used as an antiviral assay, three known WNV inhibitors were tested in the cells: 6-azauridine, an inhibitor of orotidine monophosphate decarboxylase, and mycophenolic acid and ribavirin, inhibitors of inosine monophosphate dehydrogenase (De Clercq, E. 1993. Advance Virus Res. 42:1-55; Jordan, I., et al. 2000. J. Infect. Dis. 182:1214-7; Morrey, J., et al. 2002. Antiviral Res. 55:107-116). Ribavirin has also been reported to function as a mutagen, causing lethal levels of mutagenesis within the virus population (Crotty, S., et al. 2000. Nature Med. 6:1375-9). All three compounds were purchased from Sigma (St. Louis, Mo.). Initially, the assay was performed in 12-well plates. Approximately $2.5\times10^5$ cells were seeded into each well, containing DMEM medium with 2.5% FBS (without G418). Compounds were dissolved in DMSO, and added to cells at various concentrations in medium with a final DMSO concentration of 1%. After 24 h of compound treatment at 37° C., cells were assayed for Rluc activity. As shown in FIG. 19A, the Rluc activity decreased with increasing concentration of each compound. Based on the Rluc curves, the $EC_{50}$ values (the compound concentration required to inhibit 50% of the Rluc activity) were estimated to be 5.4 µM, 11 µM, and 140 µM for mycophenolic acid, 6-azauridine, and ribavirin, respectively. These $EC_{50}$ values correlate well with the $EC_{50}$ values derived from the standard viral infection assay (8.4 µM, 6.1 µM, and 178 µM, respectively) (Morrey, J., et al. 2002. Antiviral Res. 55:107-116). Longer (48-h) or shorter (12-h) treatment of the cells with the same compounds yielded $EC_{50}$ values several-fold higher than those obtained with the 24-h incubation (data not shown). Discrepancies among the $EC_{50}$ values obtained from longer or shorter treatments are likely because, at 12 h post-treatment, the compound has not reached its inhibition peak, whereas, at 48 h post-treatment, the cells have outgrown the inhibitory effect of the compound. Therefore, incubation of the cells with compound for 24 h yields the highest assay sensitivity.

To increase the throughput of the assay, the experiments were performed in a 96-well format with approximately $5\times10^4$ cells seeded to each well; similar results as described above were obtained (data not shown). These results indicated that the Rluc activity from the cell line could be used for screening inhibitors against WNV in a high-throughput fashion.

To verify that the reduction in Rluc activity reflected the compound inhibition of viral RNA replication, RT-PCR was performed. After 24 h of compound treatment, cells from the 12-well plates were assayed for RNA amounts as described above, except that 12 µl from the 50 µl extracted RNA was used in the real-time RT-PCR assay. Similar to the Rluc results, decreasing amounts of replicon RNA were observed with increasing concentration of inhibitor (FIG. 19B). The relative potencies of the three tested compounds are also similar to those observed with the Rluc results, in the decreasing order of mycophenolic acid, 6-azauridine, and ribavirin (compare FIGS. 19A to 19B). However, the $EC_{50}$ values derived from the RNA copy numbers were much larger than those derived from the Rluc activity results: approximately 100 µM for mycophenolic acid, and greater than 300 µM for 6-azauridine and ribavirin (FIG. 19B). The higher sensitivity of the Rluc-based assay relative to the RNA copy-based assay is likely due to enzymatic signal amplification by the Rluc.

To exclude the possibility that the reduction of Rluc activity and viral RNA copy number was due to cytotoxicity of the compounds, XTT [2,3-Bis(2-methoxy-4-nitro-5-sulfophenyl)-2H-tetrazolium-5-carboxanilide, a substrate for mitochodrial dehydrogenase used for determination of cell viability] was assayed on parental BHK-21 cells. In accordance with previous reports (Jordan, I., et al. 2000. J. Infect. Dis. 182:1214-7; Morrey, J., et al. 2002. Antiviral Res. 55:107-116), no toxicity was observed at 300 µM for any of the three compounds (data not shown). Overall, the above results demonstrated that the Rluc activity reflects the replication level of viral RNA inside the cells, and that the reporting cell line can serve as a high-throughput assay for screening inhibitors of WNV replication.

One of ordinary skill in the art will appreciate that the novel antiviral assay described herein shows that a genetic aproach should be useful for the development of high-throughput assays for anti-flavivirus drug discovery (Shi, P. Y. 2002. Curr. Opin. Investig. Drugs. 3:1567-73; Lo, M. K., et al. 2003. J. Virology 77, 12901-12906). It will be appreciated that the replicon-based assay covers all targets during viral replication, including viral translation, and -and minus-sense RNA synthesis. However, because no structural genes and, therefore no infectious viral particles are involved in the replicon system, the assay does not include targets involved in viral entry, genome encapsidation, and virion maturation. On the other hand, it will be understood that since no infectious virions are formed, the replicon-based assay can be performed in a Biosafety Level 2 (BSL2) laboratory, rather than in a BSL3 containment. Another advantage of the present invention, especially the assay of the lineage I WNV replicon and respective cell-line, is that inhibitors identified through such a cell-based assay should have a high success rate in subsequent animal experiments, since the assay tests the cellular uptake of compounds, and potentially the stability of the compounds inside the cells.

In embodiments where Rluc is the reporter for the system, the assay of the invention may select for potential inhibitors of the Rluc gene rather than inhibitors of viral replication. Rluc inhibitors can be quickly eliminated by testing any hits derived from the replicon-based screening in a recombinant Rluc assay (Chemicon International, Temecula, Calif.). Each of the references cited in the present Example are incorporated herein by reference in their entirety.

It will be further appreciated that the mode of action of any identified viral inhibitor of the present invention can be identified through individual biochemical assays such as RdRp, protease, NTPase, or helicase activity. Alternatively, the mode of action of the compounds could be analyzed through selection of compound-resistant virus followed by mapping of the mutated gene(s) and reverse-engineering of specific mutations into an infectious clone for phenotypic verification. The full-length infectious clone of lineage I WNV and recombinant systems of WNV NS5 RdRp and NS3 NTPase/helicase will facilitate these analyses.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

Ackermann M, Padmanabhan R. (2001) De novo synthesis of RNA by the dengue virus RNA-dependent RNA polymerase exhibits temperature dependence at the initiation but not elongation phase. J Biol Chem 2001 Oct. 26; 276(43):39926-37.

Aitken, M. A. *Molecular Biomethods Handbook*, Chapter 20, p. 235-250.

Arias C F, Preugschat F, Strauss J H. (1993) Dengue 2 virus NS2B and NS3 form a stable complex that can cleave NS3 within the helicase domain. Virology 1993 April; 193(2):888-99.

Beasley, D. W. C. et al, (2001) International Conference on the West Nile Virus, New York Academy of Science Poster Section 1:5.

Blackwell J. L., and Brinton M. A. (1995) BHK cell proteins that bind to the 3' stem-loop structure of the West Nile virus genome RNA. J Virol 1995 September; 69(9): 5650-8.

Blackwell J L, Brinton M A. (1997) Translation elongation factor-1 alpha interacts with the 3' stem-loop region of West Nile virus genomic RNA. J Virol 71(9):6433-44.

Brinton M A, Dispoto J H, (1988) Sequence and secondary structure analysis of the 5'-terminal region of flavivirus genome RNA. Virology 1988 February; 162(2):290-9.

Campbell M S, Pletnev A G: Infectious cDNA clones of Langat tickborne flavivirus that differ from their parent in peripheral neurovirulence. Virology (2000) 269(1):225-237.

Cardosa, M. J., (1998) Dengue vaccine design: issues and challenges. Br Med Bull 1998; 54(2):395-405.

Chambers T. J., Hahn C S, Galler R, Rice C M (1990) Flavivirus genome organization, expression, and replication. Annu Rev Microbiol 44:649-88.

Chambers T J, Grakoui A, Rice C M. (1991) Processing of the yellow fever virus nonstructural polyprotein: a catalytically active NS3 proteinase domain and NS2B are required for cleavages at dibasic sites. J Virol 1991 November; 65(11):6042-50.

Chambers T J, Nestorowicz A, Amberg S M, Rice C M. (1993) Mutagenesis of the yellow fever virus NS2B protein: effects on proteolytic processing, NS2B-NS3 complex formation, and viral replication. J Virol 1993 November; 67(11):6797-807.

Collins, M. K., *Methods in Molecular Biology*, Human Press, v. 8 (1991).

Diamond M S, Edgil D, Roberts T G, Lu B, Harris E. (2000) Infection of human cells by dengue virus is modulated by different cell types and viral strains. J Virol 2000 September; 74(17):7814-23.

De Clercq, E. 1993. Antiviral agents: characteristic activity spectrum depending on the molecular target with which they interact. Advance Virus Res. 42:1-55. Ebel, G. D., Dupuis, A. P., II, Ngo, K. A., Nicholas, D. C., Kaauffman, E. B., Johnes, S. A., Yound, D., Maffei, J., Shi, P. Y., Bernard, K. A., and Kramer L. D. (2001). Partial genetic characterization of West Nile virus strains, New York State, 2000. Emerg. Infect. Dis. 7:650-653.

Falgout B, Miller R H, Lai C J. (1993) Deletion analysis of dengue virus type 4 nonstructural protein NS2B: identification of a domain required for NS2B-NS3 protease activity. J Virol 1993 April; 67(4):2034-42.

Gray, N. K. and M. Wicker, (1998) Control of translation in animals, Annu. Rev. Cell Dev. Biol. 14: 399-458.

Guyatt K J, Westaway E G, Khromykh A A. (2001) Expression and purification of enzymatically active recombinant RNA-dependent RNA polymerase (NS5) of the flavivirus Kunjin. J Virol Methods 2001 March; 92(1):37-44.

Hayes, C. G., *The Arboviruses: Epidemiology and Ecology*, T. P. Monathy, ed., CRC, Boca Raton, Fla., vol. 5, chapter 49 (1989)

Hicks, B. W. *Green Fluorescent Protein: Applications and Protocols*, Vol. 83 of Methods in Cell Biology (2002).

Heinz F X, Allison S L (2000) Structures and mechanisms in flavivirus fusion. Adv Virus Res 2000; 55:231-69.

Hellen C U, Witherell G W, Schmid M, Shin S H, Pestova T V, Gil A, Wimmer E. (1993) A cytoplasmic 57-kDa protein that is required for translation of picornavirus RNA by internal ribosomal entry is identical to the nuclear pyrimidine tract-binding protein. Proc Natl Acad Sci 90(16):7642-6.

Hubalek, Z., and J. Halouzka. (1999) West Nile fever—a reemerging mosquito-borne viral disease in Europe. Emerg Infect Dis 5(5):643-50.

Hurrelbrink R J, Nestorowicz A, McMinn P C: Characterization of Infectious Murray Valley encephalitis virus derived from a stably cloned genomelength cDNA. *J Gen Viral* (1999) 80(Pt 12):3115-3125.

Jackson R J, Kaminski A. (1995) Internal initiation of translation in eukaryotes: the picornavirus paradigm and beyond. RNA 1995 Dec.; 1(10):985-1000.

Jang S K, Krausslich H G, Nicklin M J, Duke G M, Palmenberg A C, Wimmer E. (1988) A segment of the 5' nontranslated region of encephalomyocarditis virus RNA directs internal entry of ribosomes during in vitro translation. J Virol 1988 August; 62(8):2636-43.

Jordan I, Briese T, Fischer N, Lau J Y, Lipkin W I: Ribavirin inhibits West Nile virus replication and cytopathic effect In neural cells. J *Infect D*1s (2000) 182(4):1214-1217.

Kapoor M, Zhang L, Mohan P M, Padmanabhan R: Synthesis and characterization of an Infectious dengue virus type-2 RNA genome (New Guinea C strain). Gene (1995) 162(2):175-180.

Kaminski A, Hunt S L, Patton J G, Jackson R J. (1995) Direct evidence that polypyrimidine tract binding protein (PTB) is essential for internal initiation of translation of encephalomyocarditis virus RNA. RNA 1995 Nov.; 1(9): 924-38.

Khromykh A A, Westaway E G: Completion of Kunjin virus RNA sequence and recovery of an Infectious RNA transcribed from stably cloned full-length cDNA. *J Virol* (1994) 68(7):4580-4588.

Khromykh A A. Westaway E G: Subgenomic replicons of the flavivirus Kunjin: Construction and applications. *J* Virol (1997) 71(2):1497-1505.

Koonin E V. (1993) Computer-assisted identification of a putative methyltransferase domain in NS5 protein of flaviviruses and lambda 2 protein of reovirus. J Gen Virol 1993 April; 74 (Pt 4):733-40.

Kummerer B M, Rice C M. (2002) Mutations in the yellow fever virus nonstructural protein NS2A selectively block production of infectious particles. J Virol 2002 May; 76(10):4773-84.

Lai C J, Zhao B T, Hod H, Bray M: Infectious RNA transcribed from stably cloned full-length cDNA of dengue type 4 virus. Proc Natl Acad Sci USA (1991) 88(12):5139-5143.

Lanciotti R S, Roehrig J T, Deubel V, Smith J, Parker M, Steele K, Crise B, Volpe K E, Crabtree M B, Scherret J H, Hall R A, MacKenzie J S, Cropp C B, Panigrahy B, Ostlund E, Schmitt B, Malkinson M, Banet C, Weissman J, Komar N, Savage H M, Stone W, McNamara T, Gubler D J. (1999) Origin of the West Nile virus responsible for an outbreak of encephalitis in the northeastern United States. Science 286 (5448):2333-7.

Lanciotti R S, Ebel G D, Deubel V, Kerst A J, Murri S, Meyer R, Bowen M, McKinney N, Morrill W E, Crabtree M B, Kramer L D, Roehrig J T. (2002) Complete genome sequences and phylogenetic analysis of West Nile virus strains isolated from the United States, Europe, and the Middle East. Virology 298(1):96-105.

Leda, R., *Methods in Molecular Biology*, Humana Press, v. 165 (2001).

Lindenbach, B. D. and C. M. Rice, *Fields Virology*, Fourth Edition, volume 1 D. M. Knipe and P. M. Howley, ed, Lippincott Williams and Wilkins, Philadelphia, Pa.

Lindenbach B D, Rice C M. (1997) trans-Complementation of yellow fever virus NS1 reveals a role in early RNA replication. J Virol 1997 December; 71(12):9608-17.

Lindenbach B D, Rice C M. (1999) Genetic interaction of flavivirus nonstructural proteins NS1 and NS4A as a determinant of replicase function. J Virol 1999 June; 73(6):4611-21.

Lo, J. K., Tilgner, M., and Shi, P. Y. 2003. A potential high-throughput assay for screening inhibitors of West Nile virus replication. J. Virol. 77, 12901-12906.

Mandl C W, Ecker M, Holzmann H, Kunz C, Heinz F X: Infectious cDNA clones of tick-borne encephalitis virus European subtype prototypic strain Neudoerfl and high virulence strain Hypr. *J* Gen Virol (1997) 78(Pt 5):1049-1057.

McSharry J J. (1994) Uses of flow cytometry in virology. Clin Microbiol Rev 1994 Oct.; 7(4):576-604.

McSharry J J. (2000) Analysis of virus-infected cells by flow cytometry. Methods 2000 Jul.; 21 (3):249-57.

Meerovitch K, Svitkin Y V, Lee H S, Lejbkowicz F, Kenan D J, Chan E K, Agol V I, Keene J D, Sonenberg N. (1993) La autoantigen enhances and corrects aberrant translation of poliovirus RNA in reticulocyte lysate J Virol 1993 July; 67(7):3798-807.

Monath, T. 2001. Prospects for development of a vaccine against the West Nile virus. Ann. N.Y. Acad. Sci. 951:1-12.

Morrey J D, Smee D F, Sidwell R W, Tsang C: Identification of active antiviral compounds against a New York Isolate of West Nile virus. Antiviral Res (2002) 55(1):107-116.

Muylaert I R, Chambers T J, Galler R, Rice C M. (1996) Mutagenesis of the N-linked glycosylation sites of the yellow fever virus NS1 protein: effects on virus replication and mouse neurovirulence. Virology 1996 Aug. 1;222(1): 159-68.

Muylaert I R, Galler R, Rice C M. (1997) Genetic analysis of the yellow fever virus NS1 protein: identification of a temperature-sensitive mutation which blocks RNA accumulation. J Virol 1997 January; 71(1):291-8.

Parham, P. *Immunology* New York, Garland Press (2000)

Pelletier J, Kaplan G, Racaniello V R, Sonenberg N. (1988) Cap-independent translation of poliovirus mRNA is conferred by sequence elements within the 5' noncoding region Mol Cell Biol 8(3):1103-12.

Pelletier J, Kaplan G, Racaniello V R, Sonenberg N. (1998) Translational efficiency of poliovirus mRNA: mapping inhibitory cis-acting elements within the 5' noncoding region. J Virol 62(7):2219-27.

Pestova T V, Shatsky I N, Fletcher S P, Jackson R J, Hellen C U. (1998) A prokaryotic-like mode of cytoplasmic eukaryotic ribosome binding to the initiation codon during internal translation initiation of hepatitis C and classical swine fever virus RNAs. Genes Dev 12(1):67-83.

Polo S, Ketner G, Levis R, Falgout 8: Infectious RNA transcripts from full-length dengue virus type 2 cDNA clones made in yeast. *J* Virol (1997) 71(7):5366-5374.

Proutski V, Gould E A, Holmes E C. (1997) Secondary structure of the 3' untranslated region of flaviviruses: similarities and differences. Nucleic Acids Res 1997 Mar. 15; 25(6):1194-1202.

Rauscher S, Flamm C, Mandl C W, Heinz F X, Stadler P F. (1997) Secondary structure of the 3'-noncoding region of flavivirus genomes: comparative analysis of base pairing probabilities. RNA 3(7):779-91.

Rey F A, Heinz F X, Mandl C, Kunz C, Harrison S C (1995) The envelope glycoprotein from tick-borne encephalitis virus at 2 A resolution. Nature 1995 May 25; 375(6529): 291-8.

Rice C M, Lendxes E M. Eddy S R, Shin S J, Sheets R L, Strauss J H: Nucleotide sequence of yellow fever virus: Implications for flavivirus gene expression and evolution. Science (1985) 229(4715):726-733.

Sambrook, J. and D. W. Russell, *Molecular Cloning: A Laboratory Manual*, Third Edition (2001).

Shi, P. Y. 2002. Strategies for the identification of inhibitors of West Nile virus and other flaviviruses. Curr. Opin. Investig. Drugs. 3:1567-73.

Shi, P. Y., E. B. Kauffman, P. Ren, A. Felton, J. H. Tai, A. P. Dupuis, 2nd, S. A. Jones, K. A. Ngo, D. C. Nicholas, J. Maffei, G. D. Ebel, K. A. Bernard, and L. D. Kramer. 2001. High-throughput detection of West Nile virus RNA. J. Clin. Microbiol. 39:1264-71.

Shi, P. Y., M. Tilgner, and M. K. Lo. 2002. Construction and characterization of subgenomic replicons of New York strain of West Nile virus. Virology 296:219-233.

Shi, P. Y., M. Tilgner, M. K. Lo, K. A. Kent, and K. A. Bernard. 2002. Infectious cDNA clone of the epidemic west nile virus from New York City. J. Virol. 76:5847-56.

Specter, S. C. et al., *Clinical Virology Manual*, $3^{rd}$ Edition, ASM Press, (2000).

Sumiyoshi H, Hoke C H, Trent D W: Infectious Japanese encephalitis virus RNA can be synthesized from In vitro-ligated cDNA templates. *J* Virol (1992) 66(9):5425-5431.

Svitkin Y V, Meerovitch K, Lee H S, Dholakia J N, Kenan D J, Agol V I, Sonenberg N. (1994) Internal translation initiation on poliovirus RNA: further characterization of La function in poliovirus translation in vitro. J Virol 1994 March; 68(3): 1544-50.

Tan B H, Fu J, Sugrue R J, Yap E H, Chan Y C, Tan Y H. (1996) Recombinant dengue type 1 virus NS5 protein expressed in *Escherichia coli* exhibits RNA-dependent RNA polymerase activity. Virology 1996 Feb. 15; 216(2):317-25.

Wu S-F, Lee C J, Liao C-L, Dwek R, Zitzmann N, Lin Y-L: Antiviral effects of an iminosugar derivative on flavivirus Infections. *J* Virol (2002) 76(8):3596-3604.

Yamshchikov V F, Wangler G, Perelygin A A, Brinton M A, Compans R W: An infectious clone of the West Nile flavivirus. Virology (2001) 281(2):294-304.

We claim:

1. A DNA molecule comprising a DNA sequence encoding a mRNA of a lineage I WNV genome wherein the nucleotide sequence is as set forth in SEQ ID NO.2, said DNA sequence having a 5' and a 3' end, said DNA molecule adapted to report the transcription of said DNA sequence, said DNA molecule comprising:
   (a) a deletion in said DNA sequence corresponding to one or more structural genes of said lineage I WNV genome;
   (b) a promoter at said 5' end of said DNA sequence;
   (c) a nucleotide sequence encoding a reporter at said 3' end of the DNA sequence;
wherein said promoter is operably linked and adapted to control the transcription of said DNA sequence and said nucleotide sequence encoding said reporter.

2. The DNA molecule according to claim 1, wherein said reporter is selected from the group consisting of luciferase, green fluorescent protein, beta-glactosidase, peptidase, glycosidase, phosphatase, a fluorescent protein, and an antibiotic resistance marker.

3. The DNA molecule according to claim 1, where said reporter is green fluorescent protein.

4. The DNA molecule according to claim 1, wherein said one or more structural genes is selected from the group consisting of the capsid, envelope, and membrane genes.

5. The DNA molecule according to claim 1, wherein said deletion is in the capsid, envelope, and membrane genes of said lineage I WNV genome.

6. The DNA molecule according to claim 1, wherein said promoter is selected from the group consisting of SP6, T7, and T3.

7. The DNA molecule according to claim 1, wherein said DNA molecule contains a second nucleotide sequence encoding a reporter, wherein transcription of said second nucleotide sequence encoding said second reporter under control of said promoter.

8. The DNA molecule according to claim 7, wherein the second reporter is selected from the group consisting of luciferase, green fluorescent protein, beta-glactosidase, oxidase, peptidase, glycosidase, phosphatase, a fluorescent protein, and an antibiotic resistance marker.

9. The DNA molecule according to claims 7, wherein the first and second nucleotide sequences encoding first and second reporters are optionally preceded by an internal ribosome entry site (IRES), wherein said IRES facilitates translation of said first and second reporters.

10. The DNA molecule according to claim 1, wherein the DNA sequence is a lineage I WNV replicon and said reporter is GFP or luciferase.

11. A DNA molecule comprising a DNA sequence encoding a full-length and fully-infectious mRNA of a lineage I WNV genome, wherein said lineage I WNV nucleotide sequence is as set forth in SEQ ID NO.2 said DNA sequence having a 5' and a 3' end, said DNA molecule adapted to report the transcription of said DNA sequence, said DNA molecule comprising:
   (a) a promoter at said 5' end of said DNA sequence;
   (b) a first nucleotide sequence encoding a first reporter gene at said 3' end of the DNA sequence;
wherein said promoter is adapted to control the transcription of said DNA sequence and said reporter gene.

12. The DNA molecule according to claim 11, wherein said reporter is selected from the group consisting of luciferase, green fluorescent protein, beta-glactosidase, oxidase, peptidase, glycosidase, phosphatase, a fluorescent protein, and an antibiotic resistance marker.

13. The DNA molecule according to claim 11, where said first reporter is green fluorescent protein.

14. The DNA molecule according to claim 11, wherein said promoter is selected from the group consisting of SP6, T7, and T3.

15. The DNA molecule according to claim 11, wherein said DNA molecule comprises a second nucleotide sequence encoding a second reporter, wherein the transcription of said second nucleotide sequence encoding the second reporter is under control of said promoter.

16. The DNA molecule according to claim 15, wherein the second reporter is selected from the group consisting of luciferase, green fluorescent protein, beta-glactosidase, oxidase, peptidase, glycosidase, phosphatase, a fluorescent protein, and an antibiotic resistance marker.

17. The DNA molecule according to claims 16, wherein the first and second nucleotide sequences encoding said first and second reporters are optionally preceded by an internal ribosome entry site (IRES), wherein said IRES facilitates translation of said first and second reporters.

18. A cell line comprising the DNA molecule according to claim 1.

19. A reverse genetics system for screening and identifying antiflaviviral compounds comprising a lineage I WNV cDNA clone wherein the full-length lineage I WNV cDNA clone is according to the nucleotide sequence is as set forth in SEQ ID NO:2.

* * * * *

SEQUENCE LISTING

<160> NUMBER OF SEQ ID NOS: 28

<210> SEQ ID NO 1
<211> LENGTH: 11029
<212> TYPE: DNA
<213> ORGANISM: West Nile virus

<400> SEQUENCE: 1

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcaa | tatgctaaaa | cgcggaatgc | cccgcgtgtt | gtccttgatt | 180 |
| ggactgaaga | gggctatgtt | gagcctgatc | gacggcaagg | ggccaatacg | atttgtgttg | 240 |
| gctctcttgg | cgttcttcag | gttcacagca | attgctccga | cccgagcagt | gctggatcga | 300 |
| tggagaggtg | tgaacaaaca | aacagcgatg | aaacaccttc | tgagttttaa | gaaggaacta | 360 |
| gggaccttga | ccagtgctat | caatcggcgg | agctcaaaac | aaaagaaaag | aggaggaaag | 420 |
| accggaattg | cagtcatgat | tggcctgatc | gccagcgtag | gagcagttac | cctctctaac | 480 |
| ttccaaggga | aggtgatgat | gacggtaaat | gctactgacg | tcacagatgt | catcacgatt | 540 |
| ccaacagctc | ctggaaagaa | cctatgcatt | gtcagagcaa | tggatgtggg | atacatgtgc | 600 |
| gatgatacta | tcacttatga | atgccagtg | ctgtcggctg | gtaatgatcc | agaagacatc | 660 |
| gactgttggt | gcacaaagtc | agcagtctac | gtcaggtatg | gaagatgcac | caagacacgc | 720 |
| cactcaagac | gcagtcggag | gtcactgaca | gtgcagacac | acggagaaag | cactctagcg | 780 |
| aacaagaagg | gggcttggat | ggacagcacc | aaggccacaa | ggtatttggt | aaaaacagaa | 840 |
| tcatggatct | tgaggaaccc | tggatatgcc | ctggtggcag | ccgtcattgg | ttggatgctt | 900 |
| gggagcaaca | ccatgcagag | agttgtgttt | gtcgtgctat | tgcttttggt | ggccccagct | 960 |
| tacagcttca | actgccttgg | aatgagcaac | agagacttct | tggaaggagt | gtctggagca | 1020 |
| acatgggtgg | atttggttct | cgaaggcgac | agctgcgtga | ctatcatgtc | taaggacaag | 1080 |
| cctaccatcg | atgtgaagat | gatgaatatg | gaggcggcca | acctggcaga | ggtccgcagt | 1140 |
| tattgctatt | tggctaccgt | cagcgatctc | tccaccaaag | ctgcgtgccc | gaccatggga | 1200 |
| gaagctcaca | atgacaaacg | tgctgaccca | gcttttgtgt | gcagacaagg | agtggtggac | 1260 |
| aggggctggg | gcaacggctg | cggattattt | ggcaaaggaa | gcattgacac | atgcgccaaa | 1320 |
| tttgcctgct | ctaccaaggc | aataggaaga | accatcttga | aagagaatat | caagtacgaa | 1380 |
| gtggccattt | ttgtccatgg | accaactact | gtggagtcgc | acggaaacta | ctccacacag | 1440 |
| gttggagcca | ctcaggcagg | agattcagc | atcactcctg | cggcgccttc | atacacacta | 1500 |
| aagcttggag | aatatggaga | ggtgacagtg | gactgtgaac | cacggtcagg | gattgacacc | 1560 |
| aatgcatact | acgtgatgac | tgttggaaca | aagacgttct | tggtccatcg | tgagtggttc | 1620 |
| atggacctca | acctcccttg | gagcagtgct | ggaagtactg | tgtggaggaa | cagagagacg | 1680 |
| ttaatggagt | ttgaggaacc | acacgccacg | aagcagtctg | tgatagcatt | gggctcacaa | 1740 |
| gagggagctc | tgcatcaagc | tttggctgga | gccattcctg | tggaattttc | aagcaacact | 1800 |
| gtcaagttga | cgtcgggtca | tttgaagtgt | agagtgaaga | tggaaaaatt | gcagttgaag | 1860 |
| ggaacaacct | atggcgtctg | ttcaaaggct | ttcaagtttc | ttgggactcc | cgcagacaca | 1920 |
| ggtcacggca | ctgtggtgtt | ggaattgcag | tacactggca | cggatggacc | ttgtaaagtt | 1980 |
| cctatctcgt | cagtggcttc | attgaacgac | ctaacgccag | tgggcagatt | ggtcactgtc | 2040 |

```
aacccttttg tttcagtggc cacggccaac gctaaggtcc tgattgaatt ggaaccaccc   2100
tttggagact catacatagt ggtgggcaga ggagaacaac agatcaatca ccattggcac   2160
aagtctggaa gcagcattgg caaagccttt acaaccaccc tcaaaggagc gcagagacta   2220
gccgctctag gagacacagc ttgggacttt ggatcagttg gaggggtgtt cacctcagtt   2280
gggaaggctg tccatcaagt gttcggagga gcattccgct tactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcacgctg acactgggtg tgccatagac atcagccggc aagagctgag atgtggaagt   2520
ggagtgttca tacacaatga tgtggaggct tggatggacc gatacaagta ttaccctgaa   2580
acgccacaag gcctagccaa gatcattcag aaagctcata aggaaggagt gtgcggtcta   2640
cgatcagttt ccagactgga gcatcaaatg tgggaagcag tgaaggacga gctgaacact   2700
cttttgaagg agaatggtgt ggaccttagt gtcgtggttg agaaacagga gggaatgtac   2760
aagtcagcac ctaaacgcct caccgccacc acggaaaaat tggaaattgg ctggaaggcc   2820
tggggaaaga gtattttatt tgcaccagaa ctcgccaaca acacctttgt ggttgatggt   2880
ccggagacca aggaatgtcc gactcagaat cgcgcttgga atagcttaga agtggaggat   2940
tttggatttg gtctcaccag cactcggatg ttcctgaagg tcagagagag caacacaact   3000
gaatgtgact cgaagatcat tggaacggct gtcaagaaca acttggcgat ccacagtgac   3060
ctgtcctatt ggattgaaag caggctcaat gatacgtgga agcttgaaag ggcagttctg   3120
ggtgaagtca aatcatgtac gtggcctgag acgcatacct tgtggggcga tggaatcctt   3180
gagagtgact tgataatacc agtcacactg gcgggaccac gaagcaatca caatcggaga   3240
cctgggtaca agacacaaaa ccagggccca tgggacgaag gccgggtaga gattgacttc   3300
gattactgcc caggaactac ggtcacccta agtgagagct gcggacaccg tggacctgcc   3360
actcgcacca ccacagagag cggaaagttg ataacagatt ggtgctgcag gagctgcacc   3420
ttaccaccac tgcgctacca aactgacagc ggctgttggt atggtatgga gatcagacca   3480
cagagacatg atgaaaagac cctcgtgcag tcacaagtga atgcttataa tgctgatatg   3540
attgacccct tcagttggg ccttctggtc gtgttcttgg ccaccaggg ggtccttcgc   3600
aagaggtgga cagccaagat cagcatgcca gctatactga ttgctctgct agtcctggtg   3660
tttgggggca ttacttacac tgatgtgtta cgctatgtca tcttggtggg ggcagctttc   3720
gcagaatcta attcgggagg agacgtggta cacttggcgc tcatggcgac cttcaagata   3780
caaccagtgt ttatggtggc atcgtttctc aaagcgagat ggaccaacca ggagaacatt   3840
ttgttgatgt tggcggctgt tttctttcaa atggcttatc acgatgcccg ccaaattctg   3900
ctctgggaga tccctgatgt gttgaattca ctggcggtag cttggatgat actgagagcc   3960
ataacattca caacgacatc aaacgtggtt gttccgctgc tagcccctgct aacacccggg   4020
ctgagatgct tgaatctgga tgtgtacagg atactgctgt tgatggtcgg aataggcagc   4080
ttgatcaggg agaagaggag tgcagctgca aaaagaaag gagcaagtct gctatgcttg   4140
gctctagcct caacaggact tttcaacccc atgatccttg ctgctggact gattacatgt   4200
gatcccaacc gtaaacgcgg atggcccgca actgaagtga tgacagctgt cggcctgatg   4260
tttgccatcg tcggagggct ggcagagctt gacattgact ccatggccat tccaatgact   4320
atcgcggggc tcatgtttgc tgctttcgtg atttctggga aatcaacaga tatgtggatt   4380
```

```
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac ccctgggca     4560 atcttgccct cagtagttgg attttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa    4740
ggtgttttcc acacccttg gcatacaaca aaaggagccg cttttgatgag cggagagggc    4800 cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg cgccggtaa acaaggagg      5220 attctgccac agatcatcaa agaggccata acagaagac tgagaacagc cgtgctagca     5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc taggggaggc ggcggcaata ttcatgacag ccaccccacc aggcacttca    5580
gatccattcc cagagtccaa ttcaccaatt tccgacttac agactgagat cccggatcga    5640
gcttggaact ctggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atgggggcta actttaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggga    6180 taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg gtgaaaggaa gattctgagg ccgcgctgga ttgacgccag ggtgtactcg    6420
gatcaccagg cactaaaggc gttcaaggac ttcgcctcgg gaaacgttc tcagataggg    6480 ctcattgagg ttctgggaaa gatgcctgag cacttcatgg ggaagacatg ggaagcactt    6540
gacaccatgt acgttgtggc cactgcagag aaaggaggaa gagctcacag aatgcctg     6600 gaggaactgc cagatgctct tcagacaatt gccttgattg ccttattgag tgtgatgacc    6660
atgggagtat tcttcctcct catgcagcgg aagggcattg aaagatagg tttgggaggc    6720 gctgtcttgg gagtcgcgac cttttttctgt tggatggctg aagttccagg aacgaagatc    6780
```

```
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttctggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg gaattttgat cacggccgca gcggtgacgc tttgggagaa tggagcaagc    7560 tctgttttgga acgcaacaac tgccatcgga ctctgccaca tcatgcgtgg gggttggttg    7620
tcatgtctat ccataacatg gacactcata agaacatgg aaaaaccagg actaaaaga    7680 ggtgggcaa aaggacgcac cttgggagag gtttggaaag aaagactcaa ccagatgaca    7740
aaagaagagt tcactaggta ccgcaaagag gccatcatcg aagtcgatcg ctcagcagca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca agttatgga    8040 tggaacattg tcaccatgaa gagtggggtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaatttttgc    8220 gtgaaggtgc tctgcccta catgccgaaa gtcatagaga agatggagct gctccaacgc    8280
cggtatgggg gggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggacccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atgagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaggc agttgaagat ccaaaatttt gggagatggt ggatgaggag    9000
cgcgaggcac atctgcgggg ggaatgtcac acttgcattt acaacatgat gggaagagaa    9060
gagaaaaaac ccggagagtt cggaaaggcc aagggaagca gagccatttg gttcatgtgg    9120
```

-continued

| | |
|---|---|
| ctcggagctc gctttctgga gttcgaggct ctgggttttc tcaatgaaga ccactggctt | 9180 |
| ggaagaaaga actcaggagg aggtgtcgag ggcttgggcc tccaaaaact gggttacatc | 9240 |
| ctgcgtgaag ttggcacccg gcctgggggc aagatctatg ctgatgacac agctggctgg | 9300 |
| gacacccgca tcacgagagc tgacttggaa atgaagcta aggtgcttga gctgcttgat | 9360 |
| ggggaacatc ggcgtcttgc cagggccatc attgagctca cctatcgtca caaagttgtg | 9420 |
| aaagtgatgc gcccggctgc tgatggaaga accgtcatgg atgttatctc cagagaagat | 9480 |
| cagaggggga gtggacaagt tgtcacctac gccctaaaca ctttcaccaa cctggccgtc | 9540 |
| cagctggtga ggatgatgga aggggaagga gtgattggcc cagatgatgt ggagaaactc | 9600 |
| acaaaaggga aaggacccaa agtcaggacc tggctgtttg agaatgggga agaaagactc | 9660 |
| agccgcatgc tgtcagtgg agatgactgt gtggtaaagc ccctggacga tcgctttgcc | 9720 |
| acctcgctcc acttcctcaa tgctatgtca aaggttcgca agacatcca agagtggaaa | 9780 |
| ccgtcaactg gatggtatga ttggcagcag gttccatttt gctcaaacca tttcactgaa | 9840 |
| ttgatcatga agatggaag aacactggtg gttccatgcc gaggacagga tgaattggta | 9900 |
| ggcagagctc gcatatctcc aggggccgga tggaacgtcc gcgacactgc ttgtctggct | 9960 |
| aagtcttatg cccagatgtg gctgcttctg tacttccaca gaagagacct gcggctcatg | 10020 |
| gccaacgcca tttgctccgc tgtccctgtg aattgggtcc ctaccggaag aaccacgtgg | 10080 |
| tccatccatg caggaggaga gtggatgaca acagaggaca tgttggaggt ctggaaccgt | 10140 |
| gtttggatag aggagaatga atggatgaa gacaaaaccc cagtggagaa atggagtgac | 10200 |
| gtcccatatt caggaaaacg agaggacatc tggtgtggca gcctgattgg cacaagagcc | 10260 |
| cgagccacgt gggcagaaaa catccaggtg gctatcaacc aagtcagagc aatcatcgga | 10320 |
| gatgagaagt atgtggatta catgagttca ctaaagagat atgaagacac aacttttggtt | 10380 |
| gaggacacag tactgtagat atttaatcaa ttgtaaatag acaatataag tatgcataaa | 10440 |
| agtgtagttt tatagtagta tttagtggtg ttagtgtaaa tagttaagaa aattttgagg | 10500 |
| agaaagtcag gccgggaagt tcccgccacc ggaagttgag tagacggtgc tgcctgcgac | 10560 |
| tcaaccccag gaggactggg tgaacaaagc cgcgaagtga tccatgtaag ccctcagaac | 10620 |
| cgtctcggaa ggaggacccc acatgttgta acttcaaagc ccaatgtcag accacgctac | 10680 |
| ggcgtgctac tctgcggaga gtgcagtctg cgatagtgcc ccaggaggac tgggttaaca | 10740 |
| aaggcaaacc aacgccccac gcggcccctag ccccggtaat ggcgttaacc agggcgaaag | 10800 |
| gactagaggt tagaggagac cccgcggttt aaagtgcacg gcccagcctg ctgaagctg | 10860 |
| taggtcaggg gaaggactag aggttagtgg agaccccgtg ccacaaaaca ccacaacaaa | 10920 |
| acagcatatt gacacctggg atagactagg agatcttctg ctctgcacaa ccagccacac | 10980 |
| ggcacagtgc gccgacaatg gtggctggtg gtgcgagaac acaggatct | 11029 |

<210> SEQ ID NO 2
<211> LENGTH: 11029
<212> TYPE: DNA
<213> ORGANISM: West Nile virus

<400> SEQUENCE: 2

| | |
|---|---|
| agtagttcgc ctgtgtgagc tgacaaactt agtagtgttt gtgaggatta acaacaatta | 60 |
| acacagtgcg agctgtttct tagcacgaag atctcgatgt ctaagaaacc aggagggccc | 120 |
| ggcaagagcc gggctgtcaa tatgctaaaa cgcggaatgc cccgcgtgtt gtccttgatt | 180 |
| ggactgaaga gggctatgtt gagcctgatc gacggcaagg ggccaatacg atttgtgttg | 240 |

-continued

```
gctctcttgg cgttcttcag gttcacagca attgctccga cccgagcagt gctggatcga    300
tggagaggtg tgaacaaaca aacagcgatg aaacaccttc tgagttttaa gaaggaacta    360
gggaccttga ccagtgctat caatcggcgg agctcaaaac aaaagaaaag aggaggaaag    420
accggaattg cagtcatgat tggcctgatc gccagcgtag gagcagttac cctctctaac    480
ttccaaggga aggtgatgat gacggtaaat gctactgacg tcacagatgt catcacgatt    540
ccaacagctg ctggaaagaa cctatgcatt gtcagagcaa tggatgtggg atacatgtgc    600
gatgatacta tcacttatga atgcccagtg ctgtcggctg taatgatcc agaagacatc     660 gactgttggt gcacaaagtc agcagtctac gtcaggtatg aagatgcac caagacacgc     720 cactcaagac gcagtcggag gtcactgaca gtgcagacac acggagaaag cactctagcg    780
aacaagaagg gggcttggat ggacagcacc aaggccacaa ggtatttggt aaaaacagaa    840
tcatggatct tgaggaaccc tggatatgcc ctggtggcag ccgtcattgg ttggatgctt     900
gggagcaaca ccatgcagag agttgtgttt gtcgtgctat tgctttggt ggccccagct     960 tacagcttca actgccttgg aatgagcaac agagacttct tggaaggagt gtctggagca    1020
acatgggtgg atttggttct cgaaggcgac agctgcgtga ctatcatgtc taaggacaag    1080
cctaccatcg atgtgaagat gatgaatatg gaggcggcca acctggcaga ggtccgcagt    1140
tattgctatt tggctaccgt cagcgatctc tccaccaaag ctgcgtgccc gaccatggga    1200
gaagctcaca atgacaaacg tgctgaccca gcttttgtgt gcagacaagg agtggtggac    1260
aggggctggg gcaacggctg cggactattt ggcaaaggaa gcattgacac atgcgccaaa    1320
tttgcctgct ctaccaaggc aataggaaga accatcttga agagaatat caagtacgaa     1380 gtggccattt ttgtccatgg accaactact gtggagtcgc acgaaaacta ctccacacag    1440
gttggagcca ctcaggcagg agattcagc atcactcctg cggcgccttc atacacacta     1500
aagcttggag aatatggaga ggtgacagtg gactgtgaac cacggtcagg gattgacacc    1560
aatgcatact acgtgatgac tgttggaaca aagacgttct tggtccatcg tgagtggttc    1620
atggacctca acctcccttg gagcagtgct ggaagtactg tgtggaggaa cagagagacg    1680
ttaatggagt ttgaggaacc acacgccacg aagcagtctg tgatagcatt gggctcacaa    1740
gagggagctc tgcatcaagc tttggctgga gccattcctg tggaattttc aagcaacact    1800
gtcaagttga cgtcgggtca tttgaagtgt agagtgaaga tggaaaaatt gcagttgaag    1860
ggaacaacct atggcgtctg ttcaaaggct ttcaagtttc ttgggactcc cgcagacaca    1920
ggtcacggca ctgtggtgtt ggaattgcag tacactggca cggatggacc ttgtaaagtt    1980
cctatctcgt cagtggcttc attgaacgac ctaacgccag tgggcagatt ggtcactgtc    2040
aacccttttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag agacacagc ttgggacttt ggatcagttg gagggtgtt cacctcagtt      2280 gggaaggctg tccatcaagt gttcggagga gcattccgct tactgttcgg aggcatgtcc    2340
tggataacgc aaggattgct gggggctctc ctgttgtgga tgggcatcaa tgctcgtgat    2400
aggtccatag ctctcacgtt tctcgcagtt ggaggagttc tgctcttcct ctccgtgaac    2460
gtgcacgctg acactgggtg tgccatagac atcagccggc aagagctgag atgtggaagt    2520
ggagtgttca tacacaatga tgtggaggct tggatggacc gatacaagta ttaccctgaa    2580
```

```
acgccacaag gcctagccaa gatcattcag aaagctcata aggaaggagt gtgcggtcta   2640
cgatcagttt ccagactgga gcatcaaatg tgggaagcag tgaaggacga gctgaacact   2700
cttttgaagg agaatggtgt ggaccttagt gtcgtggttg agaaacagga gggaatgtac   2760
aagtcagcac ctaaacgcct caccgccacc acggaaaaat tggaaattgg ctggaaggcc   2820
tggggaaaga gtattttatt tgcaccagaa ctcgccaaca acacctttgt ggttgatggt   2880
ccggagacca aggaatgtcc gactcagaat cgcgcttgga atagcttaga agtggaggat   2940
tttggatttg gtctcaccag cactcggatg ttcctgaagg tcagagagag caacacaact   3000
gaatgtgact cgaagatcat ggaacggct gtcaagaaca acttggcgat ccacagtgac   3060
ctgtcctatt ggattgaaag caggctcaat gatacgtgga agcttgaaag gcagttctg   3120 ggtgaagtca aatcatgtac gtggcctgag acgcatacct tgtggggcga tggaatcctt   3180
gagagtgact tgataatacc agtcacactg gcggaccac gaagcaatca caatcggaga   3240
cctgggtaca agacacaaaa ccagggccca tgggacgaag gccgggtaga gattgacttc   3300
gattactgcc caggaactac ggtcaccctg agtgagagct gcggacaccg tggacctgcc   3360
actcgcacca ccacagagag cggaaagttg ataacagatt ggtgctgcag gagctgcacc   3420
ttaccaccac tgcgctacca aactgacagc ggctgttggt atggtatgga gatcagacca   3480
cagagacatg atgaaaagac cctcgtgcag tcacaagtga atgcttataa tgctgatatg   3540
attgaccctt ttcagttggg ccttctggtc gtgttcttgg ccacccagga ggtccttcgc   3600
aagaggtgga cagccaagat cagcatgcca gctatactga ttgctctgct agtcctggtg   3660
tttgggggca ttacttacac tgatgtgtta cgctatgtca tcttggtggg ggcagctttc   3720
gcagaatcta attcgggagg agacgtggta cacttggcgc tcatggcgac cttcaagata   3780
caaccagtgt ttatggtggc atcgtttctc aaagcgagat ggaccaacca ggagaacatc   3840
ttgttgatgt tggcggctgt tttcttcaa atggcttatc acgatgcccg ccaaattctg   3900
ctctgggaga tccctgatgt gttgaattca ctggcggtag cttggatgat actgagagcc   3960
ataacattca caacgacatc aaacgtggtt gttccgctgc tagccctgct aacacccggg   4020
ctgagatgct tgaatctgga tgtgtacagg atactgctgt tgatggtcgg aataggcagc   4080
ttgatcaggg agaagaggag tgcagctgca aaaaagaaag gagcaagtct gctatgcttg   4140
gctctagcct caacaggact tttcaacccc atgatccttg ctgctggact gattacatgt   4200
gatcccaacc gtaaacgcgg atggcccgca actgaagtga tgcagctgt cggcctgatg   4260 tttgccatcg tcggagggct ggcagagctt gacattgact ccatgccat tccaatgact   4320 atcgcgggc tcatgtttgc tgcttccgtg atttctggga aatcaacaga tatgtggatt   4380
gagagaacgg cggacatttc ctgggaaagt gatgcagaaa ttacaggctc gagcgaaaga   4440
gttgatgtgc ggcttgatga tgatggaaac ttccagctca tgaatgatcc aggagcacct   4500
tggaagatat ggatgctcag aatggtctgt ctcgcgatta gtgcgtacac ccctggca   4560 atcttgccct cagtagttgg attttggata actctccaat acacaaagag aggaggcgtg   4620
ttgtgggaca ctccctcacc aaaggagtac aaaaagggg acacgaccac cggcgtctac   4680
aggatcatga ctcgtgggct gctcggcagt tatcaagcag gagcgggcgt gatggttgaa   4740
ggtgttttcc acacccttg gcatacaaca aaaggagccg ctttgatgag cggagagggc   4800
cgcctggacc catactgggg cagtgtcaag gaggatcgac tttgttacgg aggaccctgg   4860
aaattgcagc acaagtggaa cgggcaggat gaggtgcaga tgattgtggt ggaacctggc   4920
aagaacgtta agaacgtcca gacgaaacca ggggtgttca aaacacctga aggagaaatc   4980
```

-continued

```
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa acaaggagg     5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc taggggaggc ggcggcaata ttcatgacag ccaccccacc aggcacttca    5580
gatccattcc cagagtccaa ttcaccaatt tccgacttac agactgagat cccggatcga    5640
gcttggaact ctggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atgggggcta actttaaggc gagcagggtg    5880
attgacagcc ggaagagtgt gaaaccaacc atcataacga aggagaagg gagagtgatc     5940
ctgggagaac catctgcagt gacagcagct agtgccgccc agagacgtgg acgtatcggt    6000
agaaatccgt cgcaagttgg tgatgagtac tgttatgggg gcacacgaa tgaagacgac     6060
tcgaacttcg cccattggac tgaggcacga atcatgctgg acaacatcaa catgccaaac    6120
ggactgatcg ctcaattcta ccaaccagag cgtgagaagg tatataccat ggatggggaa    6180
taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg gtgaaaggaa gattctgagg ccgcgctgga ttgacgccag ggtgtactcg    6420
gatcaccagg cactaaaggc gttcaaggac ttcgcctcgg gaaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac ctttttctgt tggatggctg aagttccagg aacgaagatc    6780
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttttggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctgggggcaa gtcaccctca ccgttacggt aacagcggca    7260
acactccttt tttgccacta tgcctacatg gttcccggtt ggcaagctga ggcaatgcgc    7320
```

```
tcagcccagc ggcggacagc ggccggaatc atgaagaacg ctgtagtgga tggcatcgtg      7380
gccacggacg tcccagaatt agagcgcacc acacccatca tgcagaagaa agttggacag      7440
atcatgctga tcttggtgtc tctagctgca gtagtagtga acccgtctgt gaagacagta      7500
cgagaagccg aattttgat cacggccgca gcggtgacgc tttgggagaa tggagcaagc       7560
tctgtttgga acgcaacaac tgccatcgga ctctgccaca tcatgcgtgg gggttggttg      7620
tcatgtctat ccataacatg gacactcata agaacatgg aaaaaccagg actaaaaga       7680 ggtggggcaa aaggacgcac cttgggagag gtttggaaag aaagactcaa ccagatgaca      7740
aaagaagagt tcactaggta ccgcaaagag gccatcatcg aagtcgatcg ctcagcagca      7800
aaacacgcca ggaaagaagg caatgccact ggagggcatc cagtctctag ggcacagca       7860 aaactgagat ggctggtcga acggaggttt ctcgaaccgg tcggaaaagt gattgacctt      7920
ggatgtggaa gaggcggttg gtgttactat atggcaaccc aaaaagagt ccaagaagtc       7980 agagggtaca caaagggcgg tcccggacat gaagagcccc aactagtgca aagttatgga      8040
tggaacattg tcaccatgaa gagtggagtg gatgtgttct acagaccttc tgagtgttgt      8100
gacaccctcc tttgtgacat cggagagtcc tcgtcaagtg ctgaggttga agagcatagg      8160
acgattcggg tccttgaaat ggttgaggac tggctgcacc gagggccaag ggaattttgc      8220
gtgaaggtgc tctgccccta catgccgaaa gtcatagaga gatggagct gctccaacgc       8280 cggtatgggg gggactggt cagaaaccca ctctcacgga attccacgca cgagatgtat       8340
tgggtgagtc gagcttcagg caatgtggta cattcagtga atatgaccag ccaggtgctc      8400
ctaggaagaa tggaaaaaag gacctggaag ggaccccaat acgaggaaga tgtaaacttg      8460
ggaagtggaa ccagggcggt gggaaaaccc ctgctcaact cagacaccag taaaatcaag      8520
aacaggattg aacgactcag gcgtgagtac agttcgacgt ggcaccacga tgagaaccac      8580
ccatatagaa cctggaacta tcacggcagt tatgatgtga agcccacagg ctccgccagt      8640
tcgctggtca atggagtggt caggctcctc tcaaaaccat gggacaccat cacgaatgtt      8700
accaccatgg ccatgactga cactactccc ttcgggcagc agcgagtgtt caaagagaag      8760
gtggacacga aagctcctga accgccagaa ggagtgaagt acgtgctcaa cgagaccacc      8820
aactggttgt gggcgttttt ggccagagaa aaacgtccaa ggatgtgctc tcgagaggag      8880
ttcataagaa aggtcaacag caatgcagct ttgggtgcca tgtttgaaga gcagaatcaa      8940
tggaggagcg ccagagaggc agttgaagat ccaaaatttt gggagatggt ggatgaggag      9000
cgcgaggcac atctgcgggg ggaatgtcac acttgcattt acaacatgat gggaaagaga      9060
gagaaaaaac ccggagagtt cggaaaggcc aagggaagca gagccatttg gttcatgtgg      9120 ttcgagctc gctttctgga gttcgaggct ctggtttttc tcaatgaaga ccactggctt       9180
ggaagaaaga actcaggagg aggtgtcgag gcttgggcc tccaaaaact gggttacatc       9240
ctgcgtgaag ttgcacccg gcctggggc aagatctatg ctgatgacac agctggctgg        9300
gacacccgca tcacgagagc tgacttggaa aatgaagcta aggtgcttga gctgcttgat      9360
ggggaacatc ggcgtcttgc cagggccatc attgagctca cctatcgtca caagttgtg       9420 aaagtgatgc gcccggctgc tgatggaaga accgtcatgg atgttatctc cagagaagat      9480 cagagggga gtgacaagt tgtcacctac gcccctaaaca cttttcaccaa cctgccgtc       9540 cagctggtga ggatgatgga aggggaagga gtgattggcc cagatgatgt ggagaaactc      9600
acaaaaggga aaggacccaa agtcaggacc tggctgtttg agaatgggga agaaagactc      9660
agccgcatgg ctgtcagtgg agatgactgt gtggtaaagc ccctggacga tcgctttgcc      9720
```

-continued

```
acctcgctcc acttcctcaa tgctatgtca aaggttcgca aagacatcca agagtggaaa      9780
ccgtcaactg gatggtatga ttggcagcag gttccatttt gctcaaacca tttcactgaa      9840
ttgatcatga aagatggaag aacactggtg gttccatgcc gaggacagga tgaattggta      9900
ggcagagctc gcatatctcc aggggccgga tggaacgtcc gcgacactgc ttgtctggct      9960
aagtcttatg cccagatgtg gctgcttctg tacttccaca gaagagacct gcggctcatg     10020
gccaacgcca tttgctccgc tgtccctgtg aattgggtcc ctaccggaag aaccacgtgg     10080
tccatccatg caggaggaga gtggatgaca acagaggaca tgttggaggt ctggaaccgt     10140
gtttggatag aggagaatga atggatggaa gacaaaaccc cagtggagaa atggagtgac     10200
gtcccatatt caggaaaacg agaggacatc tggtgtggca gcctgattgg cacaagagcc     10260
cgagccacgt gggcagaaaa catccaggtg gctatcaacc aagtcagagc aatcatcgga     10320
gatgagaagt atgtggatta catgagttca ctaaagagat atgaagacac aactttggtt     10380
gaggacacag tactgtagat atttaatcaa ttgtaaatag acaatataag tatgcataaa     10440
agtgtagttt tatagtagta tttagtggtg ttagtgtaaa tagttaagaa aattttgagg     10500
agaaagtcag gccgggaagt tcccgccacc ggaagttgag tagacggtgc tgcctgcgac     10560
tcaaccccag gaggactggg tgaacaaagc cgcgaagtga tccatgtaag ccttcagaac     10620
cgtctcggaa ggaggacccc acatgttgta acttcaaagc ccaatgtcag accacgctac     10680
ggcgtgctac tctgcggaga gtgcagtctg cgatagtgcc ccaggaggac tgggttaaca     10740
aaggcaaacc aacgccccac gcggccctag ccccggtaat ggtgttaacc agggcgaaag     10800
gactagaggt tagaggagac cccgcggttt aaagtgcacg gcccagcctg gctgaagctg     10860
taggtcaggg gaaggactag aggttagtgg agaccccgtg ccacaaaaca ccacaacaaa     10920
acagcatatt gacacctggg atagactagg agatcttctg ctctgcacaa ccagccacac     10980
ggcacagtgc gccgacaatg gtggctggtg gtgcgagaac acaggatct               11029
```

```
<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caaaggatcc taatacgact cactatagag tagttcgcct gtgtgagctg a               51

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgttctcct ggttggtcca                                                  20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
gtagagattg acttcgatta c                                              21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtacttcac tccttctggc                                                20

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccccaacta gtgcaaagtt atggatggaa c                                   31

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attcttctcg agagcacatc cttggacgtt tttctctggc c                        41

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgctctcga gaggagttca taaga                                          25

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aacaatctag agatcctgtg ttctcgcacc ac                                  32

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 11
caaaggatcc taatacgact cactatagag tagttcgcct gtgtgagctg a        51

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagccctctt aagtccaatc aag                                       23

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttccttctct taagatgggc atcaatgctc gtgat                          35

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgttctcct ggttggtcca                                           20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtagagattg acttcgatta c                                         21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtacttcac tccttctggc                                           20

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
gccccaacta gtgcaaagtt atggatggaa c                                      31
```

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
attcttctcg agagcacatc cttggacgtt tttctctggc c                           41
```

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
gtgctctcga gaggagttca taaga                                             25
```

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
aacaatctag agatcctgtg ttctcgcacc ac                                     32
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
ataattatgc atccgcccct ctccctc                                           27
```

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
ccagccatgc attacttgta cagctcgtcc ca                                     32
```

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctttgaaaa acacgatgat aataccatga ttgaacaaga tggattgc            48

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acaaccatgc atcagaagaa ctcgtcaaga ag                              32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tacactctta agatggcttc caaggtgtac ga                              32

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cacaagctta agctgctcgt tcttcagcac g                               31

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gatctctaga t                                                     11